US009826999B2

(12) United States Patent
Jenkins et al.

(10) Patent No.: US 9,826,999 B2
(45) Date of Patent: Nov. 28, 2017

(54) METHODS AND APPARATUS FOR TREATING DISORDERS OF THE EAR NOSE AND THROAT

(71) Applicant: Acclarent, Inc., Menlo Park, CA (US)

(72) Inventors: Thomas R. Jenkins, Alameda, CA (US); Eric Goldfarb, Belmont, CA (US); Tom Thanh Vo, Mountain View, CA (US); Joshua Makower, Los Altos, CA (US); Robert N. Wood, Indian Beach, NC (US); Ronda M. Heiser, San Jose, CA (US); Christopher Larsen, Oakland, CA (US); Daniel T. Harfe, Los Altos, CA (US)

(73) Assignee: Acclarent, Inc., Irvine, CA (US)

( * ) Notice: Subject to any disclaimer, the term of this patent is extended or adjusted under 35 U.S.C. 154(b) by 491 days.

(21) Appl. No.: 13/858,580

(22) Filed: Apr. 8, 2013

(65) Prior Publication Data
US 2013/0261388 A1 Oct. 3, 2013

Related U.S. Application Data

(63) Continuation of application No. 12/561,147, filed on Sep. 16, 2009, now Pat. No. 8,414,473, which is a (Continued)

(51) Int. Cl.
*A61M 29/00* (2006.01)
*A61B 17/24* (2006.01)
(Continued)

(52) U.S. Cl.
CPC .......... *A61B 17/24* (2013.01); *A61B 1/0014* (2013.01); *A61B 1/126* (2013.01); *A61B 1/233* (2013.01);
(Continued)

(58) Field of Classification Search
CPC ........ A61M 2025/09116; A61M 25/10; A61M 2025/09008; A61M 2029/025;
(Continued)

(56) References Cited

U.S. PATENT DOCUMENTS 446,173 A 2/1891 Hancock
504,424 A 9/1893 De Pezzer
(Continued)

FOREIGN PATENT DOCUMENTS

CA 2013323 9/1990
CH 668188 12/1988
(Continued)

OTHER PUBLICATIONS http://dictionary.reference.com/browse/bent; Definition of "bent" as accessed on Sep. 10, 2015.*
(Continued)

*Primary Examiner* — Jonathan Miles
(74) *Attorney, Agent, or Firm* — Frost Brown Todd LLC

(57) ABSTRACT

A device for dilating an ostium of a paranasal sinus of a human or animal subject may include: a handle; an elongate shaft having a proximal end coupled with the handle and extending to a distal end; a guidewire disposed through at least a portion of the shaft lumen; a dilator having a non-expanded configuration and an expanded configuration; and a slide member coupled with at least one of the guidewire or the dilator through the longitudinal opening of the shaft for advancing the guidewire and/or the dilator relative to the shaft.

18 Claims, 26 Drawing Sheets

Related U.S. Application Data continuation-in-part of application No. 11/193,020, filed on Jul. 29, 2005, which is a continuation-in-part of application No. 11/150,847, filed on Jun. 10, 2005, now Pat. No. 7,803,150, which is a continuation-in-part of application No. 11/116,118, filed on Apr. 26, 2005, now Pat. No. 7,720,521, which is a continuation-in-part of application No. 10/944,270, filed on Sep. 17, 2004, now abandoned, which is a continuation-in-part of application No. 10/829,917, filed on Apr. 21, 2004, now Pat. No. 7,654,997.

(60) Provisional application No. 61/098,157, filed on Sep. 18, 2008.

(51) Int. Cl.
   A61M 25/10    (2013.01)
   A61M 25/00    (2006.01)
   A61B 1/00     (2006.01)
   A61B 1/12     (2006.01)
   A61B 1/233    (2006.01)
   A61M 29/02    (2006.01)
   A61M 25/09    (2006.01)
   A61B 17/00    (2006.01)

(52) U.S. Cl.
   CPC ........ A61M 25/0068 (2013.01); A61M 25/09 (2013.01); A61M 25/10181 (2013.11); A61M 29/02 (2013.01); A61B 2017/00535 (2013.01); A61M 25/1018 (2013.01); A61M 2025/09116 (2013.01); A61M 2210/0618 (2013.01)

(58) Field of Classification Search
   CPC ... A61M 29/02; A61M 25/0068; A61B 17/24; A61B 1/233; A61F 2/2433; A61F 2/958; A61F 2002/9517
   See application file for complete search history.

(56) References Cited

U.S. PATENT DOCUMENTS

| | | |
|---|---|---|
| 513,667 A | 1/1894 | Buckingham |
| 705,346 A | 7/1902 | Hamilton |
| 798,775 A | 9/1905 | Forsyte |
| 816,792 A | 4/1906 | Green |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,828,986 A | 10/1931 | Stevens |
| 1,878,671 A | 9/1932 | Cantor |
| 2,201,749 A | 5/1940 | Vandergrift |
| 2,493,326 A | 1/1950 | Trinder |
| 2,525,183 A | 10/1950 | Robison |
| 2,847,997 A | 8/1958 | Tibone |
| 2,899,227 A | 8/1959 | Jeanrenaud |
| 2,906,179 A | 9/1959 | Bower |
| 2,995,832 A | 8/1961 | Alderson |
| 3,009,265 A | 11/1961 | Bexark |
| 3,037,286 A | 6/1962 | Bower |
| 3,173,418 A | 3/1965 | Baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,447,061 A | 5/1969 | Russell et al. |
| 3,469,578 A | 9/1969 | Bierman |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow |
| 3,731,963 A | 5/1973 | Pond |
| 3,766,924 A | 10/1973 | Pidgeon |
| 3,792,391 A | 2/1974 | Ewing |
| 3,800,788 A | 4/1974 | White |
| 3,802,096 A | 4/1974 | Matern |
| 3,804,081 A | 4/1974 | Kinoshita |
| 3,834,394 A | 9/1974 | Hunter et al. |
| 3,847,145 A | 11/1974 | Grossan |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin et al. |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,299,226 A | 11/1981 | Banka |
| 4,299,227 A | 11/1981 | Lincoff |
| 4,312,353 A | 1/1982 | Shahbabian |
| 4,338,941 A | 7/1982 | Payton |
| D269,204 S | 5/1983 | Trepp |
| 4,388,941 A | 6/1983 | Riedhammer |
| RE31,351 E | 8/1983 | Falconer |
| 4,435,716 A | 3/1984 | Zandbergen |
| 4,437,856 A | 3/1984 | Valli |
| 4,445,892 A | 5/1984 | Hussein et al. |
| 4,450,150 A | 5/1984 | Sidman |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,554,929 A | 11/1985 | Samson et al. |
| 4,564,364 A | 1/1986 | Zaffaroni et al. |
| 4,571,239 A | 2/1986 | Heyman |
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,641,654 A | 2/1987 | Samson et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,682,607 A | 7/1987 | Vaillancourt et al. |
| 4,686,965 A | 8/1987 | Bonnet et al. |
| 4,691,948 A | 9/1987 | Austin, Jr. et al. |
| 4,696,544 A | 9/1987 | Costella |

(56) References Cited

U.S. PATENT DOCUMENTS

| | | |
|---|---|---|
| 4,700,694 A | 10/1987 | Shishido |
| 4,705,801 A | 11/1987 | Martin et al. |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,755,171 A | 7/1988 | Tennant |
| 4,771,776 A | 9/1988 | Powell et al. |
| 4,784,117 A | 11/1988 | Miyazaki |
| 4,793,359 A | 12/1988 | Sharrow |
| 4,795,439 A | 1/1989 | Guest |
| 4,796,629 A | 1/1989 | Grayzel |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,834,709 A | 5/1989 | Banning et al. |
| 4,846,186 A | 7/1989 | Box et al. |
| 4,847,258 A | 7/1989 | Sturm et al. |
| 4,851,228 A | 7/1989 | Zentner et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |
| 4,943,275 A | 7/1990 | Stricker |
| 4,946,466 A | 8/1990 | Pinchuk et al. |
| 4,953,553 A | 9/1990 | Tremulis |
| 4,961,433 A | 10/1990 | Christian |
| 4,966,163 A | 10/1990 | Kraus et al. |
| 4,984,581 A | 1/1991 | Stice |
| 4,991,588 A | 2/1991 | Pflueger et al. |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,009,655 A | 4/1991 | Daignault, Jr. et al. |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,040,548 A | 8/1991 | Yock |
| 5,041,089 A | 8/1991 | Mueller et al. |
| 5,044,678 A | 9/1991 | Detweiler |
| 5,053,007 A | 10/1991 | Euteneuer |
| 5,055,051 A | 10/1991 | Duncan |
| 5,060,660 A | 10/1991 | Gamble et al. |
| 5,067,489 A | 11/1991 | Lind |
| 5,069,226 A | 12/1991 | Tamauchi et al. |
| 5,084,010 A | 1/1992 | Plaia et al. |
| 5,087,244 A | 2/1992 | Wolinsky et al. |
| 5,087,246 A | 2/1992 | Smith |
| 5,090,595 A | 2/1992 | Vandeninck |
| 5,090,910 A | 2/1992 | Narlo |
| 5,090,959 A | 2/1992 | Samson et al. |
| 5,099,845 A | 3/1992 | Besz et al. |
| 5,102,402 A | 4/1992 | Dror et al. |
| 5,112,228 A | 5/1992 | Zouras |
| 5,116,311 A | 5/1992 | Lofstedt |
| 5,127,393 A | 7/1992 | McFarlin et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Oliver et al. |
| 5,156,595 A | 10/1992 | Adams |
| 5,163,989 A | 11/1992 | Campbell et al. |
| 5,165,420 A * | 11/1992 | Strickland ........... A61M 1/0058 600/581 |
| 5,167,220 A | 12/1992 | Brown |
| 5,168,864 A | 12/1992 | Shockey |
| 5,169,043 A | 12/1992 | Catania |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wettermann |
| 5,189,110 A | 2/1993 | Ikematu et al. |
| 5,195,168 A | 3/1993 | Yong |
| 5,195,971 A | 3/1993 | Sirhan |
| 5,197,457 A | 3/1993 | Adair |
| 5,201,908 A | 4/1993 | Jones |
| 5,207,695 A | 5/1993 | Trout, III |
| 5,211,952 A | 5/1993 | Spicer et al. |
| 5,213,576 A | 5/1993 | Abiuso et al. |
| 5,215,105 A | 6/1993 | Kizelshteyn et al. |
| 5,221,260 A | 6/1993 | Burns et al. |
| 5,226,302 A | 7/1993 | Anderson |
| 5,230,348 A | 7/1993 | Ishibe et al. |
| 5,236,422 A | 8/1993 | Eplett, Jr. |
| 5,238,004 A | 8/1993 | Sahatjian et al. |
| 5,243,996 A | 9/1993 | Hall |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,256,144 A | 10/1993 | Kraus et al. |
| 5,263,926 A | 11/1993 | Wilk |
| 5,264,260 A | 11/1993 | Saab |
| 5,267,965 A | 12/1993 | Deneiga |
| 5,269,752 A | 12/1993 | Bennett |
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |
| 5,290,310 A | 3/1994 | Makower et al. |
| 5,295,694 A | 3/1994 | Levin |
| 5,300,085 A | 4/1994 | Yock |
| 5,304,123 A | 4/1994 | Atala et al. |
| 5,306,272 A | 4/1994 | Cohen et al. |
| 5,308,326 A | 5/1994 | Zimmon |
| 5,312,430 A | 5/1994 | Rosenbluth et al. |
| 5,313,967 A | 5/1994 | Lieber et al. |
| 5,314,408 A | 5/1994 | Salmon et al. |
| 5,314,417 A | 5/1994 | Stephens et al. |
| 5,314,443 A | 5/1994 | Rudnick |
| 5,315,618 A | 5/1994 | Yoshida |
| 5,318,528 A | 6/1994 | Heaven et al. |
| 5,324,306 A | 6/1994 | Makower et al. |
| 5,333,620 A | 8/1994 | Moutafis et al. |
| 5,334,143 A | 8/1994 | Carroll |
| 5,334,167 A | 8/1994 | Cocanower |
| 5,334,187 A | 8/1994 | Fischell et al. |
| 5,335,671 A | 8/1994 | Clement |
| 5,336,163 A | 8/1994 | DeMane et al. |
| 5,341,818 A | 8/1994 | Abrams et al. |
| 5,342,296 A | 8/1994 | Persson et al. |
| 5,343,865 A | 9/1994 | Gardineer et al. |
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,356,418 A | 10/1994 | Shturman |
| 5,368,049 A | 11/1994 | Raman et al. |
| 5,368,558 A | 11/1994 | Nita |
| 5,368,566 A | 11/1994 | Crocker |
| 5,370,640 A | 12/1994 | Kolff |

(56) References Cited

U.S. PATENT DOCUMENTS

| | | |
|---|---|---|
| 5,372,138 A | 12/1994 | Crowley et al. |
| 5,372,584 A | 12/1994 | Zink et al. |
| D355,031 S | 1/1995 | Yoshikawa |
| 5,378,234 A | 1/1995 | Hammerslag et al. |
| 5,385,562 A | 1/1995 | Adams et al. |
| 5,386,817 A | 2/1995 | Jones |
| 5,386,828 A | 2/1995 | Owens et al. |
| 5,391,147 A | 2/1995 | Imran et al. |
| 5,391,179 A | 2/1995 | Mezzoli |
| 5,395,367 A | 3/1995 | Wilk |
| 5,402,799 A | 4/1995 | Colon et al. |
| 5,409,444 A | 4/1995 | Kensey et al. |
| 5,411,475 A | 5/1995 | Atala et al. |
| 5,411,476 A | 5/1995 | Abrams et al. |
| 5,411,477 A | 5/1995 | Saab |
| 5,415,633 A | 5/1995 | Lazarus |
| 5,425,370 A | 6/1995 | Vilkomerson |
| 5,439,446 A | 8/1995 | Barry |
| 5,441,494 A | 8/1995 | Ortiz |
| 5,441,497 A | 8/1995 | Narciso, Jr. |
| 5,445,646 A | 8/1995 | Euteneuer et al. |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,459,700 A | 10/1995 | Jacobs |
| 5,465,717 A | 11/1995 | Imran et al. |
| 5,465,733 A | 11/1995 | Hinohara et al. |
| 5,478,309 A | 12/1995 | Sweezer et al. |
| 5,478,565 A | 12/1995 | Geria |
| 5,486,181 A | 1/1996 | Cohen et al. |
| 5,496,338 A | 3/1996 | Miyagi et al. |
| 5,497,783 A | 3/1996 | Urick et al. |
| 5,507,301 A | 4/1996 | Wasicek et al. |
| 5,507,725 A | 4/1996 | Savage et al. |
| 5,507,766 A | 4/1996 | Kugo et al. |
| 5,507,795 A | 4/1996 | Chiang et al. |
| 5,512,055 A | 4/1996 | Domb et al. |
| 5,514,128 A | 5/1996 | Hillsman et al. |
| 5,519,532 A | 5/1996 | Broome |
| 5,531,676 A | 7/1996 | Edwards et al. |
| 5,533,985 A | 7/1996 | Wang |
| 5,538,008 A | 7/1996 | Crowe |
| 5,546,964 A | 8/1996 | Stangerup |
| 5,549,542 A | 8/1996 | Kovalcheck |
| 5,558,073 A | 9/1996 | Pomeranz et al. |
| 5,558,652 A | 9/1996 | Henke |
| 5,562,619 A | 10/1996 | Mirarchi et al. |
| 5,568,809 A | 10/1996 | Ben-haim |
| 5,571,086 A | 11/1996 | Kaplan et al. |
| 5,578,007 A | 11/1996 | Imran |
| 5,578,048 A | 11/1996 | Pasqualucci et al. |
| 5,582,575 A | 12/1996 | Heckele et al. |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |
| 5,601,594 A | 2/1997 | Best |
| 5,607,386 A | 3/1997 | Flam |
| 5,617,870 A | 4/1997 | Hastings et al. |
| 5,626,374 A | 5/1997 | Kim |
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |
| 5,707,376 A | 1/1998 | Kavteladze et al. |
| 5,707,389 A | 1/1998 | Louw et al. |
| 5,708,175 A | 1/1998 | Loyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,720,719 A | 2/1998 | Edwards et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,749,357 A | 5/1998 | Linder |
| 5,752,513 A | 5/1998 | Acker et al. |
| 5,752,971 A | 5/1998 | Rosenbluth et al. |
| 5,762,604 A | 6/1998 | Kieturakis |
| 5,766,158 A | 6/1998 | Opolski |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,820,592 A | 10/1998 | Hammerslag |
| 5,824,044 A | 10/1998 | Quiachon et al. |
| 5,824,048 A | 10/1998 | Tuch |
| 5,824,173 A | 10/1998 | Fontirroche et al. |
| 5,826,576 A | 10/1998 | West |
| 5,827,224 A | 10/1998 | Shippert |
| 5,827,323 A | 10/1998 | Klieman et al. |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,836,951 A | 11/1998 | Rosenbluth et al. |
| 5,837,313 A | 11/1998 | Ding et al. |
| 5,843,089 A | 12/1998 | Sahatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings et al. |
| 5,879,324 A | 3/1999 | Von Hoffmann |
| 5,882,333 A | 3/1999 | Schaer et al. |
| 5,882,346 A | 3/1999 | Pomeranz et al. |
| 5,887,467 A | 3/1999 | Butterweck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |

(56) References Cited

U.S. PATENT DOCUMENTS

| | | |
|---|---|---|
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,967,984 A | 10/1999 | Chu et al. |
| 5,968,085 A | 10/1999 | Morris et al. |
| 5,971,975 A | 10/1999 | Mills et al. |
| 5,976,074 A | 11/1999 | Moriyama |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,987,344 A | 11/1999 | West |
| 5,993,462 A | 11/1999 | Pomeranz et al. |
| 5,997,562 A | 12/1999 | Zadno-Azizi et al. |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,063,022 A | 5/2000 | Ben-Haim |
| 6,063,079 A | 5/2000 | Hovda et al. |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,102,891 A | 8/2000 | van Erp et al. |
| 6,109,268 A | 8/2000 | Thapliyal et al. |
| 6,113,567 A | 9/2000 | Becker |
| 6,117,105 A | 9/2000 | Bresnaham et al. |
| 6,122,541 A | 9/2000 | Cosman et al. |
| 6,123,697 A | 9/2000 | Shippert |
| 6,135,991 A | 10/2000 | Muni et al. |
| 6,136,006 A | 10/2000 | Johnson et al. |
| 6,139,510 A | 10/2000 | Palermo |
| 6,142,957 A | 11/2000 | Diamond et al. |
| 6,146,402 A | 11/2000 | Munoz |
| 6,146,415 A | 11/2000 | Fitz |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim et al. |
| 6,174,280 B1 | 1/2001 | Oneda et al. |
| 6,176,829 B1 | 1/2001 | Vilkomerson |
| 6,179,776 B1 | 1/2001 | Adams et al. |
| 6,179,788 B1 | 1/2001 | Sullivan |
| 6,179,811 B1 | 1/2001 | Fugoso et al. |
| 6,183,433 B1 | 2/2001 | Bays |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,206,900 B1 | 3/2001 | Tabatabaei et al. |
| 6,213,975 B1 | 4/2001 | Laksin |
| 6,221,042 B1 | 4/2001 | Adams |
| 6,231,543 B1 | 5/2001 | Hegde et al. |
| 6,234,958 B1 | 5/2001 | Snoke et al. |
| 6,238,364 B1 | 5/2001 | Becker |
| 6,238,391 B1 | 5/2001 | Olsen et al. |
| 6,238,430 B1 * | 5/2001 | Klumb .................. A61F 2/88 606/108 |
| 6,241,519 B1 | 6/2001 | Sedelmayer |
| 6,249,180 B1 | 6/2001 | Maalej et al. |
| 6,254,550 B1 | 7/2001 | McNamara et al. |
| 6,268,574 B1 | 7/2001 | Edens |
| 6,270,477 B1 | 8/2001 | Bagaoisan et al. |
| 6,280,433 B1 | 8/2001 | McIvor et al. |
| 6,283,908 B1 | 9/2001 | Powell et al. |
| 6,290,689 B1 | 9/2001 | Delaney et al. |
| 6,293,957 B1 | 9/2001 | Peters et al. |
| 6,295,990 B1 | 10/2001 | Lewis et al. |
| 6,302,875 B1 | 10/2001 | Makower et al. |
| 6,304,768 B1 | 10/2001 | Blume et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,328,730 B1 | 12/2001 | Harkrider, Jr. |
| 6,332,089 B1 | 12/2001 | Acker et al. |
| 6,332,891 B1 | 12/2001 | Himes |
| 6,340,360 B1 | 1/2002 | Lyles et al. |
| 6,344,028 B1 | 2/2002 | Barry |
| 6,348,041 B1 | 2/2002 | Klint |
| 6,352,503 B1 | 3/2002 | Matsui et al. |
| 6,364,856 B1 | 4/2002 | Ding et al. |
| 6,375,615 B1 | 4/2002 | Flaherty et al. |
| 6,375,629 B1 | 4/2002 | Muni et al. |
| 6,379,319 B1 | 4/2002 | Garibotto et al. |
| 6,381,485 B1 | 4/2002 | Hunter et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,419,653 B2 | 7/2002 | Edwards et al. |
| 6,423,012 B1 | 7/2002 | Kato et al. |
| 6,425,877 B1 | 7/2002 | Edwards |
| 6,432,986 B2 | 8/2002 | Levin |
| 6,436,119 B1 | 8/2002 | Erb et al. |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,488,653 B1 | 12/2002 | Lombardo |
| 6,491,940 B1 | 12/2002 | Levin |
| 6,494,894 B2 | 12/2002 | Mirarchi |
| 6,500,130 B2 | 12/2002 | Gordon et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,503,263 B2 | 1/2003 | Adams |
| 6,511,418 B2 | 1/2003 | Shahidi et al. |
| 6,511,471 B2 | 1/2003 | Rosenman et al. |
| 6,514,249 B1 | 2/2003 | Maguire et al. |
| 6,517,478 B2 | 2/2003 | Khadem |
| 6,520,954 B2 | 2/2003 | Ouchi |

(56) References Cited

U.S. PATENT DOCUMENTS

| | | |
|---|---|---|
| 6,524,129 B2 | 2/2003 | Cote et al. |
| 6,524,299 B1 | 2/2003 | Tran et al. |
| 6,526,302 B2 | 2/2003 | Hassett |
| 6,527,753 B2 | 3/2003 | Sekine et al. |
| 6,529,756 B1 | 3/2003 | Phan et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,223 B1 | 4/2003 | Kokish |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,562,022 B2 | 5/2003 | Hoste et al. |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,718 B2 | 7/2003 | Hayzelden et al. |
| 6,585,794 B2 | 7/2003 | Shimoda et al. |
| 6,589,164 B1 | 7/2003 | Flaherty |
| 6,589,237 B2 | 7/2003 | Woloszko et al. |
| 6,591,130 B2 | 7/2003 | Shahidi |
| 6,596,009 B1 | 7/2003 | Jelic |
| 6,607,546 B1 | 8/2003 | Murken |
| 6,610,059 B1 | 8/2003 | West, Jr. |
| 6,612,999 B2 | 9/2003 | Brennan et al. |
| 6,613,066 B1 | 9/2003 | Fukaya et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,645,193 B2 | 11/2003 | Mangosong |
| 6,652,472 B2 | 11/2003 | Jafari et al. |
| 6,652,480 B1 | 11/2003 | Imran et al. |
| 6,656,166 B2 | 12/2003 | Lurie et al. |
| 6,659,106 B1 | 12/2003 | Hovda et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,679,833 B2 | 1/2004 | Smith et al. |
| 6,679,871 B2 | 1/2004 | Hahnen |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,183 B2 | 4/2004 | Clayman et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,719,763 B2 | 4/2004 | Chung et al. |
| 6,726,701 B2 | 4/2004 | Gilson et al. |
| 6,738,656 B1 | 5/2004 | Ferre et al. |
| 6,741,884 B1 | 5/2004 | Freeman et al. |
| 6,755,812 B2 | 6/2004 | Peterson et al. |
| 6,758,857 B2 | 7/2004 | Cioanta et al. |
| 6,776,772 B1 | 8/2004 | de Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,811,544 B2 | 11/2004 | Schaer |
| 6,817,364 B2 | 11/2004 | Garibaldi et al. |
| 6,817,976 B2 | 11/2004 | Rovengo |
| 6,827,683 B2 | 12/2004 | Otawara |
| 6,827,701 B2 | 12/2004 | MacMahon et al. |
| 6,832,715 B2 | 12/2004 | Eungard et al. |
| D501,677 S | 2/2005 | Becker |
| 6,849,062 B2 | 2/2005 | Kantor |
| 6,851,290 B1 | 2/2005 | Meier et al. |
| 6,855,136 B2 | 2/2005 | Dorros et al. |
| 6,860,264 B2 | 3/2005 | Christopher |
| 6,860,849 B2 | 3/2005 | Matsushita et al. |
| 6,866,669 B2 | 3/2005 | Buzzard et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,913,763 B2 | 7/2005 | Lerner |
| 6,927,478 B2 | 8/2005 | Paek |
| 6,939,361 B1 | 9/2005 | Kleshinski |
| 6,939,374 B2 | 9/2005 | Banik et al. |
| 6,953,431 B2 | 10/2005 | Barthel |
| 6,955,657 B1 | 10/2005 | Webler |
| 6,966,906 B2 | 11/2005 | Brown |
| 6,971,998 B2 | 12/2005 | Rosenman et al. |
| 6,979,290 B2 | 12/2005 | Mourlas et al. |
| 6,979,979 B2 | 12/2005 | Xu et al. |
| 6,984,203 B2 | 1/2006 | Tartaglia et al. |
| 6,989,024 B2 | 1/2006 | Hebert et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,004,173 B2 | 2/2006 | Sparks et al. |
| 7,004,176 B2 | 2/2006 | Lau |
| 7,008,412 B2 | 3/2006 | Maginot |
| 7,011,654 B2 | 3/2006 | Dubrul et al. |
| 7,022,105 B1 | 4/2006 | Edwards |
| 7,037,321 B2 | 5/2006 | Sachdeva |
| 7,043,961 B2 | 5/2006 | Pandey |
| 7,044,964 B2 | 5/2006 | Jang et al. |
| 7,048,711 B2 | 5/2006 | Rosenmann et al. |
| 7,052,474 B2 | 5/2006 | Castell et al. |
| 7,056,284 B2 | 6/2006 | Martone et al. |
| 7,056,287 B2 | 6/2006 | Taylor et al. |
| 7,056,303 B2 | 6/2006 | Dennis et al. |
| 7,056,314 B1 | 6/2006 | Florio et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,677 B2 | 9/2006 | Courtney et al. |
| 7,108,706 B2 | 9/2006 | Hogle |
| 7,117,039 B2 | 10/2006 | Manning et al. |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,207,981 B2 | 4/2007 | Quinn et al. |
| 7,214,201 B2 | 5/2007 | Burmeister et al. |
| 7,233,820 B2 | 6/2007 | Gilboa |
| 7,235,099 B1 | 6/2007 | Duncavage et al. |
| 7,237,313 B2 | 7/2007 | Skujins et al. |
| 7,248,914 B2 | 7/2007 | Hastings et al. |
| 7,252,677 B2 | 8/2007 | Burwell et al. |
| 7,282,057 B2 | 10/2007 | Surti et al. |
| 7,292,885 B2 | 11/2007 | Scott et al. |
| 7,294,345 B2 | 11/2007 | Haapakumpu et al. |
| 7,294,365 B2 | 11/2007 | Hayakawa et al. |
| 7,303,533 B2 | 12/2007 | Johansen et al. |
| 7,309,334 B2 | 12/2007 | von Hoffmann |
| 7,313,430 B2 | 12/2007 | Urquhart et al. |
| 7,316,168 B2 | 1/2008 | van der Knokke et al. |
| 7,316,656 B2 | 1/2008 | Shireman et al. |

(56) References Cited

U.S. PATENT DOCUMENTS

| | | |
|---|---|---|
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,343,920 B2 | 3/2008 | Toby et al. |
| 7,347,868 B2 | 3/2008 | Burnett et al. |
| 7,359,755 B2 | 4/2008 | Jones et al. |
| 7,361,168 B2 | 4/2008 | Makower et al. |
| 7,366,562 B2 | 4/2008 | Dukesherer |
| 7,371,210 B2 | 5/2008 | Brock et al. |
| 7,381,205 B2 | 6/2008 | Thommen |
| 7,384,407 B2 | 6/2008 | Rodriguez et al. |
| 7,410,480 B2 | 8/2008 | Muni et al. |
| 7,419,497 B2 | 9/2008 | Muni et al. |
| 7,438,701 B2 | 10/2008 | Theeuwes et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| 7,471,994 B2 | 12/2008 | Ford et al. |
| 7,481,218 B2 | 1/2009 | Djupesland |
| 7,481,800 B2 | 1/2009 | Jacques |
| D586,465 S | 2/2009 | Faulkner et al. |
| D586,916 S | 2/2009 | Faulkner et al. |
| 7,488,313 B2 | 2/2009 | Segal et al. |
| 7,488,337 B2 | 2/2009 | Saab et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,544,192 B2 | 6/2009 | Eaton et al. |
| 7,551,758 B2 | 6/2009 | Florent et al. |
| 7,559,925 B2 | 7/2009 | Goldfarb et al. |
| 7,566,300 B2 | 7/2009 | Devierre et al. |
| 7,610,104 B2 | 10/2009 | Kaplan et al. |
| 7,615,005 B2 | 11/2009 | Stefanchik et al. |
| 7,618,450 B2 | 11/2009 | Zarowski et al. |
| 7,625,335 B2 | 12/2009 | Deichmann et al. |
| 7,632,291 B2 | 12/2009 | Stephens et al. |
| 7,634,233 B2 | 12/2009 | Deng et al. |
| 7,641,644 B2 | 1/2010 | Chang et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,680,244 B2 | 3/2010 | Gertner et al. |
| 7,686,798 B2 | 3/2010 | Eaton et al. |
| 7,691,120 B2 | 4/2010 | Shluzas et al. |
| 7,697,972 B2 | 4/2010 | Verard et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,736,301 B1 | 6/2010 | Webler et al. |
| 7,740,642 B2 | 6/2010 | Becker |
| 7,753,929 B2 | 7/2010 | Becker |
| 7,753,930 B2 | 7/2010 | Becker |
| 7,758,497 B2 | 7/2010 | Hem |
| 7,771,409 B2 | 8/2010 | Chang et al. |
| 7,775,968 B2 | 8/2010 | Mathis |
| 7,785,315 B1 | 8/2010 | Muni et al. |
| 7,799,048 B2 | 9/2010 | Hudson et al. |
| 7,799,337 B2 | 9/2010 | Levin |
| 7,803,150 B2 | 9/2010 | Chang et al. |
| 7,833,282 B2 | 11/2010 | Mandpe |
| 7,837,672 B2 | 11/2010 | Intoccia |
| 7,840,254 B2 | 11/2010 | Glossop |
| 7,854,744 B2 | 12/2010 | Becker |
| 7,857,750 B2 | 12/2010 | Belafsky |
| D630,321 S | 1/2011 | Hamilton, Jr. |
| 7,875,050 B2 | 1/2011 | Samson et al. |
| D632,791 S | 2/2011 | Murner |
| 7,881,769 B2 | 2/2011 | Sobe |
| 7,883,717 B2 | 2/2011 | Varner et al. |
| 7,896,891 B2 | 3/2011 | Catanese, III et al. |
| 7,927,271 B2 | 4/2011 | Dimitriou et al. |
| 7,951,132 B2 | 5/2011 | Eaton et al. |
| 7,988,705 B2 | 8/2011 | Galdonik et al. |
| 7,993,353 B2 | 8/2011 | Roßner et al. |
| 8,002,740 B2 | 8/2011 | Willink et al. |
| 8,014,849 B2 | 9/2011 | Peckham |
| 8,016,752 B2 | 9/2011 | Armstrong et al. |
| 8,025,635 B2 | 9/2011 | Eaton et al. |
| 8,075,476 B2 | 12/2011 | Vargas |
| 8,080,000 B2 | 12/2011 | Makower et al. |
| 8,088,063 B2 | 1/2012 | Fujikura et al. |
| 8,088,101 B2 | 1/2012 | Chang et al. |
| 8,090,433 B2 | 1/2012 | Makower et al. |
| 8,100,933 B2 | 1/2012 | Becker |
| 8,104,483 B2 | 1/2012 | Taylor |
| 8,114,062 B2 | 2/2012 | Muni et al. |
| 8,114,113 B2 | 2/2012 | Becker |
| 8,123,722 B2 | 2/2012 | Chang et al. |
| 8,142,422 B2 | 3/2012 | Makower et al. |
| 8,146,400 B2 | 4/2012 | Goldfarb et al. |
| 8,147,545 B2 | 4/2012 | Avior |
| 8,167,821 B2 | 5/2012 | Sharrow |
| 8,172,828 B2 | 5/2012 | Chang et al. |
| 8,190,389 B2 | 5/2012 | Kim et al. |
| 8,197,433 B2 | 6/2012 | Cohen |
| 8,197,552 B2 | 6/2012 | Mandpe |
| 8,249,700 B2 | 8/2012 | Clifford et al. |
| 8,277,386 B2 | 10/2012 | Ahmed et al. |
| 8,317,816 B2 | 11/2012 | Becker |
| 8,337,454 B2 | 12/2012 | Eaton et al. |
| 8,388,642 B2 | 3/2013 | Muni et al. |
| 8,403,954 B2 | 3/2013 | Santin et al. |
| 8,414,473 B2 | 4/2013 | Jenkins et al. |
| 8,425,457 B2 | 4/2013 | John et al. |
| 8,439,687 B1 | 5/2013 | Morriss et al. |
| 8,475,360 B2 | 7/2013 | Brown |
| 8,521,259 B2 | 8/2013 | Mandrusov et al. |
| 8,529,439 B2 | 9/2013 | Ito et al. |
| 8,535,707 B2 | 9/2013 | Arensdorf et al. |
| 8,568,439 B2 | 10/2013 | Keith et al. |
| 8,740,292 B2 | 6/2014 | Kishi |
| 8,740,839 B2 | 6/2014 | Eaton et al. |
| 8,802,131 B2 | 8/2014 | Arensdorf et al. |
| 9,220,879 B2 | 12/2015 | Chang et al. |
| 9,241,834 B2 | 1/2016 | Chang et al. |
| 2001/0004644 A1 | 6/2001 | Levin |
| 2001/0005785 A1 | 6/2001 | Sachse |
| 2001/0034530 A1 | 10/2001 | Malackowski et al. |
| 2002/0006961 A1 | 1/2002 | Katz et al. |
| 2002/0013548 A1 | 1/2002 | Hinchliffe |
| 2002/0055746 A1 | 5/2002 | Burke et al. |
| 2002/0068851 A1 | 6/2002 | Gravenstein et al. |
| 2002/0077593 A1 | 6/2002 | Perkins et al. |
| 2002/0090388 A1 | 7/2002 | Humes et al. |
| 2002/0161389 A1* | 10/2002 | Boyle .............. A61F 2/013 606/200 |
| 2003/0013985 A1 | 1/2003 | Saadat |
| 2003/0017111 A1 | 1/2003 | Rabito |
| 2003/0018291 A1 | 1/2003 | Hill et al. |
| 2003/0040697 A1 | 2/2003 | Pass et al. |
| 2003/0051733 A1* | 3/2003 | Kotmel .............. A61B 5/055 128/207.14 |
| 2003/0073900 A1 | 4/2003 | Senarith et al. |
| 2003/0074045 A1* | 4/2003 | Buzzard ............ A61F 2/95 623/1.11 |
| 2003/0083608 A1 | 5/2003 | Evans et al. |
| 2003/0114732 A1 | 6/2003 | Webler et al. |
| 2003/0163154 A1 | 8/2003 | Miyata et al. |
| 2003/0220551 A1 | 11/2003 | Kimball et al. |
| 2004/0015150 A1 | 1/2004 | Zadno-Azizi |
| 2004/0018980 A1 | 1/2004 | Gurney et al. |
| 2004/0020492 A1 | 2/2004 | Dubrul et al. |
| 2004/0034311 A1 | 2/2004 | Mihalcik |
| 2004/0043052 A1 | 3/2004 | Hunter et al. |
| 2004/0058992 A1 | 3/2004 | Marinello et al. |
| 2004/0064105 A1 | 4/2004 | Capes et al. |
| 2004/0116958 A1 | 6/2004 | Gopferich et al. |
| 2004/0127820 A1 | 7/2004 | Clayman et al. |

(56) References Cited

U.S. PATENT DOCUMENTS

| | | |
|---|---|---|
| 2004/0158229 A1 | 8/2004 | Quinn |
| 2004/0181175 A1 | 9/2004 | Clayman et al. |
| 2004/0193073 A1 | 9/2004 | DeMello et al. |
| 2004/0220516 A1 | 11/2004 | Solomon et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0267347 A1 | 12/2004 | Cervantes |
| 2005/0027249 A1 | 2/2005 | Reifart et al. |
| 2005/0038319 A1 | 2/2005 | Goldwasser et al. |
| 2005/0055077 A1 | 3/2005 | Marco |
| 2005/0059930 A1 | 3/2005 | Garrison et al. |
| 2005/0059931 A1 | 3/2005 | Garrison et al. |
| 2005/0089670 A1 | 4/2005 | Large |
| 2005/0107738 A1 | 5/2005 | Slater et al. |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0124856 A1 | 6/2005 | Fujikura et al. |
| 2005/0131316 A1 | 6/2005 | Flagle et al. |
| 2005/0143687 A1 | 6/2005 | Rosenblatt et al. |
| 2005/0182319 A1 | 8/2005 | Glossop |
| 2005/0228224 A1 | 10/2005 | Okada et al. |
| 2005/0234507 A1 | 10/2005 | Geske et al. |
| 2005/0244472 A1 | 11/2005 | Hughes et al. |
| 2005/0283221 A1 | 12/2005 | Mann et al. |
| 2006/0004323 A1 | 1/2006 | Chang et al. |
| 2006/0047261 A1 | 3/2006 | Joshi |
| 2006/0063973 A1 | 3/2006 | Makower et al. |
| 2006/0173382 A1 | 8/2006 | Schreiner |
| 2006/0189844 A1 | 8/2006 | Tien |
| 2006/0190022 A1 | 8/2006 | Beyar et al. |
| 2006/0211752 A1 | 9/2006 | Kohn et al. |
| 2006/0271024 A1 | 11/2006 | Gertner et al. |
| 2006/0284428 A1 | 12/2006 | Beadle et al. |
| 2007/0020196 A1 | 1/2007 | Pipkin et al. |
| 2007/0112358 A1 | 5/2007 | Abbott |
| 2007/0129751 A1 | 6/2007 | Muni et al. |
| 2007/0135789 A1 | 6/2007 | Chang et al. |
| 2007/0167682 A1 | 7/2007 | Goldfarb et al. |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0249896 A1 | 10/2007 | Goldfarb et al. |
| 2007/0269385 A1 | 11/2007 | Yun et al. |
| 2007/0282305 A1 | 12/2007 | Goldfarb et al. |
| 2007/0293727 A1 | 12/2007 | Goldfarb et al. |
| 2007/0293946 A1 | 12/2007 | Gonzales et al. |
| 2008/0015544 A1 | 1/2008 | Keith et al. |
| 2008/0033519 A1 | 2/2008 | Burwell et al. |
| 2008/0051804 A1 | 2/2008 | Cottler et al. |
| 2008/0097516 A1 | 4/2008 | Chang et al. |
| 2008/0103521 A1 | 5/2008 | Makower et al. |
| 2008/0119693 A1 | 5/2008 | Makower et al. |
| 2008/0125626 A1 | 5/2008 | Chang et al. |
| 2008/0132938 A1 | 6/2008 | Chang et al. |
| 2008/0172033 A1 | 7/2008 | Keith et al. |
| 2008/0183128 A1 | 7/2008 | Morriss et al. |
| 2008/0188803 A1 | 8/2008 | Jang |
| 2008/0188870 A1 | 8/2008 | Andre et al. |
| 2008/0195041 A1 | 8/2008 | Goldfarb et al. |
| 2008/0228085 A1 | 9/2008 | Jenkins et al. |
| 2008/0262508 A1 | 10/2008 | Clifford et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0030274 A1 | 1/2009 | Goldfarb et al. |
| 2009/0088728 A1 | 4/2009 | Dollar et al. |
| 2009/0156980 A1 | 6/2009 | Eaton et al. |
| 2009/0163890 A1 | 6/2009 | Clifford et al. |
| 2009/0187089 A1 | 7/2009 | Say et al. |
| 2009/0187098 A1 | 7/2009 | Makower et al. |
| 2009/0198216 A1 | 8/2009 | Muni et al. |
| 2009/0240112 A1 | 9/2009 | Goldfarb et al. |
| 2009/0240237 A1 | 9/2009 | Goldfarb et al. |
| 2009/0312745 A1 | 12/2009 | Goldfarb et al. |
| 2010/0030031 A1 | 2/2010 | Goldfarb et al. |
| 2010/0042046 A1 | 2/2010 | Chang et al. |
| 2010/0087811 A1 | 4/2010 | Herrin et al. |
| 2010/0114066 A1 | 5/2010 | Makower et al. |
| 2010/0174138 A1 | 7/2010 | Chang et al. |
| 2010/0174308 A1 | 7/2010 | Chang et al. |
| 2010/0198191 A1 | 8/2010 | Clifford et al. |
| 2010/0198247 A1 | 8/2010 | Chang et al. |
| 2010/0198302 A1 | 8/2010 | Shalev |
| 2010/0210901 A1 | 8/2010 | Makower et al. |
| 2010/0211007 A1 | 8/2010 | Lesch, Jr. et al. |
| 2010/0268245 A1 | 10/2010 | Chang et al. |
| 2010/0274188 A1 | 10/2010 | Chang et al. |
| 2010/0290244 A1 | 11/2010 | Nath |
| 2010/0298862 A1 | 11/2010 | Chang et al. |
| 2011/0004057 A1 | 1/2011 | Goldfarb et al. |
| 2011/0015482 A1 | 1/2011 | Carrillo, Jr. |
| 2011/0060214 A1 | 3/2011 | Makower |
| 2011/0112512 A1 | 5/2011 | Muni et al. |
| 2011/0166190 A1 | 7/2011 | Anderson et al. |
| 2012/0071710 A1 | 3/2012 | Gazdzinski |
| 2012/0071824 A1 | 3/2012 | Chang et al. |
| 2012/0136207 A1 | 5/2012 | Goldfarb et al. |
| 2012/0184983 A1 | 7/2012 | Chang et al. |
| 2012/0245419 A1 | 9/2012 | Makower et al. |
| 2012/0265094 A1 | 10/2012 | Goldfarb et al. |
| 2013/0231529 A1 | 9/2013 | John et al. |
| 2013/0245608 A1 | 9/2013 | Muni et al. |
| 2013/0261388 A1 | 10/2013 | Jenkins et al. |
| 2014/0200444 A1 | 7/2014 | Kim et al. |
| 2014/0296898 A1 | 10/2014 | Chang et al. |
| 2014/0330074 A1 | 11/2014 | Morriss et al. |
| 2014/0336575 A1 | 11/2014 | Muni et al. |
| 2014/0336693 A1 | 11/2014 | Goldfarb et al. |
| 2014/0350465 A1 | 11/2014 | Muni et al. |
| 2014/0364725 A1 | 12/2014 | Makower |
| 2015/0088188 A1 | 3/2015 | Muni et al. |
| 2015/0165175 A1 | 6/2015 | Evard et al. |
| 2015/0165176 A1 | 6/2015 | Makower et al. |
| 2015/0182735 A1 | 7/2015 | Chang et al. |
| 2015/0209055 A1 | 7/2015 | Chang et al. |
| 2015/0250992 A1 | 9/2015 | Morriss et al. |

FOREIGN PATENT DOCUMENTS

| | | |
|---|---|---|
| CN | 2151720 | 1/1994 |
| CN | 2352818 | 12/1999 |
| CN | 201005758 Y | 1/2008 |
| DE | 3202878 | 8/1983 |
| DE | 4032096 | 4/1992 |
| DE | 4406077 | 9/1994 |
| DE | 8810044 | 11/1998 |
| DE | 29923582 | 12/2000 |
| DE | 10104663 | 8/2002 |
| DE | 10105592 | 8/2002 |
| EP | 129634 | 1/1985 |
| EP | 0200430 | 11/1986 |
| EP | 257605 | 3/1988 |
| EP | 355996 | 2/1990 |
| EP | 418391 | 3/1991 |
| EP | 427852 | 5/1991 |
| EP | 0515201 | 11/1992 |
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 0920882 | 6/1999 |
| EP | 0974936 | 1/2000 |
| EP | 1042998 | 10/2000 |
| EP | 1086664 | 3/2001 |
| EP | 1112103 | 7/2001 |
| EP | 1166710 | 1/2002 |
| EP | 1413258 | 4/2004 |
| EP | 1944053 | 7/2008 |
| FR | 2662083 | 11/1991 |
| FR | 2859377 | 3/2005 |

(56) References Cited

FOREIGN PATENT DOCUMENTS

| | | |
|---|---|---|
| FR | 2916144 | 11/2008 |
| GB | 2125874 | 3/1984 |
| GB | 2305174 | 4/1997 |
| JP | 53-67935 | 6/1978 |
| JP | 10-24098 | 1/1989 |
| JP | 10-34376 | 2/1989 |
| JP | 3-503011 | 7/1991 |
| JP | 3-504935 | 10/1991 |
| JP | 4-221313 | 8/1992 |
| JP | 4-224766 | 8/1992 |
| JP | 5-503650 | 6/1993 |
| JP | 5-211985 | 8/1993 |
| JP | H6-017751 | 3/1994 |
| JP | 6-277296 | 10/1994 |
| JP | 7-327916 | 12/1995 |
| JP | 8-317989 | 12/1996 |
| JP | 10-094543 | 4/1998 |
| JP | 11-507251 | 6/1999 |
| JP | 2000-501634 | 2/2000 |
| JP | 2000-126303 | 5/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-507140 | 2/2003 |
| JP | 2003-062080 | 3/2003 |
| JP | 2003-521327 | 7/2003 |
| JP | 2004-049583 | 2/2004 |
| JP | 4-224766 | 8/2004 |
| JP | 2004-357728 | 12/2004 |
| JP | 2005-323702 | 11/2005 |
| JP | 2005-532869 | 11/2005 |
| JP | 2008-539031 | 11/2008 |
| RU | 2108764 | 4/1998 |
| RU | 2213530 | 10/2003 |
| SU | 1662571 | 7/1991 |
| WO | WO 90/11053 | 10/1990 |
| WO | WO 90/14865 | 12/1990 |
| WO | WO 91/17787 | 11/1991 |
| WO | WO 92/15286 | 9/1992 |
| WO | WO 92/22350 | 12/1992 |
| WO | WO 94/12095 | 6/1994 |
| WO | WO 94/21320 | 9/1994 |
| WO | WO 95/02430 | 1/1995 |
| WO | WO 96/29071 | 9/1996 |
| WO | WO 97/21461 | 6/1997 |
| WO | WO 98/55174 | 12/1998 |
| WO | WO 99/00064 | 1/1999 |
| WO | WO 99/24106 | 5/1999 |
| WO | WO 99/26692 | 6/1999 |
| WO | WO 99/30655 | 6/1999 |
| WO | WO 99/32041 | 7/1999 |
| WO | WO 99/59649 | 11/1999 |
| WO | WO 00/09190 | 2/2000 |
| WO | WO 00/09192 | 2/2000 |
| WO | WO 00/23009 | 4/2000 |
| WO | WO 00/51672 | 9/2000 |
| WO | WO 00/53252 | 9/2000 |
| WO | WO 00/67834 | 11/2000 |
| WO | WO 01/05462 | 1/2001 |
| WO | WO 01/45572 | 6/2001 |
| WO | WO 01/54558 | 8/2001 |
| WO | WO 01/56481 | 8/2001 |
| WO | WO 01/68178 | 9/2001 |
| WO | WO 01/70325 | 9/2001 |
| WO | WO 01/74266 | 10/2001 |
| WO | WO 01/82800 | 11/2001 |
| WO | WO 01/97895 | 12/2001 |
| WO | WO 02/062269 | 8/2002 |
| WO | WO 02/089899 | 11/2002 |
| WO | WO 03/049603 | 6/2003 |
| WO | WO 03/063703 | 8/2003 |
| WO | WO 03/105657 | 12/2003 |
| WO | WO 2004/006788 | 1/2004 |
| WO | WO 2004/018980 | 3/2004 |
| WO | WO 2004/026391 | 4/2004 |
| WO | WO 2004/045387 | 6/2004 |
| WO | WO 2004/058045 | 7/2004 |
| WO | WO 2004/082525 A2 | 9/2004 |
| WO | WO 2004/082525 A3 | 9/2004 |
| WO | WO 2005/018730 | 3/2005 |
| WO | WO 2005/077450 | 8/2005 |
| WO | WO 2005/089670 | 9/2005 |
| WO | WO 2005/117755 | 12/2005 |
| WO | WO 2006/034008 | 3/2006 |
| WO | WO 2006/078884 | 7/2006 |
| WO | WO 2006/107957 | 10/2006 |
| WO | WO 2006/116597 | 11/2006 |
| WO | WO 2006/118737 | 11/2006 |
| WO | WO 2006/135853 | 12/2006 |
| WO | WO 2007/034203 | 3/2007 |
| WO | WO 2007/035204 | 3/2007 |
| WO | WO 2007/111636 | 10/2007 |
| WO | WO 2007/124260 | 11/2007 |
| WO | WO 2008/036149 | 3/2008 |
| WO | WO 2008/045242 | 4/2008 |
| WO | WO 2008/051918 | 5/2008 |
| WO | WO 2008/134382 | 11/2008 |

OTHER PUBLICATIONS

Merriam-Webster definition of "lumen" as accessed Jun. 10, 2016; http://www.merriam-webster.com/dictionary/lumen.*
Argon Medical. Maxxim Medical. Ad for Sniper EliteTM Hydrophilic Ni—Ti Alloy Guidewire (2001).
Aust, R., et al. 'The Functional Size of the Human Maxillary Ostium in Vivo' Acta. Otolaryn. (9178) vol. 78 pp. 432-435.
Baim, D.S., MD 'Grossman's Cardiac Catheterization, Angiography, and Intervention' (2000) Lippincott Williams & Wilkins pp. 76, 84 & 214.
Barrett, S. 'Be Wary of Neurocranial Restructuring (NCR)' Chirobase; Jul. 2003; www.chirobase.org/06DD/ncr.html.
Bartal, N. 'An Improved stent for Use in the Surgical Management of Congential Posterior Choanal Atresia' J. Laryngol. Otol (1988) vol. 102 pp. 146-147.
Becker, A.E. 'Restenosis After Angioplasty' The Lancet (1988) vol. 331, No. 8584 p. 532.
Bellis, M. History of the Catheter—Balloon Catherter—Thomas Fogarty. www.inventors.about.com/library/inventors/blcatheter.htm?p=1
Benninger et al.; Adult Chronic Rhinosinusitis: Definitions, Diagnosis, Epidemiology, and Pathophysilogy' Arch Otolarygol Head and Neck Surg. vol. 129 (Sep. 2003) pp. A1-S32.
Bent et al. 'The Frontal Cell as a Cause of Frontal Sinus Obstruction' Amercian Journal of Rhinology, vol. 8, No. 4 (1994) pp. 185-191.
Binner et al. 'Fibre-Optic Transillunination of the Sinueses: A Comparison of the Value of Radiography and Transillumination in Antral Disease'Clinical Otolaryngology. vol. 3 (1978) pp. 1-11.
Brown, C.L. et al., 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.
Casiano et al. 'Endoscopic Lothrop Procedure: the University of Miami Experience' American Journal of Rhinology, vol. 12, No. 5 (1998) pp. 335-339.
Casserly, I.P. et al., Chapter 7. 'Guides and Wires in Percutaneous Coronary Intervention' Strategic Approaches in Coronary Intervention (2006) Lippincott Williams & Wilkins pp. 91-99.
Chien, Y.W. et al. 'Nasal Systemic Drug Delivery' Drugs and Pharmaceutical Sciences, vol. 39, pp. 60-63.
Cohen et al. 'Endoscopic Sinus Surgery: Where we are and where we're going ' Current Opinion in Otolaryngology & Head and Neck Surgery, vol. 13 (2005) pp. 32-38.
Colla, A. et al., 'Trihaloacetylated Enol Ethers—General Synthetic Procedure and Heterocyclic Ring Closure Reactions with Hydroxylamine' Synthesis, (Jun. 1991) pp. 483-486.

(56) References Cited

OTHER PUBLICATIONS

Costa, M.N. et al. 'Endoscopic Study of the Intranasal Ostium in External Dacryocystorhinostomy Postoperative. Influences of Saline Solution and 5-Flurorouracil' Clinics (2007) vol. 62, Issue1, pp. 41-46.

Cussler, E.L. 'Diffusion: Mass transfer in Fluid Systems' Cambridge University Press (1996).

Davis, G.E. et al. 'A Complication from Neurocranial Restructuring' Arch Otolaryngol Head Neck Surg. vol. 129 (Apr. 2003) pp. 472-474.

Deutschmann, R. et al. 'A Contribution of the Topical Treatment of [Maxillary] Sinusitis Preliminary Communication' Stomat DDR 26, (1976) pp. 585-592.

Domb, A. et al. 'Handbook of Biodegradable Polymers' Harwood Academic Publishers (1997)

Doyle Nasal Splints, Jan. 25, 2007; www.doylemedical.com/nasalsplints.htm.

Draf, W. 'Endonasal Micro-Endoscopic Frontal Sinus Surgery: the Fulda Concept' Op Tech Otolaryngol Head Neck Surg. vol. 2 (1991) pp. 234-240.

Edmond, C. et al. 'ENT Surgical Stimulator' Nov. 1989.

ENT Checklist; Physical Examination Performance Checklist [date of publication unknown].

Eremychev, V.A. 'Needles for Puncture and Drainage of the Maxillary Sinus' Meditsinskaya Tekhnika, No. 5 (1974) pp. 54.55.

Feldman, R.L. et al., 'New Steerable, Ultra-Low-Profile, Fixed Wire Angioplasty Catheter: Initial Experience With the Cordis OrionTM Steerable PTCA Balloon Catheter' Cathet. Cardiovasc. Diagn. (1990) vol. 19, No. 2 pp. 142-145.

Ford, C.N. 'A Multipurpose Laryngeal Injector Device' Otolaryngol. Head Neck Surg. (1990) vol. 103, No. 1 pp. 135-137.

Friedman, M., M.D., et al. 'Frontal Sinus Surgery: Endoscopic Technique' Operative Techniques in Otolarynology—Head and Neck Surgery. vol. 12, No. 2 (Jun. 2001) pp. 60-65.

Friedman, et al. 'Intraoperative and Postoperative Assessment of Frontal Sinus Patency by Transillumination' Laryngoscope. vol. 110 (Apr. 2000) pp. 683-684.

Friedman, et al. 'Middle Turbinate Medialization and Preservation in Endoscopic Surgery' Otolaryngology—Head and Neck Surgery. (2000) vol. 123, No. 1, part 1, pp. 76-80.

Fung, M.K.T. 'Template for Frontal Osteoplastic Flap' Laryngoscope. vol. 96 (1986) pp. 578-579.

Gatot, A. et al. 'Early treatment of Orbital Floor Fractures with Catheter Balloon in Children' Int J. Pediatric Otorhinolaryngol (1991) vol. 21 pp. 97-101.

Gerus, I.I. et al. 'β-Ethoxyvinyl Polyflurorolkyl Ketones—Versatile Synthones in Fluoroorganic Chemistry' Journal of Fluorine Chemistry. vol. 69 (1994) pp. 195-198. Elesvier Science S.A.

Good, R.H. 'An Intranasal Method for Opening the Frontal Sinus Establishing the Largest Possible Drainage' Laryngoscope. vol. 18 (1908) pp. 266-274.

Gopferich 'Polymer Degradation and Erosion: Mechanisms and Application' Eur. J. Parm. Biophar. vol. 42 (1996) pp. 1-11.

Gorlov, D.V. et al. 'Acylation of 2-Methoxypropene with Anhydrides and Halides of Perflurocarboxylic Acids in the Presence of Teriary Amines' Russian Chemical Bulletin. vol. 48 No. 9 (Sep. 1999) pp. 1791-1792. Kluwer Academic/Plenum Publishers.

Gottmann, et al. 'Balloon Dilatation in the Nasal Cavity and Paranasal Sinuses' CIRSE. (Sep. 25, 2004) pp. 1-27.

Gottmann, et al. 'Balloon Dilatation of Recurrent Ostial Occlusion of the Frontal Sinus' CIRSE Abstract (Mar. 2001) B-04353.

Gottmann, et al., Balloon Dilatation of Recurrent Ostial Occlusion of the Front Sinus' OASIS-Online Abstract Submission and Invitation System, 1996-2006, Coe Truman Technologies, Inc.

Gottmann, et al. 'Successful Treatment of Recurrent Post-Operative Frontal Sinus Stenoses by Balloon Dilatation' CIRSE. (Oct. 5, 2002)

Gottmann, D. 'Treatment of Stenoses of Upper Air Routes by Balloon Dilation' Proceeding of the 83rd Annual Convention of Association of West German ENT Physicians (1999).

Gupta, D. et al., 'Dacrystitis Secondary to an Iatrogenic Foreign Body in Lacrimal Apparatus' Ear, Nose & Throat Journal (2009) www.findarticles.com/p/articles/mi_mOBUM/is_7_88/ai_n32428620/.

Hashim, et al. 'Balloon Compression of the Intermaxillary Sinus for Intractable Post Traumatic Bleeding from the Maxillary Artery' Scandinavian Journal of Plastic reconstruction Sergery and Hand Surgery (1999) vol. 33 pp. 321-324.

Hojo, M. et al, 'Electrophilic Substiutions of Olefinic Hydrogens II. Acylation of Vinyle Ethers and N Vinyl Amides Chemistry Letters' (1976) pp. 499-502. Chemical Society of Japan.

Hopf, J.U.G. et al. 'Minature Endoscopes in Otorhinolaryngologic Applications' Min Invas Ther & Allied Technol. (1998) vol. 7, No. 3 pp. 209-218.

Hosemann, W. et al. A Dissection Course on Endoscopic Endonasal Sinus Surgery (2005) Endo-Press, Tuttlingen pp. 4-37.

Hosemann, W. et al. 'Endonasal Frontal Sinusotomy in Surgical Management of Chronic Sinusitis: A Critical Evaluation' American Journal of Rhinology. vol. 11, No. 1 (1997) pp. 1-9.

Hosemann, M.E. et al. 'Experimentelle Untersuchungen sur Wundheilung in den Nasennebenholhlen. II. Spontaner Wundschluss und medikamentose Effekte im standardisierten Wundmodell.' HNO 39 (1991) pp. 48-54. 'Experimental investigations on wound healing of the paranasal sinuses. II. Spontaneous wound closure and pharmacological effects in a standardized animals.' HNO 39 (1991) pp. 48-54.

Hosemann, W.G. et al. 'Minimally Invasive Endonasal Sinus Surgery' Thieme, Stuttgart, New York (2000).

Hosemann, M.E. et al. 'Normal Wound Healing of the Paranasal Sinuses—Clinical and Experimental Investigations' Eur Arch Otorhinolaryngol. vol. 248, (1991) pp. 390-394.

Hosemann, W. et al. 'Behandlung nach Nasennebenhohleneingriffen, part 2: Theapeutische Maβnahem' HNO akutell 7 (1999) pp. 291-302.

Hospital Corpsman Sickcall Screener's Handbook. Naval Hospital Great Lakes (Apr. 1999) www.brooksidepress.org/Products/Operationa.Medicine/DATA. 2001 pp. 1-6.

Hybels, R.L. 'Transillumination Durning Osteoplastic Frontal Sinusotomy' The Laryngoscope. vol. 91 (Sep. 1981) pp. 1560.

Ijaduola, T.G.A. 'Use of a Foley Catheter for Short-Term Drainage in Frontal Sinus Surgery' Ther Journal of Laryngology and Otology. (1989) vol. 103. pp. 375.378.

Ingals, E.F. 'New Operation and Instruments for Drainage the Frontal Sinus' Ann. Otol. Rhinol. Layyngol. vol. 14 (1905) pp. 644-649.

Iro, H. et al., 'A New Device for Frontal Sinus Endoscopy: First Clinical Report' Otolaryngol. Head Neck Surg. (2001) vol. 125 No. 6 pp. 613-616.

Jacobs, J.B. '100 Years of Frontal Sinus Surgery' Laryngoscope. vol. 107 (1997) pp. 1-36.

K-Splint Internal Nasal Splints; Jan. 25, 2007; www.invotec.net/rhinology/ksplint.html.

Kaiser, H. et al 'Cortizontherapie, Corticoide in Klinik and Praxis' Thieme, Stuggart (1992) pp. 390-401.

Kennedy, D.W., M.D. et al. 'Diseases of the Sinuses: Diagnosis and Management' (Copyright 2001) by B.C. Decker Inc.

Khomutov, S.M. et al. 'Dissolution of a Mixture of Steroids in Cyclodextrin Solutions: a Model Description' Pharmaceutical Chemistry Journal. vol. 35, No. 11 ( Nov. 2001) pp. 627-629.

Kingdom, T.T. et al. 'Image-Guided Surgery of the Sinuses: Current Technology and Applications' Otolaryngol. Clin. North Am. vol. 37, No. 2 (Apr. 2004) pp. 381-400.

Klossek, J.M. et al. 'Local Safety of Intranasal Trimcinolone Acentonide: Clinical and Histological Aspects of Nasal Mucosa in the Long-Term Treatment of Perennial Allergic Rhinitis' Rhinology. vol. 39, No. 1 (2001) pp. 17-22.

Kozlov et al. 'Diagnosis and Treatment of Sinusitis by YAMIK Sinus Catheters' Rhinology (1996) vol. 34, pp. 123-124.

Kuhn, et al. 'The Agger Nasi Cell in Frontal Recess Obstruction: An Anatomic, Radiology and Clinical Correlation' Operative Techniques in Otolaryngology-Head and Neck Surgery. vol. 2, No. 4 (1991) pp. 226-231.

(56) References Cited

OTHER PUBLICATIONS

Laliberte, F. et al. 'Clinical and Pathologic Methods to Assess the Long-Term Safety of Nasal Corticosteroids' Allergy. vol. 55, No. 8 (2000) pp. 718-722.
Lang, E.V., et al., 'Access Systems for Puncture at an Acute Angle' J. Vasc. Interv. Radiol. (1995) vol. 6, No. 5 pp. 711-713.
Lanza, D.C. 'Postoperative Care and Avoiding Frontal Recess Stenosis' Internatinal Advanced Sinus Symposium (1993) Jul. 21-24.
Large, G.C. 'Crystalline Tetracycline Hydrochloride in the Treatment of Acute and Chronic Maxillary Sinusitis' Canad. M.A.J. (1958) vol. 79 pp. 15-16.
Lund, V.J. 'Maximal Medical Therapy for Chronic Rhinosinusitis' Otolaryngol Clin N. Am. vol. 38 (2005) pp. 1301-1310.
Maran, A.G.D. et al. 'The Use of the Foley Balloon Catheter in the Tripod Fracture' J. Laryngol. Otol. (1971) vol. 85, Issue 9, pp. 897-902.
May, M. et al. 'Frontal Sinus Surgery: Endonasal Drainage Instead of an External Osteopolstic Approach' Op Tech Otolaryngo Head Neck Surgery. 6 (1995) pp. 184-192.
Medtronic, xomed.com-MicroFrance Catalog Browser. www.xomcat.com/xomfrance/index.php?zone=both&cat=18&sub=58&prodline=1272 I (Dec. 31, 2003) pp. 1-2.
Mehan, V.K. et al., 'Coronary Angioplasty through 4 French Diagnostic Catheters' Cathet. Cardiovasc. Diagn. (1993) vol. 30, No. 1 pp. 22-26.
Mellor, J.M. et al 'Synthesis of Trifluromethylnaphthalenes' Tetrahedron. vol. 56 (2000) pp. 10067-10074. Elsevier Science Ltd.
Metson, R., et al., 'Endoscopic Treatment of Sphenoid Sinusitis' Otolaryngol. Head Neck Surg. (1996) vol. 114, No. 6 pp. 736-744.
Metson, R. 'Holmium: YAG Laser Endoscopic Sinus Surgery: A Randomized Controlled Study' Laryngoscope. vol. 106, Issue 1, Supplement 77 (Jan. 1996) pp. 1-18.
Miller, et al. 'Management of Fractures of the Supraorbital Rim' Journal of Trauma. vol. 18, No. 7 (Jul. 1978) pp. 507-512.
Min, Y-G et al. 'Mucociliary Activity and Histopathology of Sinus Mucosa in Experimental Maxilary Sinusitis: A Comparison of Systemic Administration of Antibiotic and Antibiotic Delivery by Polylactic Acid Polymer' Laryngoscope. vol. 105 (Aug. 1995) pp. 835-842.
Mols, B. 'Movable Tool Tip for Keyhole Surgery' Delft Outlook, vol. 3 (2005) pp. 13-17.
Mooney, M.R., et al., 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.
Moriguchi, T. et al. 'Additional-Elimination Reaction in the Trifluoroacetylation of Electron-Rich Olefins' J. Org. Chem. vol. 60, No. 11 (1995) pp. 3523.3528. American Chemical Society.
Nasal Surgery and Accessories, Jan. 25, 2007; www.technologyforlife.com.au/ent/nasal.html.
Park, K. et al. 'Biodegradable Hydrogels for Durg Delivery' (1993) Technomic Publishing Inc. Lancaster.
Piccirillo, J.F. et al. 'Physchometric and Clinimetric Validity of the 20-Item Sino-Nasal Outcome test (SNOT-20)' Copyright 1996 Washington University, St. Louis, MO.
Piers, et al. 'A Flexible Distal Tip with Two Degrees of Freedon for Enhanced Dexterity in Endoscopic Robot Surgery' Proceedings 13th Micromechanics Europe Workshop (2002) pp. 271-274.
Podoshin, L et al. 'Balloon Technique for Treatment of Frontal Sinus Fractures' The journal of Laryngology & Otology (1967), vol. 81. pp. 1157-1161.
Pownell, P.H. et al., 'Diagnostic Nasal Endoscopy' plastic & Reconstructive Surgery (1997) vol. 99, Iss5 pp. 1451-1458.
Prince, et al. 'Analysis of the Intranasal Distribution of Ointment' J Otolaryngol. vol. 26 (1997) pp. 357-360.
Ramsdale, D.R., Illustrated Coronary Intervention: A case-oriented approach, (2001) Martin Dunitz Ltd. pp. 1-5.
Ritter, F.N. et al., Atlas of Paranasal Sinus Surgery (1991) Igaku-Shoin Medical Pub. pp. 1-81.
Robison, J. Mathews, M.D. 'Pressure Treatment of Maxillary Sinusitis' J.A.M.A. May 31, 1952) pp. 436-440.
Robison, J. Mathews, M.D. 'Pressure Treatment of Purulent Maxillary Sinusitis' Texas State Journal of Medicine (May 1952) pp. 281-288.
St. Croix et al. 'Genes Expressed in Human Tumor Endothelium' Science, vol. 289 (May 15, 2000) pp. 1197-1202.
Sama, A., et al., 'Current Opinions on the Surgical Management of Frontal Sinus Disease' ENT News. www.pinpointmedical.com/ent-news (2009) vol. 17, No. 6 pp. 60-63.
Sanborn, T.A. et al., 'Percutaneous Endocardial Transfer and Expression of Genes to the Myocardium Utilizing Fluropscopic Guidance' Catheter Cardiovasc. Interv. (2001) vol. 52, No. 2 pp. 260-266.
Sawbones Catalog 2001, Pacific Research Laboratories, Inc., Vashon Washington 98070 USA.
Saxon, R.R. et al., 'Technical Aspects of Accessing the Portal Vein During the TIPS Procedure' J. Vasc. Interv. Radiol. (1997) vol. 8, No. 5 pp. 733-744.
Schaefer, S.D., M.D. 'Rhinology and Sinus Disease: A Problem-Oriented Approach' (Copyright 1988) by Mosby, Inc.
Schneider. Pfizer Ad for Softip [date of publication unknown].
Shah, N.J. et al., 'Endoscopic Pituitary Surgery—A Beginner's Guide' Indian Journal of Otolaryngology and Head and Neck Surgery (2004) vol. 56, No. 1 pp. 71-78.
Shah, N.J. 'Functional Endoscopic Sinus Surgery' (1999); found at bhj.org/journa1/1999_4104_oct99/sp_659.htm.
Single-Pole and Multi-Pole Lightguides for UV Spot Light Curing Systems.
Sinusitis, Maxillary, Acute Surgical Treatment. Http://www.emedicine.com/ent/topic340.htm. Aug. 29, 2006. pp. 1-11.
Sobol, et al. 'Sinusitis, Maxillary, Acute Surgical Treatment.' eMedicine. Retrieved from the Internet: <<http://emedicine.medscape.com/article/862030-print>> (Nov. 16, 2010) pp. 1-11.
Stammberger, H. 'Komplikationen entzundlicher Nasennebenhohlenerkrankungen eischließ iatrogen bedingter Komplikationen' Eur Arch Oti-Rhino-Laryngol Supple. (Jan. 1993) pp. 61-102.
Stammberger, et al. Chapter 3 'Special Endoscopic Anatomy of the Lateral Nasal Wall and Ethmoidal Sinuses' Functional Endoscopic Sinus Surgery. (1991) Ch. 3, pp. 49-87.
Strohm, et al. Die Behandlung von Stenosen der oberen Luftwege mittels rontgenologisch gesteuerter Ballondilation (Sep. 25, 1999) pp. 1-4.
Strohm, et al 'Le Traitement Des Stenoses Voies Aeriennes Superieures Par Dilation Ay Balloon' Sep. 25, 1999.
Strohm, et al. 'Treatment of Stenoses of the Upper Airways by Balloon Dilation' Sudwestdeutscher Abstract 45 (Sep. 25, 1999) pp. 1-3.
SurgTrainer Product Information 2003, Surg Trainer, Ltd. Ibaraki, Japan.
SurgTrainer Product Information 'Incisive Human Nasal Model for ESS Training' Surg Trainer, Ltd. Ibaraki, Japan (2004) www1.accsnet.ne.jp/~juliy/st/en/partslist.html.
Tabor, M.H. et al., 'Symptomatic Bilateral Duct Cysts in a Newborn—Rhinoscopic Clinic' Ear, Nose & Throat Journal (2003) www.findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinoloaringol. vol. 6 (1978) pp. 45-47.
Terumo. Medi-Tech. Boston Scientific. (1993) Ad of Glidewire.
The Operating Theatre Journal (www.otjonline.com) 'Disposable Medical Device for Wound Disclosure/The Tristel Purple Promotion—A Collaboration between Tristel PLC and Karl Storz Ednoscopy (UK) Ltd.' p. 4.
Weber, R. et al. 'Endonasale Stirnhohlenchirugie mit Langzeiteinlage eines I Platzhalters' Laryngol. Rhinol. Otol. vol. 76 (1997) pp. 728-734. (English Abstract).
Weber, R. et al., 'Videoendoscopic Analysis of Nasal Steriod Distribution' Rhinology. vol. 37 (1999) pp. 69-73.

(56) References Cited

OTHER PUBLICATIONS

Weiner, R.I., D.O., et al., 'Development and Application of Transseptal Left Heart Catheterization' Cathet. Cardiovasc. Diagn. (1988) vol. 15, No. 2, pp. 112-120.
Wiatrak, B.J., et al., 'Unilateral Choanal Atresia: Initial Presentation and Endoscopic Repair' International Journal of Pediatric Otorhinolaryngology (1998) vol. 46, pp. 27-35.
Woog, et al. 'Paranasal Sinus Endoscopy and Orbital Fracture Repair' Arch Ophthalmol. vol. 116 (May 1998) pp. 688-691.
Wormald, P.J., et al., 'The 'Swing-Door' Technique for Uncinectomy in Endoscopic Sinus Surgery' The Journal of Laryngology and Otology (1998) vol. 112, pp. 547-551.
Xomed-Treace. Bristol-Myers Squibb. Ad for Laser Shield II. Setting the Standards for Tomorrow. [date of publication unknown].
Yamauchi, Y. et al., 'Development of a Silicone Model for Endoscopic Sinus Surgery' Proc International Journal of Computer Assisted Radiology and Surgery vol. 99 (1999) p. 1039.
Yamauchi, Y., et al., 'A Training System for Endoscopic Sinus Surgery with Skill Evaluation' Computer Assisted Radiology and Surgery (2001) with accompanying copy of poster presentation.
Yanagisawa et al. 'Anterior and Posterior Fontanelles.' Ear, Nose & Throat Journal (2001) vol. 80. pp. 10-12.
Zimarino, M., M.D., et al., 'Initial Experience with the EuropassTM: A new Ultra-Low Profile monorail Balloon Catheter' Cathet. Cardiovasc. Diagn. (1994) vol. 33, No. 1, pp. 76-79.
Australian Office Action, Examiners First Report dated Apr. 8, 2010 for Application No. AU 2005274794.
Chinese Office Action, First Office Action dated Nov. 5, 2012 for CN 200980137396.1.
Chinese Search Report dated Oct. 29, 2012 for Application No. CN 200980137396.1.
Chinese Search Report dated Jan. 11, 2013 for Application No. CN 200980152995.0.
Chinese Office Action, First Office Action dated Jan. 29, 2013 for CN 200980152995.1.
European Communication dated Sep. 4, 2008 for Application No. EP 05773189.
European Communication dated Jun. 19, 2009 for Application No. EP 05773189.
European Communication dated Aug. 1, 2012 for Application No. EP 06784759.0.
European Communication dated Aug. 24, 2012 for Application No. EP 05798331.4.
European Communication dated Nov. 9, 2012 for Application No. EP 07750248.2.
European Communication dated Apr. 19, 2012 for Application No. EP 08746715.5.
European Communication dated Jan. 7, 2013 for Application No. EP 08746715.5.
European Communication dated Apr. 11, 2013 for Application No. EP 05778834.1.
European Communication dated May 10, 2013 for Application No. EP 06751637.7.
European Exam Report dated Feb. 22, 2006 for Application No. EP 02716734.5.
European Exam Report dated Feb. 8, 2007 for Application No. EP 02716734.5.
European Search Report and Written Opinion dated Sep. 11, 2009 for Application No. EP 06815174.
European Search Report dated Mar. 16, 2010 re Application No. EP 06718986.
European Search Report dated Sep. 27, 2011 for Application No. EP 10182961.
European Search Report dated Sep. 29, 2011 for Application No. EP 10182893.
European Search Report dated Jul. 23, 2012 for. Application No. EP 12162709.
European Search Report dated Jul. 24, 2012 for Application No. EP 12162712.
European Search Report dated Aug. 31, 2012 for Application No. EP 12173295.
European Search Report dated Oct. 10, 2012 for Application No. EP 12175607.
European Search Report dated Nov. 22, 2012 for Application No. EP 12182993.
European Search Report dated Dec. 5, 2012 for Application No. EP 12182998.
European Search Report dated Jan. 9, 2013 for Application No. EP 12183000.
European Search Report dated Jan. 11, 2013 for Application No. EP 12183002.
European Search Report dated Aug. 13, 2013 for Application No. EP 13172140.
European Search Report dated Sep. 9, 2013 for Application No. EP 13179223.
Partial European Search Report dated Sep. 20, 2007 for Application No. EP 07252018.
Partial European Search Report dated Mar. 25, 2008 for Application No. EP 07252018.
Supplemental Partial European Search Report dated Jun. 2, 2008 for Application No. EP 05773189.
Supplemental Partial European Search Report dated Jul. 1, 2009 for Application No. EP 06815285.
Supplemental Partial European Search Report dated Nov. 19, 2010 for Application No. EP 06751637.
Supplemental European Search Report dated Jan. 29, 2010 for Application No. EP 07836108.
Supplemental European Search Report dated Feb. 2, 2010 for Application No. EP 07836109.
Supplemental European Search Report dated Feb. 17, 2010 for Application No. EP 07836110.
Supplemental European Search Report dated Mar. 1, 2010 for Application No. EP 05778834.
Supplemental European Search Report dated Mar. 16, 2010 for Application No. EP 06718986.
Supplemental European Search Report dated Jun. 22, 2010 for Application No. EP 06784759.
Supplemental European Search Report dated Sep. 23, 2010 for Application No. EP 08746715.
Supplemental European Search Report dated Jan. 28, 2011 for Application No. EP 07777004.
Supplemental European Search Report dated Mar. 31, 2011 for Application No. EP 05798331.
Supplemental European Search Report dated Aug. 30, 2011 for Application No. EP 06800540.
Supplemental European Search Report dated Sep. 29, 2011 for Application No. EP 07750248.
PCT Search Report dated Nov. 30, 2009 for Application No. UPCT/US2009/057203.
International Preliminary Report on Patentability dated Aug. 7, 2006 for Application No. PCT/US05/25371.
International Preliminary Report on Patentability and Written Opinion dated Sep. 25, 2007 for Application No. PCT/US06/002004.
International Preliminary Report on Patentability dated Feb. 15, 2008 for Application No. PCT/US05/13617.
International Preliminary Report on Patentability and Written Opinion dated Nov. 18, 2008 for Application No. PCT/US07/11449.
International Preliminary Report on Patentability and Written Opinion dated Apr. 7, 2009 for Application No. PCT/US07/021170.
International Preliminary Report on Patentability and Written Opinion dated May 5, 2009 for Application No. PCT/US06/036960.
International Preliminary Report on Patentability and Written Opinion dated Oct. 13, 2009 for Application No. PCT/US08/059786.
International Preliminary Report on Patentability and Written Opinion dated Oct. 27, 2009 for Application No. PCT/US08/061343.
International Preliminary Report on Patentability dated Jun. 29, 2011 for Application No. PCT/US2009/069143.
International Search Report dated Jun. 3, 2002 for Application No. PCT/EP02/01228.
International Search Report and Written Opinion dated Apr. 10, 2006 for Application No. PCT/US05/25371.

(56) References Cited

OTHER PUBLICATIONS

International Search Report dated May 8, 2007 for Application No. PCT/US2006/16026.
International Search Report dated Aug. 17, 2007 for Application No. PCT/US05/013617.
International Search Report dated Aug. 29, 2007 for Application No. PCT/US06/002004.
International Search Report dated Sep. 25, 2007 for Application No. PCT/US06/037167.
International Search Report dated Oct. 19, 2007 for Application No. PCT/US07/003394.
International Search Report dated May 29, 2008 for Application No. PCT/US07/021170.
International Search Report dated May 29, 2008 for Application No. PCT/US07/021922.
International Search Report dated Jul. 1, 2008 for Application No. PCT/US06/022745.
International Search Report dated Jul. 3, 2008 for Application No. PCT/US2006/029695.
International Search Report dated Jul. 7, 2008 for Application No. PCT/US07/016213.
International Search Report dated Jul. 8, 2008 for Application No. PCT/US07/011474.
International Search Report dated Jul. 17, 2008 for Application No. PCT/US06/036960.
International Search Report and Written Opinion dated Jul. 21, 2008 for Application No. PCT/US05/033090.
International Search Report dated Aug. 25, 2008 for Application No. PCT/US2008/000911.
International Search Report dated Sep. 10, 2008 for Application No. PCT/US07/016212.
International Search Report and Written Opinion dated Sep. 12, 2008 for Application No. PCT/US07/16214.
International Search Report and Written Opinion dated Sep. 17, 2008 for Application No. PCT/US08/059786.
International Search Report and Written Opinion dated Sep. 17, 2008 for Application No. PCT/US08/061343.
International Search Report and Written Opinion dated Oct. 1, 2008 for Application No. PCT/US07/011449.
International Search Report dated Oct. 15, 2008 for Application No. PCT/US2008/061048.
International Search Report dated Nov. 30, 2009 for Application No. PCT/US2009/057203.
International Search Report dated Dec. 10, 2009 for Application No. PCT/US2009/052236.
International Search Report dated Dec. 16, 2009 for Application No. PCT/US2009/050800.
International Search Report dated Mar. 31, 2010 for Application No. PCT/US2009/069143.
International Search Report dated Jul. 8, 2010 for Application No. PCT/US2010/027837.
International Search Report and Written Opinion dated Oct. 6, 2010 for Application No. PCT/US2010/040548.
International Search Report dated Mar. 25, 2011 for Application No. PCT/US2010/062161.
International Search Report dated Mar. 28, 2011 for Application No. PCT/US2010/061850.
International Search Report dated Mar. 31, 2011 for Application No. PCT/US2010/060898.
International Search Report dated Mar. 31, 2011 for Application No. PCT/US2009/069143.
International Search Report dated Aug. 9, 2011 for Application No. PCT/US2011/038751.
International Search Report dated May 18, 2012 for Application No. PCT/US2011/052321.
Partial International Search Report dated Feb. 7, 2012 for Application No. PCT/US2011/052321.
Japanese Office Action, Examiner's Decision of Refusal dated Oct. 18, 2011 for Application No. JP 2007-509632.
Japanese Office Action, Notification of Reasons for Refusal dated Apr. 26, 2011 for Application No. JP 2007-532485.
Japanese Office Action, Notification of Reasons for Refusal dated Jan. 24, 2012 for Application No. JP 2007-532485.
Japanese Office Action, Notification of Reasons for Refusal dated Aug. 16, 2011 for Application No. JP 2008-516013.
Japanese Office Action, Notification of Reasons for Refusal dated Nov. 8, 2011 for Application No. JP 2008-524250.
Japanese Office Action, Notification of Reasons for Refusal dated Jun. 25, 2013 for Application No. JP 2012-131840.
Russian Office Action dated Sep. 28, 2012 for Application No. RU 2011130530.
Russian Office Action dated Mar. 19, 2013 for Application No. RU 2011130530.
U.S. Office Action dated Sep. 16, 2005 for U.S. Appl. No. 10/259,300.
U.S. Office Action dated Jul. 7, 2006 for U.S. Appl. No. 10/259,300.
U.S. Office Action dated Feb. 13, 2007 for U.S. Appl. No. 10/259,300.
U.S. Office Action dated Oct. 9, 2007 for U.S. Appl. No. 10/259,300.
U.S. Office Action dated Jan. 24, 2008 for U.S. Appl. No. 10/259,300.
U.S. Office Action dated Oct. 6, 2008 for U.S. Appl. No. 10/259,300.
U.S. Office Action dated May 29, 2007 for U.S. Appl. No. 10/912,578.
U.S. Office Action dated Nov. 14, 2007 for U.S. Appl. No. 10/912,578.
U.S. Office Action dated Dec. 10, 2007 for U.S. Appl. No. 10/912,578.
U.S. Office Action dated Oct. 18, 2007 for U.S. Appl. No. 11/037,548.
U.S. Office Action dated Dec. 6, 2007 for U.S. Appl. No. 11/037,548.
U.S. Office Action dated Apr. 9, 2008 for U.S. Appl. No. 11/037,548.
U.S. Office Action dated Nov. 28, 2007 for U.S. Appl. No. 11/234,395.
U.S. Office Action dated Sep. 12, 2008 for U.S. Appl. No. 10/829,917.
U.S. Office Action dated Nov. 17, 2008 for U.S. Appl. No. 10/829,917.
U.S. Office Action dated Mar. 18, 2009 for U.S. Appl. No. 10/829,917.
U.S. Office Action dated Nov. 9, 2009 for U.S. Appl. No. 10/829,917.
U.S. Office Action dated Oct. 29, 2008 for U.S. Appl. No. 11/347,147.
U.S. Office Action dated Feb. 4, 2009 for U.S. Appl. No. 11/347,147.
U.S. Office Action dated Aug. 6, 2009 for U.S. Appl. No. 11/347,147.
U.S. Office Action dated Nov. 7, 2008 for U.S. Appl. No. 10/944,270.
U.S. Office Action dated Jan. 28, 2009 for U.S. Appl. No. 10/944,270.
U.S. Office Action dated Apr. 21, 2009 for U.S. Appl. No. 10/944,270.
U.S. Office Action dated Nov. 17, 2008 for U.S. Appl. No. 12/117,582.
U.S. Office Action dated Mar. 3, 2009 for U.S. Appl. No. 12/117,582.
U.S. Office Action dated Aug. 6, 2009 for U.S. Appl. No. 12/117,582.
U.S. Office Action dated Nov. 17, 2008 for U.S. Appl. No. 12/118,931.
U.S. Office Action dated Mar. 4, 2009 for U.S. Appl. No. 12/118,931.
U.S. Office Action dated Jul. 30, 2009 for U.S. Appl. No. 12/118,931.
U.S. Office Action dated Nov. 25, 2008 for U.S. Appl. No. 12/117,961.

(56) References Cited

OTHER PUBLICATIONS

U.S. Office Action dated Aug. 6, 2009 for U.S. Appl. No. 12/117,961.
U.S. Office Action dated Dec. 5, 2008 for U.S. Appl. No. 12/120,902.
U.S. Office Action dated Oct. 21, 2009 for U.S. Appl. No. 12/120,902.
U.S. Office Action dated Mar. 17, 2009 for U.S. Appl. No. 11/690,127.
U.S. Office Action dated Mar. 23, 2009 for U.S. Appl. No. 11/804,309.
U.S. Office Action dated Mar. 23, 2009 for U.S. Appl. No. 11/926,326.
U.S. Office Action dated Aug. 28, 2009 for U.S. Appl. No. 11/150,847.
U.S. Office Action dated Dec. 29, 2008 for U.S. Appl. No. 11/193,020.
U.S. Office Action dated May 13, 2009 for U.S. Appl. No. 11/193,020.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
U.S. Appl. No. 11/789,705, filed Apr. 24, 2007.
U.S. Appl. No. 13/840,430, filed Mar. 15, 2013.
U.S. Appl. No. 11/355,512.
U.S. Appl. No. 11/438,090.
U.S. Appl. No. 11/655,794.
U.S. Appl. No. 11/725,151.
U.S. Appl. No. 11/789,704.
U.S. Appl. No. 11/888,284.
U.S. Appl. No. 11/926,565.
U.S. Appl. No. 11/928,097.
U.S. Appl. No. 11/930,716.
U.S. Appl. No. 11/930,786.
U.S. Appl. No. 12/100,361.
U.S. Appl. No. 12/341,602.
U.S. Appl. No. 12/543,445.
U.S. Appl. No. 12/727,190.
U.S. Appl. No. 12/729,109.
U.S. Appl. No. 12/756,099.
U.S. Appl. No. 12/768,963.
U.S. Appl. No. 12/769,915.
U.S. Appl. No. 12/828,170.
U.S. Appl. No. 13/315,191.
U.S. Appl. No. 13/355,758.
U.S. Appl. No. 13/429,857.
U.S. Appl. No. 13/784,293.
Japanese Office Action, Notification of Reasons for Refusal dated Sep. 18, 2013 for Application No. JP 2011-527942.
English Machine Translation for Application No. JP 5-503650.
U.S. Appl. No. 11/648,158, filed Dec. 29, 2006
U.S. Appl. No. 10/912,557.
U.S. Appl. No. 10/944,270.
U.S. Appl. No. 11/193,020.
U.S. Appl. No. 11/436,892.
U.S. Appl. No. 11/647,530.
U.S. Appl. No. 11/789,705.
U.S. Appl. No. 11/803,695.
U.S. Appl. No. 11/804,308.
U.S. Appl. No. 11/929,667.
U.S. Appl. No. 11/929,808.
U.S. Appl. No. 12/143,698.
U.S. Appl. No. 12/184,166.
U.S. Appl. No. 12/496,226.
U.S. Appl. No. 12/639,919.
U.S. Appl. No. 12/649,027.
U.S. Appl. No. 12/793,352.
U.S. Appl. No. 12/949,708.
U.S. Appl. No. 13/301,406.
U.S. Appl. No. 13/451,453.
U.S. Appl. No. 13/867,972.
U.S. Appl. No. 14/221,550.
U.S. Appl. No. 14/221,714.
U.S. Appl. No. 14/265,787.
U.S. Appl. No. 14/265,888.
U.S. Appl. No. 14/266,002.
U.S. Appl. No. 14/327,593.
U.S. Appl. No. 14/464,948.
U.S. Appl. No. 14/515,687.
U.S. Appl. No. 14/566,845.
U.S. Appl. No. 14/567,051.
U.S. Appl. No. 14/568,498.
U.S. Appl. No. 14/614,799.
U.S. Appl. No. 14/658,432.
U.S. Appl. No. 14/993,444.
Australian Office Action, Examiners First Report dated Dec. 9, 2011 for Application No. AU 2006292818.
Australian Office Action dated Feb. 12, 2014 for Application No. AU 2012202103.
Australian Office Action dated Aug. 1, 2014 for Application No. AU 2012244072.
Australian Office Action dated Sep. 17, 2014 for Application No. AU 2012202103.
Australian Office Action dated Sep. 30, 2014 for Application No. AU 2009293312.
Australian Office Action dated Oct. 1, 2014 for Application No. AU 2009333010.
Australian Office Action dated Jul. 8, 2015 for Application No. AU 2012244072.
Canadian Office Action dated Jul. 10, 2015 for Application No. CA 2,617,054.
Canadian Office Action dated Dec. 16, 2015 for Application No. CA 2,751,665.
Chinese Office Action, Third Office Action, dated Feb. 27, 2014 for Application No. CN 200980152995.1.
Chinese Office Action, Decision of Rejection, dated 2014 for Application No. CN 200980152995.1.
Chinese Office Action and Search Report dated Jan. 21, 2015 for Application No. CN 201310672731.6.
European Communication dated Sep. 27, 2011 for Application No. EP06800540.4.
European Communication dated Sep. 3, 2013 for Application No. EP 12182998.0.
European Communication dated Feb. 26, 2014 for Application No. EP 06800540.4.
European Communication dated Aug. 11, 2014 for Application No. EP 12182998.0.
European Communication dated Aug. 26, 2014 for Application No. EP 12183000.4.
European Communication dated Nov. 26, 2014 for Application No. EP 07836108.6.
European Communication dated Feb. 17, 2016 for Application No. EP 12162712.9.
Extended European Search Report dated Jan. 17, 2014 for Application No. EP 108426321.1.
Extended European Search Report dated Sep. 15, 2015 for Application No. EP 15163549.7.
Supplemental European Search Report dated Jan. 14, 2014 for Application No. EP 13184009.
Supplemental European Search Report dated Jan. 17, 2014 for Application No. EP 1084263.
Supplemental European Search Report dated Feb. 13, 2014 for Application No. EP 08746464.
Supplemental European Search Report dated Dec. 9, 2014 for Application No. EP 07839152.
European Search Report dated May 19, 2015 for Application No. EP 08746464.0.
European Search Report dated Jun. 23, 2015 for Application No. EP 12162712.9.
European Search Report dated Jun. 23, 2015 for Application No. EP 12162709.5.

(56) References Cited

OTHER PUBLICATIONS

International Written Opinion dated Aug. 9, 2011 for Application No. PCT/US2011/038751.
Japanese Office Action, Notification of Reasons for Refusal dated Nov. 12, 2013 for Application No. JP 2011-542562.
Japanese Office Action, Notification of Reasons for Refusal dated Jan. 7, 2014 for Application No. JP 2012-266049.
Japanese Office Action, Reasons for Refusal, dated Sep. 2, 2014 for Application No. JP 2012-544859.
Japanese Office Action, Reasons for Refusal, dated Jun. 9, 2015 for Application No. JP 2014-147174.
U.S. Appl. No. 11/648,158, filed Dec. 29, 2006.
U.S. Appl. No. 11/804,308, filed May 16, 2007.
U.S. Appl. No. 11/804,309, filed May 16, 2007.
U.S. Appl. No. 15/083,826, filed Mar. 29, 2016.

\* cited by examiner

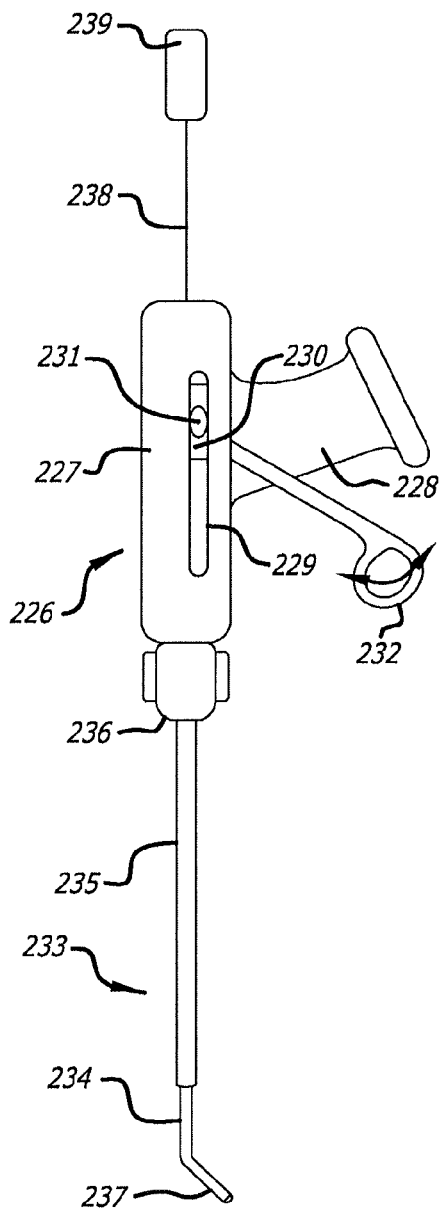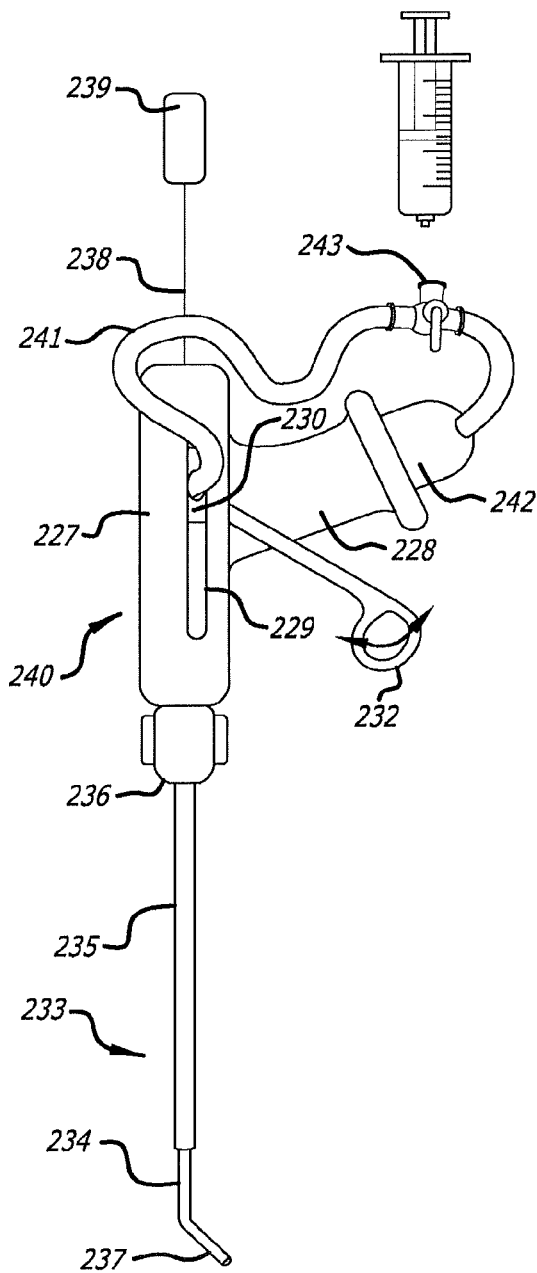
FIG. 2E
FIG. 2F

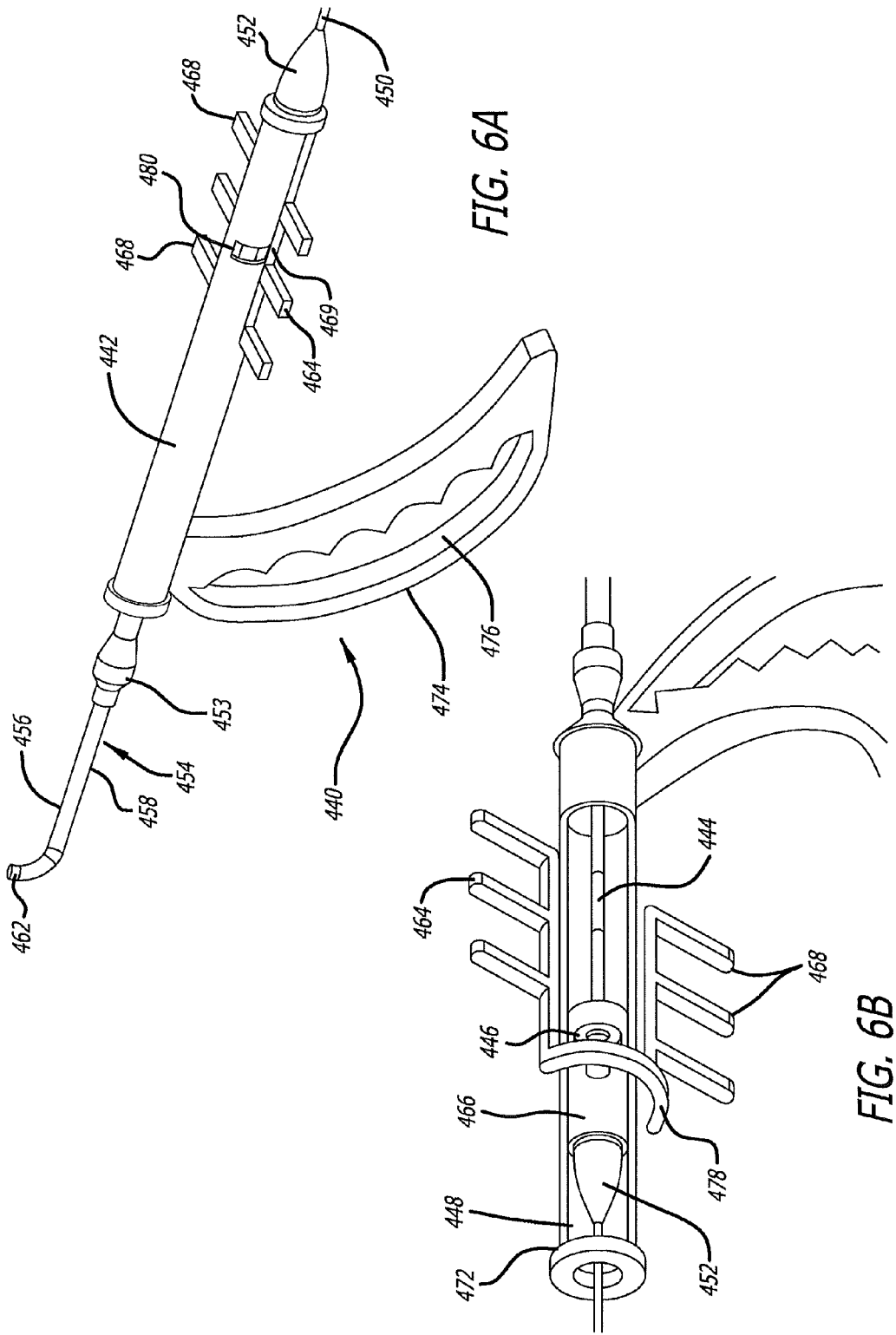

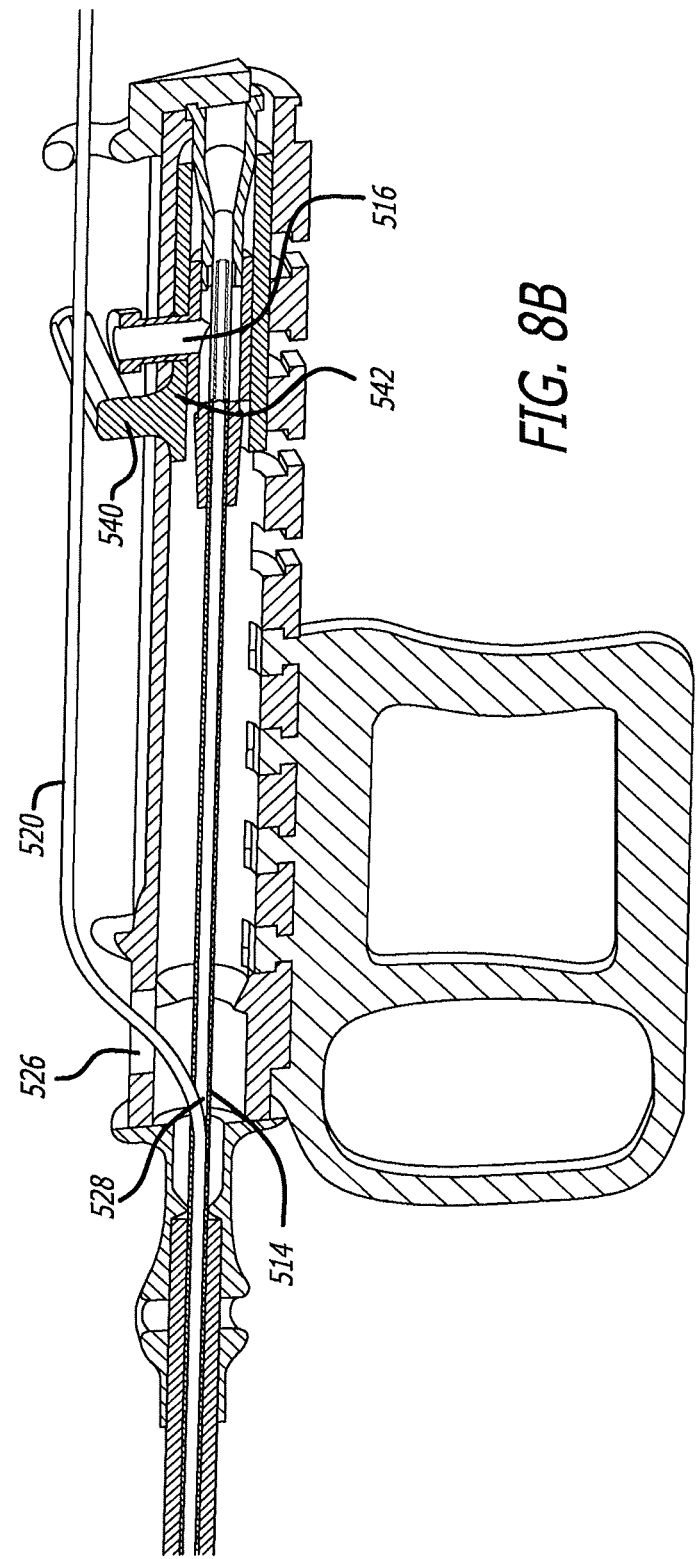

METHODS AND APPARATUS FOR TREATING DISORDERS OF THE EAR NOSE AND THROAT

CROSS-REFERENCES TO RELATED APPLICATIONS

This application is a continuation-in-part of U.S. patent application Ser. No. 11/193,020, filed Jul. 29, 2005, published as U.S. Pat. Pub. No. 2006/0063973, published on Mar. 23, 2006, which is a continuation-in-part of U.S. patent application Ser. No. 10/829,917, filed Apr. 21, 2004, now U.S. Pat. No. 7,654,997, issued on Feb. 2, 2010 U.S. patent application Ser. No. 10/944,270, filed Sep. 17, 2004, now abandoned, U.S. patent application Ser. No. 11/116,118, filed Apr. 26, 2005, now U.S. Pat. No. 7,720,521, issued on May 18, 2010, and U.S. patent application Ser. No. 11/150,847, filed Jun. 10, 2005, now U.S. Pat. No. 7,803,150, issued on Sep. 28, 2010, each such application being expressly incorporated herein by reference. This application claims the benefit of Provisional Application Ser. No. 61/098,157, filed Sep. 18, 2008, the contents of which are incorporated by reference.

FIELD OF THE INVENTION

The present invention relates generally to medical apparatus and methods. More specifically, the invention relates to devices and methods for accessing and dilating openings of the paranasal sinuses.

BACKGROUND

Functional endoscopic sinus surgery (FESS) is currently the most common type of surgery used to treat chronic sinusitis. In a typical FESS procedure, an endoscope is inserted into the nostril along with one or more surgical instruments. The surgical instruments are then used to cut tissue and/or bone, cauterize, suction, etc. In most FESS procedures, the natural ostium (e.g., opening) of at least one paranasal sinus is surgically enlarged to improve drainage from the sinus cavity. The endoscope provides a direct line-of-sight view whereby the surgeon is typically able to visualize some but not all anatomical structures within the surgical field. Under visualization through the endoscope, the surgeon may remove diseased or hypertrophic tissue or bone and may enlarge the ostia of the sinuses to restore normal drainage of the sinuses. FESS procedures can be effective in the treatment of sinusitis and for the removal of tumors, polyps and other aberrant growths from the nose.

The surgical instruments used in the prior art FESS procedures have included; applicators, chisels, curettes, elevators, forceps, gouges, hooks, knives, saws, mallets, morselizers, needle holders, osteotomes, ostium seekers, probes, punches, backbiters, rasps, retractors, rongeurs, scissors, snares, specula, suction canulae and trocars. The majority of such instruments are of substantially rigid design.

In order to adequately view the operative field through the endoscope and/or to allow insertion and use of rigid instruments, many FESS procedures of the prior art have included the surgical removal or modification of normal anatomical structures. For example, in many prior art FESS procedures, a total uncinectomy (e.g., removal of the uncinate process) is performed at the beginning of the procedure to allow visualization and access of the maxilary sinus ostium and/or ethmoid bulla and to permit the subsequent insertion of the rigid surgical instruments. Indeed, in most traditional FESS procedures, if the uncinate process is allowed to remain, such can interfere with endoscopic visualization of the maxillary sinus ostium and ethmoid bulla, as well as subsequent dissection of deep structures using the available rigid instrumentation.

More recently, new devices, systems and methods have been devised to enable the performance of FESS procedures and other ENT surgeries with minimal or no removal or modification of normal anatomical structures. Such new methods include, but are not limited to, uncinate-sparing Balloon Sinuplasty™. procedures and uncinate-sparing ethmoidectomy procedures using catheters, non-rigid instruments and advanced imaging techniques (Acclarent, Inc., Menlo Park, Calif.). Examples of these new devices, systems and methods are described in incorporated U.S. patent application Ser. No. 10/829,917 entitled Devices, Systems and Methods for Diagnosing and Treating Sinusitis and Other Disorders of the Ears, Nose and/or Throat, now U.S. Pat. No. 7,654,997, issued on Feb. 2, 2010; Ser. No. 10/944,270 entitled Apparatus and Methods for Dilating and Modifying Ostia of Paranasal Sinuses and Other Intranasal or Paranasal Structures, now abandoned; Ser. No. 11/116,118 entitled Methods and Devices for Performing Procedures Within the Ear, Nose, Throat and Paranasal Sinuses filed Apr. 26, 2005, now U.S. Pat. No. 7,720,521, issued on May 18, 2010, and Ser. No. 11/150,847 entitled Devices, Systems And Methods Useable For Treating Sinusitus, filed on Jun. 10, 2005, now U.S. Pat. No. 7,803,150 issued on Sep. 28, 2010.

Though the Balloon Sinuplasty™ system has led to great advances in paranasal sinus treatments, further development and refinement of the system and methods for using it are continually being sought. For example, it would be desirable to have a system that is simpler than the current system for physicians to use, especially for physicians who are new to the system. Ideally, such a simplified system could be used and manipulated by one user and not require an assistant, at least in some cases. Also ideally, such a system would be simply packaged in a way that was convenient for the user. At least some of these objectives will be met by the present invention.

SUMMARY

The various embodiments disclosed herein provide apparatus, systems and methods for accessing and dilating paransal sinus openings. Generally, each of the various embodiments combines two or more surgical instruments or instrument features into a device (or system) that can be held in one hand, thus helping to free up the other hand of the user and/or to make a procedure easier to perform. For example, in one embodiment a guide and a balloon catheter may be coupled together via a handle. In some embodiments, a guidewire and/or an endoscope may also be coupled with the balloon catheter and/or the handle. The various devices and methods of these various embodiments may be used separately or in any possible and desirable combinations with each other.

In accordance with one embodiment, a device for dilating an ostium of a paranasal sinus of a human or animal subject includes a handle and an elongate shaft having a proximal end coupled with the handle and extending to a distal end. The shaft includes a lumen and a longitudinal opening extending from the lumen to an outer surface of the shaft along at least part of a length between the proximal and distal ends. This embodiment also includes a guidewire disposed through at least a portion of the shaft lumen and a dilator having a non-expanded configuration and an expanded configuration, wherein at least a portion of the dilator is disposed over the guidewire and within the shaft lumen. A slide member is also coupled with the guidewire or the dilator through the longitudinal opening of the shaft for advancing the guidewire and/or the dilator relative to the shaft. In one embodiment, the slide is capable of axial rotation relative to the elongate shaft to rotate the guidewire and/or the dilator. Also, in certain embodiments, the device includes a piercing member coupled with the distal end of the shaft for piercing a hole into a paranasal sinus of the subject, wherein the distal end of the shaft is insertable through the hole.

In another embodiment, the device includes a fluid reservoir attached to the elongate shaft, and the fluid reservoir is in fluid communication with the dilator. There may also be a trigger or actuation handle coupled with the fluid reservoir, and actuating the trigger causes fluid in the fluid reservoir to inflate the dilator into the expanded configuration.

In accordance with another embodiment of a device for accessing an ostium of a paranasal sinus of a human or animal subject, the device includes a handle and an elongate shaft having a proximal end coupled with the handle and extending to a distal end. The elongate shaft includes a longitudinal lumen extending at least partway from the proximal end to the distal end. There is also a device advancing member coupled with the handle or the elongate shaft and configured to couple with and advance one device through the lumen of the shaft and at least partway into an ostium of a paranasal sinus. In certain embodiments, a guidewire extends through at least part of the elongate shaft lumen, and the device advancing member is configured to couple with and advance the guidewire through the lumen and through the ostium of the paranasal sinus. In one embodiment, a balloon dilation catheter extends through at least part of the shaft lumen, wherein the device advancing member is configured to couple with and advance the balloon dilation catheter through the lumen and at least partway into the ostium of the paranasal sinus.

In accordance with one embodiment of a system for dilating an anatomical structure within the ear, nose or throat of a human or animal subject, includes an endoscope and an elongate tubular guide removably coupled with the endoscope. There is also a handle coupled with at least one of the endoscope for grasping the endoscope or the elongate tubular guide in one hand. In one embodiment, a dilator is slidably disposed in the elongate tubular guide, wherein the dilator has a non-expanded configuration for passing through the elongate tubular guide and an expanded configuration for dilating the anatomical structure. In certain embodiments, a first clip is attached to the endoscope and a second clip is attached to the elongate tubular guide. A connection member for connecting the first and second clips is also included.

In one embodiment, the endoscope and elongate tubular guide, coupled together, are sized to pass into a hole punctured into a paranasal sinus of the subject. In this embodiment, the system further includes a piercing member coupled with at least one of the endoscope or the elongate tubular guide for forming the hole.

The system may also include a guidewire disposed through a guidewire lumen extending through at least part of the dilator, and in one embodiment, a guidewire advancing member coupled with the elongate tubular guide for advancing the guidewire relative to the guide may also be included. Still another embodiment, the system includes an endoscope cleaner coupled with the endoscope. The endoscope cleaner includes a sheath disposed over at least part of the endoscope and a tube coupled with the sheath to connect the sheath with a source of cleaning fluid.

According to one embodiment of a method for dilating an opening in a paranasal sinus of a human or animal subject, the method includes holding an elongate, tubular, at least partially rigid guide in one hand using a handle, wherein a balloon dilation catheter resides within a lumen of the guide and extends through the handle. Also, the method includes advancing a distal end of the guide to a position near an opening in a paranasal sinus of a human or animal subject, wherein the balloon catheter resides within the lumen of the guide during advancement. Once in position, the method further includes advancing the balloon dilation catheter through the guide to position a balloon of the balloon dilation catheter in the paranasal sinus opening. The balloon of the balloon dilation catheter is then expanded to dilate the opening. In one embodiment, the method may include advancing the balloon dilation catheter by advancing an advancement member coupled with the handle and the catheter. Also, in certain embodiments, the method may include advancing a guidewire through the distal end of the guide and through the opening into the paranasal sinus, wherein the guidewire resides within a lumen of the balloon catheter during advancement of the guide into the subject, and wherein the balloon catheter is advanced through the distal end of the guide over the guidewire.

In one embodiment, the method also includes emitting light from a distal end of the guidewire, and viewing the emitted light from outside the subject to confirm that the distal end of the guidewire is located in the paranasal sinus before advancing the balloon dilation catheter.

In another embodiment, the guide is advanced through an opening in a canine fossa of the subject's head into a maxillary sinus or through an opening in a wall of the maxillary sinus, the method also including forming the canine fossa opening or the maxillary sinus wall opening using a piercing tool.

In yet another embodiment, the method includes holding an endoscope with the handle, wherein the endoscope and the guide are coupled with the handle, and wherein the endoscope and the guide are advanced into the subject. In another embodiment, the endoscope, guide and balloon catheter are advanced into the subject together. Further, the distal end of the guide or the balloon of the balloon catheter is viewed using the endoscope.

These and other aspects and embodiments are described in further detail below, with reference to the accompanying drawing figures.

BRIEF DESCRIPTION OF THE DRAWING

FIG. 2E is a side view of another dilation device useable to dilate openings of paranasal sinuses and other anatomical passages within the ear, nose and throat;

FIG. 2F is a side view of another dilation device which uses compressed inflation fluid to inflate a dilator balloon to dilate openings of paranasal sinuses and other anatomical passages within the ear, nose and throat;

FIG. 6A is a perspective view of another embodiment of a surgical hand tool;

FIG. 6B is a cross-section view of the surgical hand tool shown in FIG. 6A;

FIG. 8B is a cross-section view of the surgical hand tool shown in FIG. 8A;

DETAILED DESCRIPTION

The following detailed description, the accompanying drawings and the above-set-forth Brief Description of the Drawings are intended to describe some, but not necessarily all, examples or embodiments of the invention. This detailed description and the accompanying drawings are provided primarily for exemplary purposes and should not be interpreted to limit the scope of the invention as described by the claims. Although the Balloon Sinuplasty™ paranasal sinus procedure is sometimes mentioned in this description, many embodiments of the present invention may be used in performing any other paranasal sinus procedures.

The devices disclosed herein may be used alone or in various combinations to perform various procedures including, but not limited to, various procedures within paranasal sinuses and/or within openings of paranasal sinuses. As used herein, unless specified otherwise, the term "opening(s) of paranasal sinus(es)" shall include any opening in a paranasal sinus or air cell including but not limited to: natural ostia, natural canals, surgically altered natural ostia, surgically created openings, antrostomy openings, ostiotomy openings, burr holes, drilled holes, puncture tracts, ethmoidectomy openings, fenestrations and other natural or man made passageways.

Figure 1:
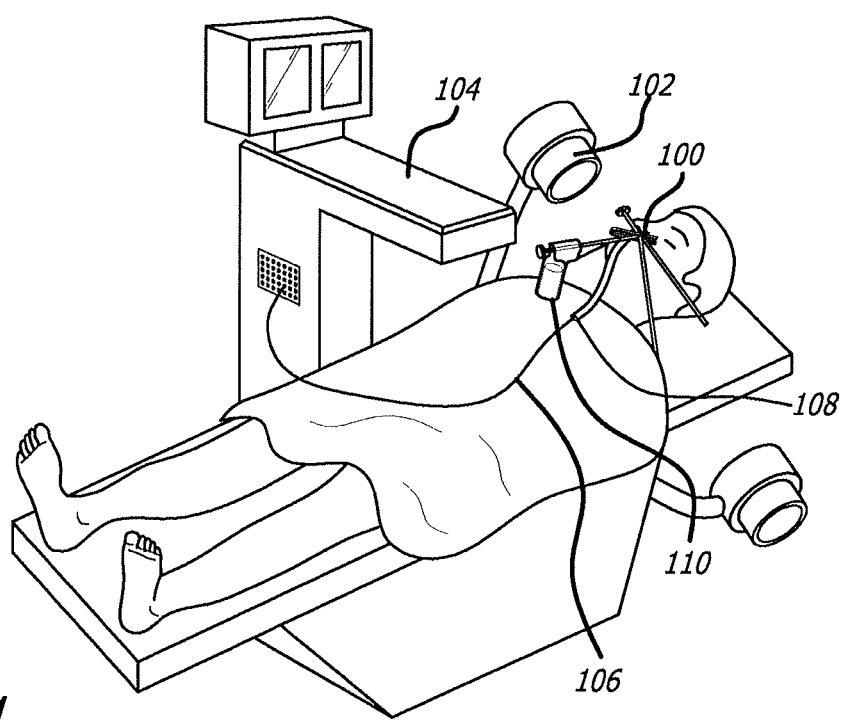
FIG. 1 is a perspective view of a human subject undergoing a procedure for treating sinusitis in accordance with the present invention.

FIG. 1 shows a human subject undergoing a Balloon Sinuplasty™ procedure for treating sinusitis in accordance with one embodiment. The human subject may be subjected to one or more diagnostic, therapeutic or access devices introduced through an optional support device 100. In many cases, paranasal sinus procedures of the present invention are performed without using any support device 100, but such may be convenient, for example, in performing a procedure in a procedure room of a physicians clinic or other setting where an assistant is not available. One example of a therapeutic device that may be used in procedures of the present invention is a balloon catheter used to dilate openings of paranasal sinuses or other endonasal anatomical structures. One example of an access device that may be used in such procedures is a guidewire used to access natural ostia of paranasal sinuses or a natural or artificial passageway or tract leading to paranasal sinuses. In the embodiment shown in FIG. 1, support device 100 includes a support member that is stabilized by three or more legs that rest on the operating table. The one or more diagnostic, therapeutic or access devices may be tracked or navigated through the anatomy using one or more tracking or navigation modalities. In the embodiment shown in FIG. 1, a C-arm fluoroscope 102 provides fluoroscopic visualization of anatomical regions during the procedure. An instrument console 104 comprising one or more functional modules may also be provided. Instrument console 104 can be controlled by console control means e.g. a foot pedal controller, a remote controller etc. Instrument console 104 may be fitted with wheels to enable an operator to change the position of the instrument console in an operating area. Instrument console 104 may comprise functional modules including, but not limited to:

1. Suction pump for delivering a controlled amount of vacuum to a suction device, 2. Irrigation pump to deliver saline or other suitable irrigation medium, 3. Power module to supply power to drills or other electrical devices, 4. Storage modules for storing instruments, medications, etc., 5. Energy delivery module to provide radiofrequency, laser, ultrasound or other therapeutic energy to a surgical device, 6. Fluoroscope, MRI, CT, Video, Endoscope 106 or Camera or other imaging modules to connect or interact with devices used during various diagnostic or therapeutic procedures, 7. Display module e.g. a LCD, CRT or Holographic screen to display data from various modules such as an endoscope, fluoroscope or other data or imaging module, 8. Remote control module to enable an operator to control one or more parameters of one or more functional modules, and 9. Programmable Microprocessor that can store one or more operation settings for one or more functional modules etc.

In the embodiment shown in FIG. 1, instrument console 104 is connected to an endoscope 106. Endoscope 106 may be introduced in the anatomy through one or more introducing devices 108 such as guide catheters. A physician may use a hand held introducer 110 comprising a surgical navigation modality to introduce one or more diagnostic, therapeutic or access devices into the anatomy. Examples of surgical navigation modalities that may be located on introducer 110 include, but are not limited to navigation modalities comprising reflective passive elements, light emitting diodes, transmitters or receivers of energy (e.g. optical energy, radiofrequency energy, etc.), a combination of two or more of the above-mentioned navigation modalities, etc.

As is evident from the above description, a Balloon Sinuplasty™ procedure may involve using a number of different surgical intruments (or "tools"). For example, a physician will typically use an endoscope, a guide, a guidewire, a balloon catheter, an inflation device for inflating the balloon catheter, and a C-arm fluoroscopy device for observing at least part of the procedure. In some cases, a lighted guidewire (for example, the Relieva Luma™ Sinus Illumination Guidewire from Acclarent, Inc.) may be used, in which case a light source is attached to the guidewire during at least part of the procedure. Optionally, a procedure may also include irrigation (cleaning out using saline or other fluid) of one or more paranasal sinuses to remove mucus from the sinus(es), using for example a irrigation catheter (such as the Relieva Vortex™ Sinus Irrigation Catheter from Acclarent, Inc.). Additionally, in some procedures multiple guides may be used to reach different sinuses, with each guide having a different angle and/or size. Different balloon catheters may also be used, with some balloon diameters being different for different sized paranasal sinus openings. Furthermore, in different cases other instruments may be used, some of which are described, for example, on the Acclarent, Inc. web site (www.acclarent.com). In some instances, therefore, it may be desirable to couple or otherwise combine two or more instruments, features or the like, in order to simplify a procedure, allow a physician to hold multiple instruments in one hand, or otherwise facilitate or enhance a paranasal sinus procedure such as (but not limited to) a Balloon Sinuplasty™ procedure.

Figure 2A:
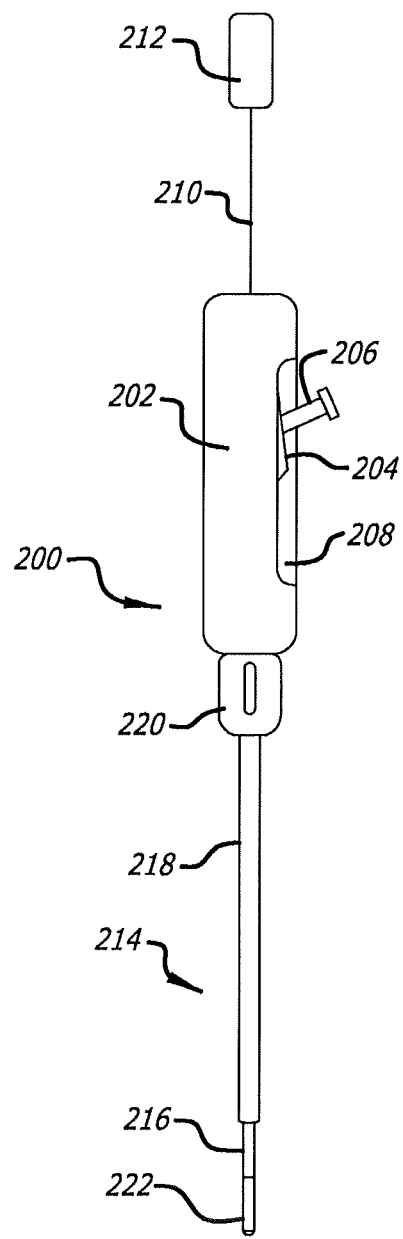
FIG. 2A is a top view of a dilation device useable to dilate the ostia or paranasal sinuses and other anatomical passages within the ear, nose and throat.
Figure 2B:
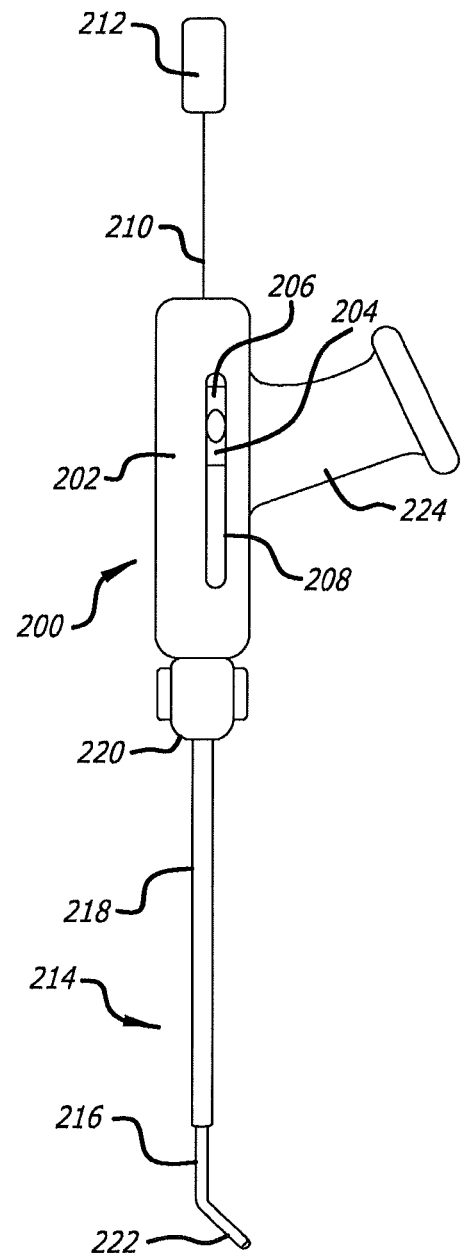
FIG. 2B is a side view of the device of FIG. 27A.

Referring now to FIGS. 2A and 2B, one embodiment of a surgical hand tool 200 comprising a balloon catheter is shown in top view (FIG. 2A) and side view (FIG. 2B). In this embodiment, surgical hand tool 200 may include a hollow proximal body 202 made of biocompatible materials including, but not limited to ABS, nylon, polyurethane, polyethylene, etc. Proximal body 202 encloses a balloon catheter 204. Balloon catheter 204 comprises a balloon inflation port 206 to inflate a balloon on balloon catheter 204. Balloon inflation port 206 emerges out of proximal body 202 through a longitudinal slit 208 through proximal body 202 such that balloon catheter 204 can slide along the axis of proximal body 202. Balloon inflation port 206 is connected to a suitable inflating device to inflate the balloon of balloon catheter 204. In this embodiment, balloon catheter 204 is introduced into a desired region of the anatomy over a guidewire 210. The proximal region of guidewire 210 may comprise a torquing device 212. A user can use torquing device 212 to rotate, advance, retract, or torque guidewire 210. The distal region of proximal body 202 comprises a suitable hub that allows a guide catheter 214 to attach to proximal body 202. In an alternate embodiment, guide catheter 214 is permanently attached to proximal body 202. In this embodiment, guide catheter 214 comprises an elongate tubular element 216 made of suitable biocompatible materials including, but not limited to PEEK, Pebax, Nylon, Polyimide, ABS, PVC, polyethylene, etc. The proximal region of tubular element 216 may be covered by a hypotube 218 made of suitable biocompatible metals or polymers. The proximal end of tubular element 216 is attached to a suitable hub 220. Hub 220 allows the reversible attachment of guide catheter 214 to proximal body 202. In one embodiment, hub 220 is a female luer lock that attaches to a suitable hub on proximal body 202. Thus, various guide catheters can be attached to the distal region of proximal body 202 to provide access to various anatomical regions. The distal end of tubular element 216 may comprise an atraumatic tip 222. The distal end of tubular element 216 may comprise a curved, bent or angled region. FIG. 2B shows the side view of surgical hand tool 200 showing a handle 224 attached to proximal body 202.

Figure 2C:
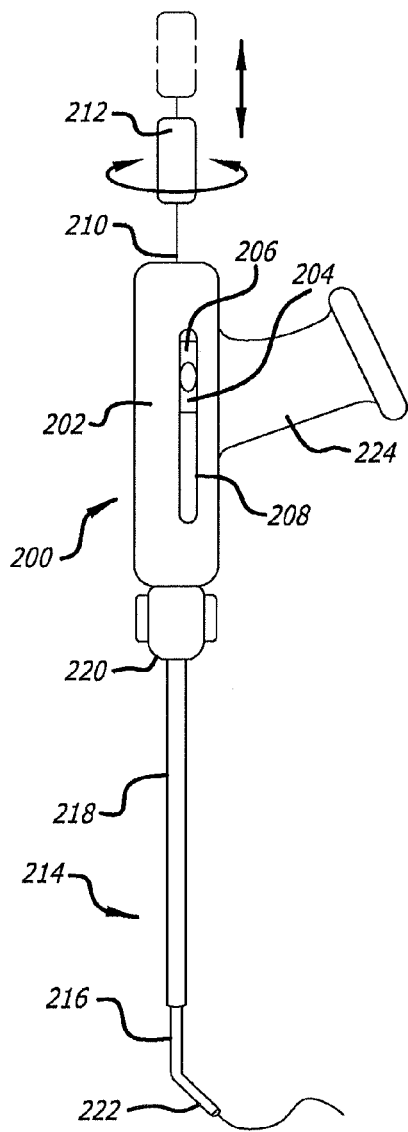
FIGS. 2C-2D show steps in a method for using the dilation device of FIGS. 27A-27B.
Figure 2D:
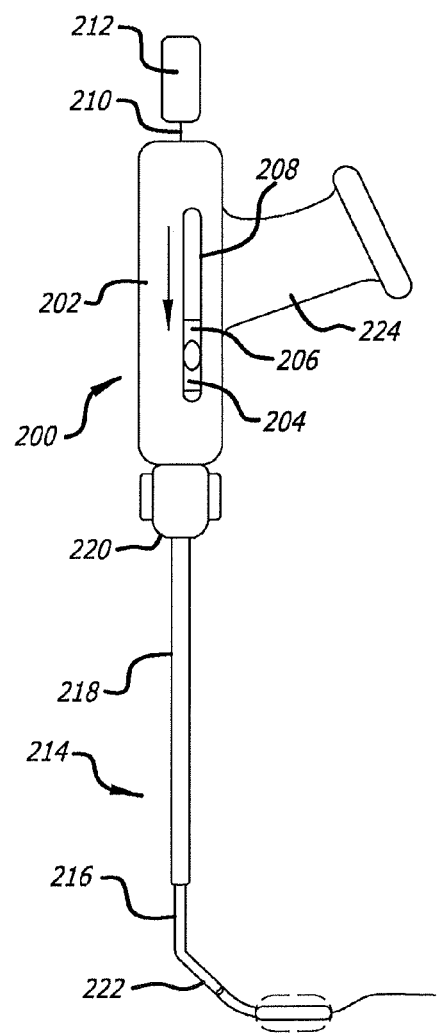

FIGS. 2C through 2D show various steps of a method of dilating an anatomical region using the surgical hand tool 200 shown in FIGS. 2A and 2B. In FIG. 2C, surgical hand tool 200 is introduced in the anatomy. Surgical hand tool 200 is positioned such that the distal tip of surgical hand tool 200 is located near an anatomical region to be accessed. Thereafter, a guidewire 210 is introduced through surgical hand tool 200 such that the distal tip of guidewire 210 is located near an anatomical region to be accessed. During this step, guidewire 210 may be navigated through the anatomy using torquing device 212. In one embodiment, guidewire 210 is positioned across a paranasal sinus ostium to be dilated. Thereafter, in FIG. 2D, balloon catheter 204 is advanced over guidewire 210 into the anatomy. This is done by pushing balloon inflation port 206 in the distal direction. Thereafter, balloon catheter 204 is used to perform a diagnostic or therapeutic procedure. In one embodiment, balloon catheter 204 is used to dilate an opening leading to a paranasal sinus such as a paranasal sinus ostium.

FIG. 2E shows a side view of a first alternate embodiment of a surgical hand tool 226 comprising a balloon catheter. The design of surgical hand tool 226 is similar to the design of surgical hand tool 200. Surgical hand tool 226 comprises a hollow elongate body 227 made of biocompatible materials including, but not limited to ABS, nylon, polyurethane, polyethylene, etc. Elongate body 227 is attached to a handle 228 to allow a user to grasp surgical hand tool 226. Elongate body 227 comprises a longitudinal slit 229. Elongate body 227 encloses a balloon catheter 230. Balloon catheter 230 comprises a balloon inflation port 231 to inflate a balloon on balloon catheter 230. Balloon inflation port 231 emerges out of elongate body 227 through longitudinal slit 229 such that balloon catheter 230 can slide along the axis of elongate body 227. Balloon catheter 230 is further connected to a trigger 232. Trigger 232 is pivoted on elongate body 227 such that pulling trigger 232 in the proximal direction causes balloon catheter 230 to move in the distal direction. Similarly, pushing trigger 232 in the distal direction causes balloon catheter 230 to move in the proximal direction. Thus, balloon catheter 230 can be moved by moving trigger 232. The distal region of elongate body 227 comprises a suitable hub that allows a guide catheter 233 to attach to elongate body 227. In this embodiment, guide catheter 233 comprises an elongate tubular element 234 made of suitable biocompatible materials including, but not limited to PEEK, Pebax, Nylon, polyethylene, etc. The proximal region of tubular element 234 may be covered by a hypotube 235 made of suitable biocompatible metals or polymers. The proximal end of tubular element 234 is attached to a suitable hub 236. Hub 236 allows the reversible attachment of guide catheter 233 to elongate body 227. In one embodiment, hub 236 is a female luer lock that attached to a suitable hub on elongate body 227. Thus, various guide catheters can be attached to the distal region of elongate body 227 to provide access to various anatomical regions. The distal end of tubular element 234 may comprise an atraumatic tip 237. The distal end of tubular element 234 may comprise a curved, bent or angled region. In this embodiment, balloon catheter 230 is introduced into a desired region of the anatomy over a guidewire 238. The proximal region of guidewire 238 may comprise a torquing device 239. A user can use torquing device 239 to rotate, advance, retract, or torque guidewire 238. Surgical hand tool 226 can be used to introduce balloon catheter 230 into a desired anatomical region to perform a diagnostic or therapeutic procedure in the anatomical region.

FIG. 2F shows a side view of a second alternate embodiment of a surgical hand tool 240 comprising a balloon catheter. The design of surgical hand tool 240 is similar to the design of surgical hand tool 226. Surgical hand tool 240 further comprises a fluid delivery mechanism to deliver inflating fluid for inflating the balloon of balloon catheter 230. The fluid delivery mechanism comprises an elongate tube 241 connected to balloon inflation port 231. Elongate tube 241 is further connected to a fluid reservoir 242. In one embodiment, fluid reservoir 242 comprises a pressurized gas such as air, nitrogen, carbon dioxide, etc. The delivery of fluid from fluid reservoir 242 to balloon catheter 230 is controlled by a valve 243.

Figure 2G:
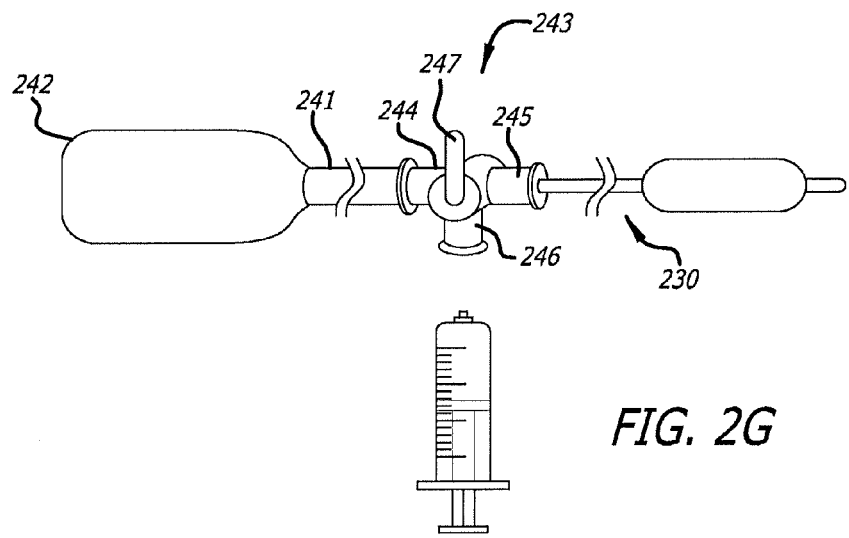
FIG. 2G is a schematic diagram of the valving arrangement of the device shown in FIG. 27F.
Figure 2H:
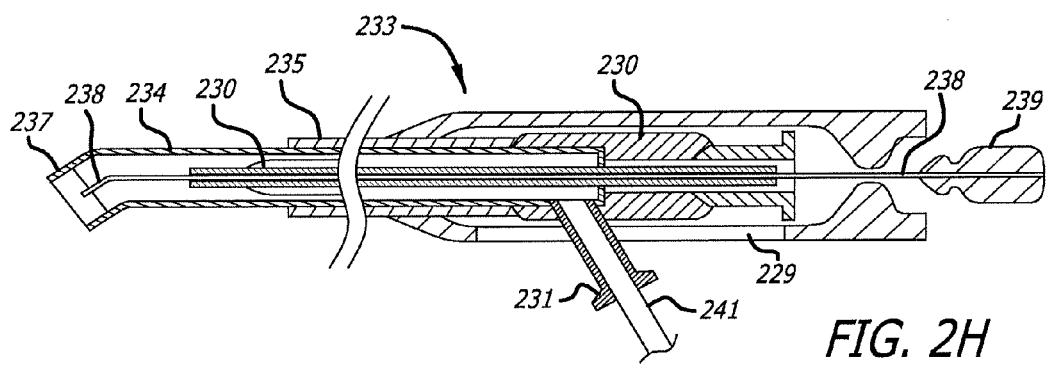
FIG. 2H is a partial sectional view through a portion of the device of FIG. 27A-B.

FIG. 2H shows partial sectional view of the surgical hand tool 240 shown in FIG. 2F. The proximal region of elongate body 227 comprises longitudinal slit 229. Elongate body 227 encloses balloon catheter 230. The proximal end of balloon catheter 230 comprises a Y shaped hub. The Y-shaped hub comprises balloon inflation port 231. Balloon inflation port 231 in turn is connected to elongate tube 241. Guidewire 238 enters elongate body 227 through an opening in the proximal end of elongate body 227.

FIG. 2G shows a perspective view of an embodiment of the valve arrangement of the device shown in FIG. 2F. The valve arrangement comprises a three way valve 243. In one embodiment, three way valve 243 is a three way luer valve. A first arm 244 of three way valve 243 is connected by elongate tube 241 to fluid reservoir 242. A second arm 245 of three way valve 243 is in fluid communication with the balloon of balloon catheter 230. A third arm 246 of three way valve 243 is connected to a drain or is open to the atmosphere. Third arm 246 may be connected to a syringe or a source of vacuum to deflate balloon of balloon catheter 230. Such an arrangement comprising a syringe or a source of vacuum connected to third arm 246 is especially useful to deflate a non-compliant balloon. Three way valve 243 further comprises a control knob 247. In a first position of control knob 247, a fluid communication is created between first arm 244 and second arm 245. In a second position of control knob 247, a fluid communication is created between second arm 245 and third arm 246. A user can turn control knob 247 in the first position to inflate the balloon of balloon catheter 230. The user can then turn control knob 247 in the second position to deflate the balloon of balloon catheter 230. Other suitable valve arrangements may also be used instead of a three way valve for controllably inflating or deflating the balloon of balloon catheter 230.

Figures 3A, 3B:
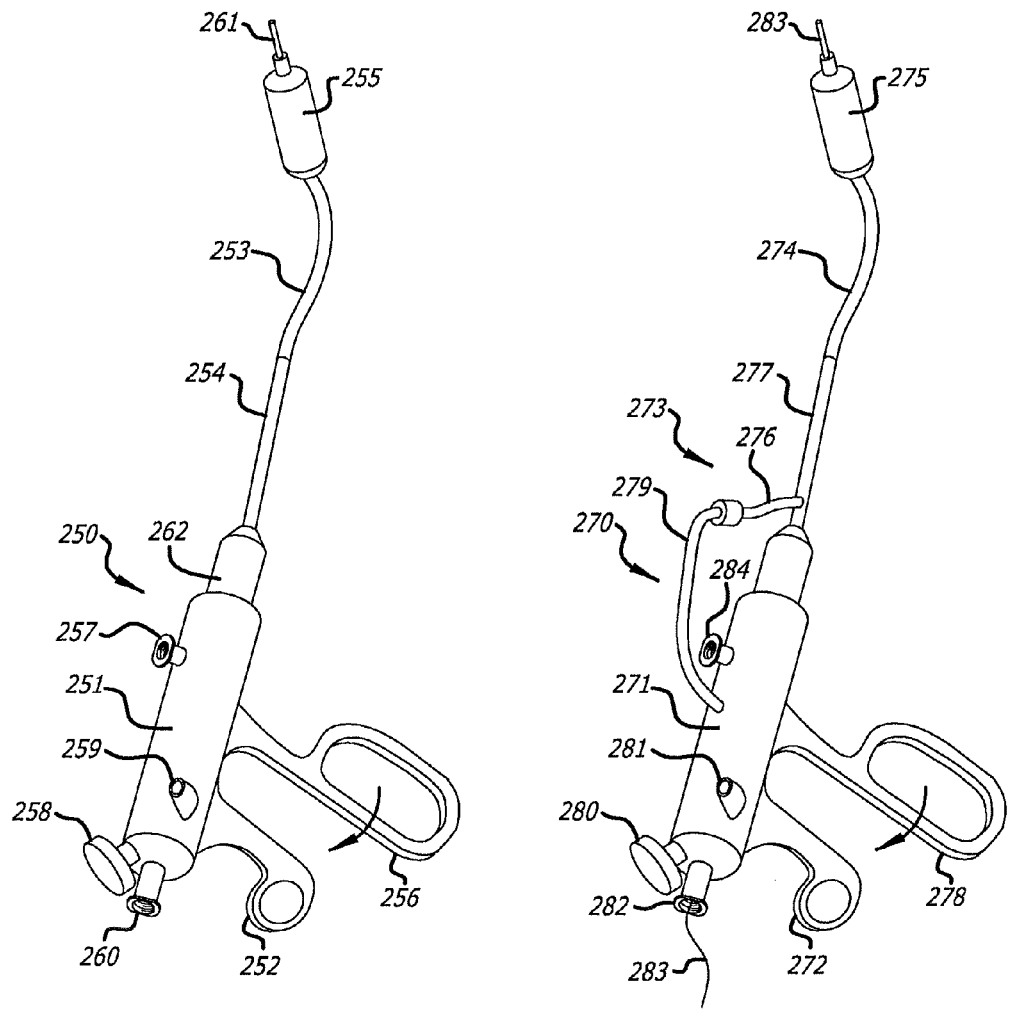
FIG. 3A is a perspective view of a hand grip inflator device attached to a balloon catheter.
FIG. 3B is a perspective view of a balloon dilation device having a hand grip inflator.

FIG. 3A shows a perspective view of an embodiment of a handheld balloon catheter tool 250. Balloon catheter tool 250 comprises a proximal region 251. Proximal region 251 comprises a handle 252 to enable a user to hold balloon catheter tool 250. Balloon catheter tool 250 further comprises a balloon catheter shaft 253. In one embodiment, balloon catheter shaft 253 extends distally from the distal region of proximal region 251. In another embodiment, balloon catheter shaft 253 extends till the proximal end of proximal region 251. Balloon catheter shaft 253 may further comprise a hypotube 254 surrounding a region of balloon catheter shaft 253. The distal region of balloon catheter shaft 253 comprises an inflatable balloon 255 that can be used to dilate one or more regions of the anatomy. Balloon 255 is inflated by a trigger 256 located adjacent to handle 252. Trigger 256 is connected to a plunger that is further connected to an inflating fluid reservoir. Pulling trigger 256 causes the inflating fluid stored in an inflating fluid reservoir to be delivered to balloon 255 under pressure. Balloon catheter tool 250 may further comprise a flushing port 257 to flush a lumen of balloon catheter shaft 253.

During a procedure, a user inflates balloon 255 to a desired pressure using the inflating fluid stored in the inflating fluid reservoir. The pressure in balloon 255 can be measured by a pressure sensor or gauge 258 that is in fluid communication with the inflating fluid within balloon 255. Balloon catheter tool 250 may further comprise a ratcheting mechanism 259 to allow a user to pull trigger 256 in incremental steps. This allows the user to inflate balloon 255 in incremental steps. Similarly, balloon catheter tool 250 may comprise a ratcheting mechanism to allow a user to release trigger 256 in incremental steps after inflating balloon 255. This allows the user to deflate balloon 255 in incremental steps. In one embodiment, balloon catheter tool 250 can be advanced over a guidewire to a desired target location in the anatomy. In this embodiment, balloon catheter tool 250 may further comprise a proximal guidewire port 260 that is in fluid communication with a guidewire lumen in balloon catheter shaft 253. This enables balloon catheter tool 250 to be introduced over a guidewire into the anatomy. In another embodiment, balloon catheter tool 250 comprises a fixed guidewire 261 at the distal tip of balloon catheter tool 250 to navigate balloon catheter tool 250 through the anatomy. In one embodiment, balloon catheter tool 250 comprises a rotation knob 262. Rotation knob 262 allows a user to rotate balloon catheter shaft 253. Balloon catheter tool 250 may further comprise one or more navigational modalities including, but not limited to radio opaque markers, electromagnetic navigational sensors, etc. The distal region of balloon catheter tool 250 may be introduced in the anatomy through a variety of introducing devices disclosed herein including, but not limited to a guide catheter.

FIG. 3B shows a perspective view of an embodiment of a detachable handheld balloon catheter inflation tool 270. Detachable inflation tool 270 comprises a body 271 comprising a handle 272 to enable a user to hold inflation tool 270. Detachable inflation tool 270 attaches to a balloon catheter 273. In one embodiment, a user is provided with a kit comprising a detachable inflation tool 270 and multiple balloon catheters. In the embodiment shown in FIG. 3B, balloon catheter 273 comprises an elongate balloon catheter shaft 274. The distal region of balloon catheter shaft 274 comprises an inflatable balloon 275 that can be used to dilate one or more regions of the anatomy. The proximal region of balloon catheter shaft 274 is connected to a suitable hub 276 comprising a side port for inflating balloon 275. In one embodiment, balloon catheter shaft 274 comprises a hypotube 277 surrounding a region of balloon catheter shaft 275. Balloon 275 is inflated by a trigger 278 located adjacent to handle 272. Trigger 278 is connected to a plunger that is further connected to an inflating fluid reservoir. Pulling trigger 278 causes an inflating fluid stored in the inflating fluid reservoir to be delivered to balloon 255 under pressure. The inflating fluid is delivered through a fluid delivery port 279 that attaches to the side port of hub 276. During a procedure, a user inflates balloon 275 to a desired pressure using the inflating fluid stored in the inflating fluid reservoir. The pressure in balloon 275 can be measured by a pressure sensor or gauge 280 that is in fluid communication with the inflating fluid within balloon 275. Detachable inflation tool 270 may further comprise a ratcheting mechanism 281 to allow a user to pull trigger 278 in incremental steps. This allows the user to inflate balloon 275 in incremental steps. Similarly, detachable inflation tool 270 may comprise a ratcheting mechanism to allow a user to release trigger 278 in incremental steps after inflating balloon 275. This allows the user to deflate balloon 275 in incremental steps. In one embodiment, the combination of balloon catheter 273 and balloon catheter tool 270 can be advanced over a guidewire to a desired target location in the anatomy. In this embodiment, balloon catheter tool 270 may further comprise a proximal guidewire port 282 that is in fluid communication with a guidewire lumen in balloon catheter shaft 274. This enables balloon catheter tool 270 to be introduced over a guidewire 283 into the anatomy. In another embodiment, balloon catheter 273 comprises a fixed guidewire at the distal tip of balloon catheter 273 to navigate balloon catheter 273 through the anatomy. In another embodiment, balloon catheter 273 comprises a rapid exchange lumen. The rapid exchange lumen enables balloon catheter 273 to be introduced over a suitable guidewire. Balloon catheter tool 270 may further comprise a flushing port 284 to flush a lumen of balloon catheter 273. Balloon catheter tool 270 may further comprises one or more navigational modalities including, but not limited to radio opaque markers, electromagnetic navigational sensors, etc. The distal region of balloon catheter 273 may be introduced in the anatomy through a variety of introducing devices including, but not limited to a guide catheter.

The balloon catheter tool 250 of FIG. 3A or the detachable handheld balloon catheter inflation tool 270 of FIG. 3B may be designed to inflate a balloon to a fixed pressure. Alternatively, they may be designed to deliver a fixed volume of inflating fluid to inflate a balloon.

Any of the handle assemblies of the tools described herein and in the patent applications incorporated herein by reference may comprise a rotatable handle. Such a rotatable handle may be designed to convert a part of a rotational force exerted by a user to a rectilinear force to draw components of the handle assembly towards each other. One embodiment of a rotatable handle is disclosed in U.S. Pat. No. 5,697,159 (Lindén) titled "Pivoted hand tool," the entire disclosure of which is expressly incorporated herein by reference. Such designs of rotatable handles may be used for handle assemblies including, but not limited to the handle 252 and trigger 256 in FIG. 3A, and the handle 272 and trigger 278 in FIG. 3B, etc.

Figure 4A:
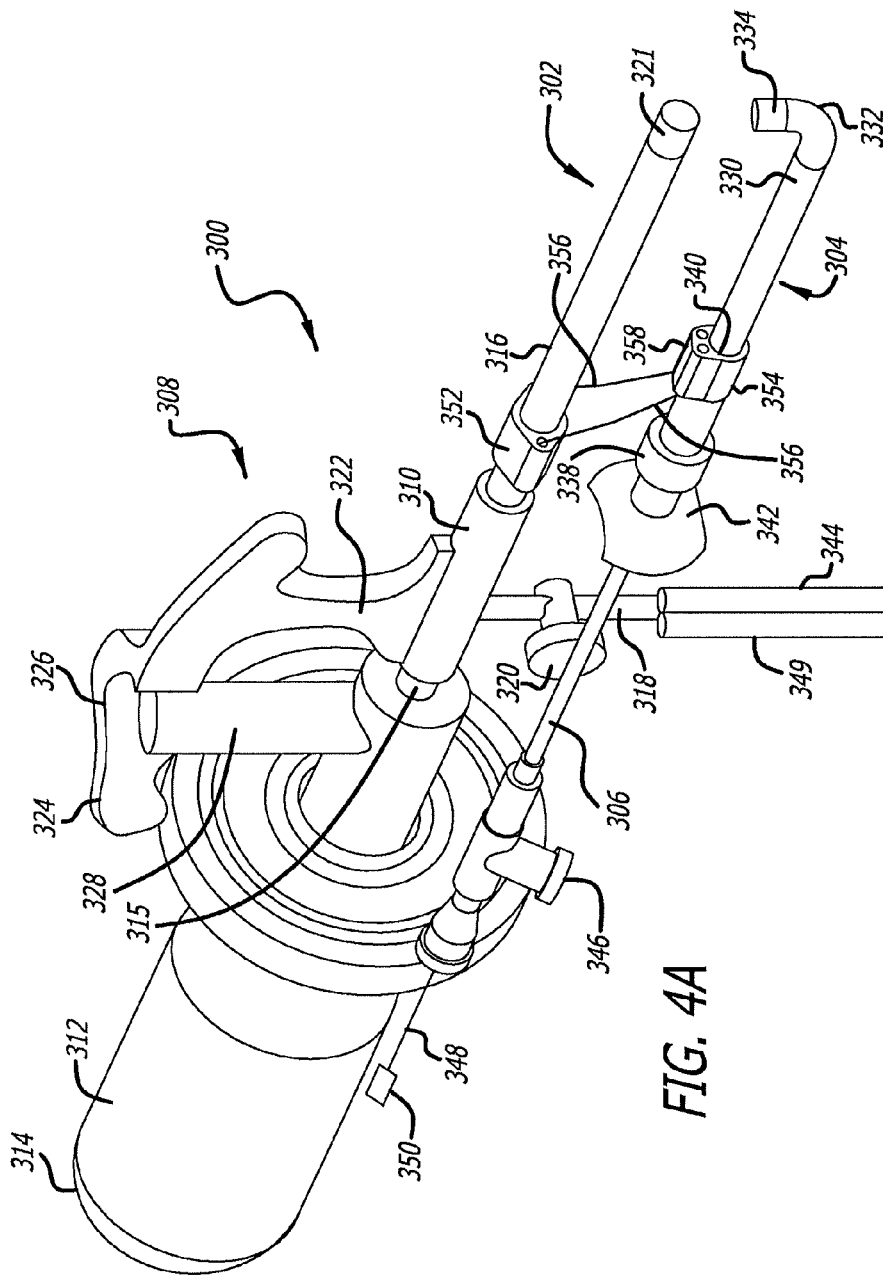
FIG. 4A is a perspective view of an integrated system including an endoscope attached to a guide catheter.

Referring now to FIG. 4A, one embodiment of a balloon sinuplasty and endoscope integrated system 300 is shown. The integrated system 300 includes an endoscope 302 in connection with a guide catheter 304 and a balloon catheter 306. A handle 308 is also included with the system, and the handle has a shaft 310 with a lumen therethrough. The endoscope 302 is shown to include an endoscope handle 312 on a proximal end 314 and is disposed through the lumen of the shaft 310. In one embodiment, an endoscope sheath 316 is connected to or disposed through the lumen of the shaft 310 to cover the elongate shaft of the endoscope 302 for allowing the endoscope lens to be cleaned with fluid without removing the endoscope from the system or its current position with the body of a patient. To clean the lens of the endoscope 302, a fluid line 318 is in communication with the endoscope sheath 316, and a fluid valve 320 disposed on the fluid line allows the sheath to be flushed at any time by opening the fluid valve. The endoscope sheath 316 includes an atraumatic tip 321 to prevent damage to the patient and to keep the lens of the endoscope 302 clean. There may also be a frictional seal 315 on the handle 308 that seals the proximal end of the endoscopic sheath 316 to prevent fluid from leaking back through the handle.

The handle 308 includes a front finger cut-out 322 and a back cut-out 324, which allows the physician to grasp the handle and the endoscope 302 and balance the weight of the endoscope on four fingers to take the pressure off of the thumb. As shown in FIG. 4A, there is also a post cut-out 326 on the top of the handle that allows a light post 328 of the endoscope to exit vertically if the user desires. Alternatively, the light post 328 of the endoscope 302 can hang straight down or out to the side without being constrained by the handle 308.

Still referring to FIG. 4A, the guide catheter 304 of the integrated system 300 includes a hypotube 330 and an elongate tubular element 332 extending out of the hypotube. The elongate tubular element 332 may also include an atraumatic tip 334 at a distal end 336 of the guide catheter. A hub 338 is disposed at a proximal end 340 of the guide catheter 304, and the hub includes a flange 342 and provides an opening for the balloon catheter 306 to enter into the guide catheter 304. The hub 338 is also in communication with a suction line 344 that when activated can suction fluid out of a target area through the guide catheter 304. The balloon catheter 306 includes a balloon inflation port 346 to inflate a balloon disposed on the balloon catheter. The balloon catheter 306 can slide through the hub 338 and the guide catheter 304. Balloon inflation port 346 is connected to an inflation tubing 349 and a suitable inflating device to inflate the balloon of the balloon catheter 306. In one embodiment, the balloon catheter 306 is introduced into a desired region of the anatomy over a guidewire 348. The proximal region of the guidewire 348 may include a torquing device 350 that can be manipulated by a user to rotate, advance, retract or torque the guidewire.

To connect the endoscope 302 with the guide catheter 304, an endoscope clip 352 is disposed on the endoscope sheath 316 and a guide clip 354 is disposed on the hypotube 330 of the guide catheter 304. In embodiments that do not include the endoscope sheath 316, the endoscope clip 352 may be disposed directly on the elongate shaft of the endoscope. A clip connector 356 joins the endoscope clip 352 and the guide clip 354 together to form the integrated system. In one embodiment, the endoscope clip 352 and the guide clip 354 are frictionally fit to the sheath 316 and the hypotube 330, respectively, and the clips 352 and 354 can be rotated and slid in any direction. In another embodiment, one or both of the clips 352 and 354 can include a spring latch or other locking mechanism to lock the clips in place along the devices. It has also been contemplated that the clips 352 and 354 may include a slit 358 for easily removing the clips from the endoscope or guide catheter. In one embodiment, the clip connector 356 is a malleable wire attached to each clip 352 and 354. The malleable wire allows for relatively easy positioning and prevents spring back. Also, the malleable wire allows the guide catheter 304 to be angled in relation to the endoscope 302 for easy wiring of the targeted sinus. In some embodiments, the clip connector 356 includes two linkages for stability, however, one linkage may also be used.

Still referring to FIG. 4A, one embodiment is shown where the tubing 318, 344 and 349 is bonded together to prevent the tubes from becoming entangled. However, in other embodiments, any two of the tubes 318, 344 or 349 may be bonded together. Still in other embodiments, the tubes 318, 344 and 349 are not bonded together.

The integrated system 300 shown in FIG. 4A allows continuous visualization of patient anatomy, such as a target paranasal sinus ostium, with the endoscope in one hand while freeing the user's other hand for guidewire manipulation and catheter balloon advancement. This system also allows the guide catheter 304 to be positioned and then remain static at a set position at or near the target sinus to gain stability during the procedure. Further, the handle allows the user to hold the endoscope without resting the entire weight of the endoscope on the thumb of the user, thus, helping to prevent cramping of the user's hand.

Figure 4B:
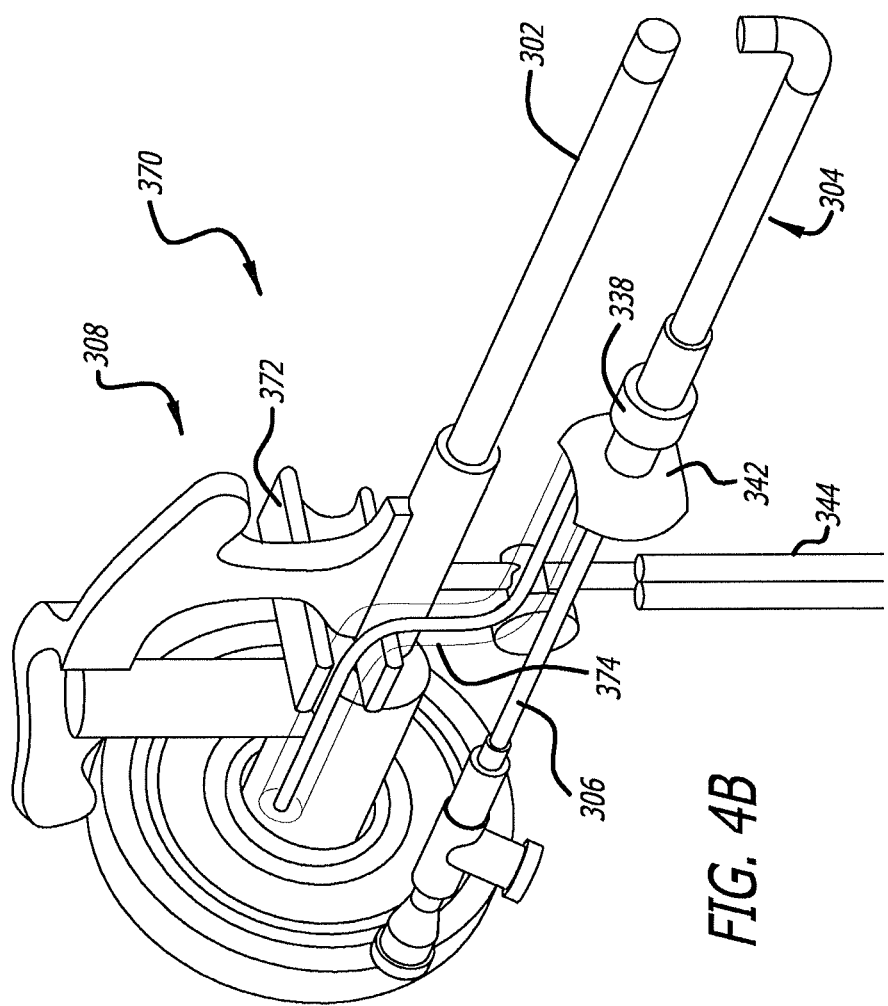
FIG. 4B is a perspective view of another embodiment of an integrated system including an endoscope in connection with a guide catheter.

An alternative embodiment of an integrated system 370 is shown in FIG. 4B. In this embodiment the handle 308 includes an extension clip 372 for attaching an extension 374 that is connected to the guide catheter 304. In this embodiment, the extension 374 is attached to the flange 342 of the hub 338 connected to the guide catheter 304. When the extension 374 is attached to the extension clip 372 of the handle 308, the endoscope is removably connected to the guide catheter 304 and balloon catheter 306. As shown in FIG. 4B, the extension 374 includes a double curved shape that can be held by the user in one hand. It has been contemplated that the extension 374 can slide in and out of the extension clip 372, but does not have to be held by the user when the extension is disposed within the extension clip.

The integrated systems 300 and 370 of FIGS. 4A and 4B can be used in a similar manner for dilating an anatomical region. In use, the integrated system 300 and 370 is introduced in the anatomy. In one embodiment, the endoscope 302 and guide catheter 304 are introduced together through a nostril of a patient and/or through a manmade opening into a paranasal sinus. The endoscope 302 and guide catheter 304 are positioned such that the distal tip of guide catheter 304 is located near an anatomical region to be accessed and the endoscope can view the targeted anatomical region. Thereafter, the guidewire 348 is introduced through guide catheter 304 such that the distal tip of the guidewire is located near the targeted anatomical region. During this step, the guidewire 348 may be navigated through the anatomy using the torquing device 350. In one embodiment, the guidewire 348 is positioned across a paranasal sinus ostium to be dilated. Thereafter, the balloon catheter 306 is advanced over the guidewire 348 into the anatomy by pushing the balloon catheter in the distal direction. Once the balloon of the balloon catheter 306 is correctly positioned, the balloon catheter 306 is used to perform a diagnostic or therapeutic procedure. In one embodiment, the balloon catheter 306 is used to dilate an opening leading to a paranasal sinus such as a paranasal sinus ostium. Once the procedure is complete, the integrated system 300 or 370 is removed from the targeted anatomical region and the patient.

Figure 5A:
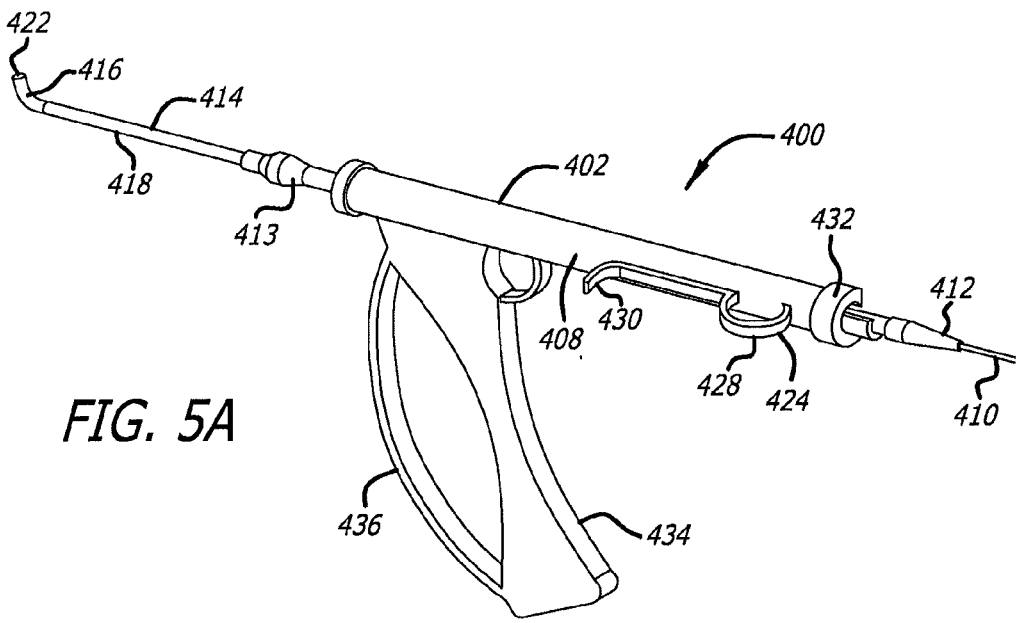
FIG. 5A is a perspective view of a surgical hand tool useable to dilate the ostia or paranasal sinuses and other anatomical passages within the ear, nose and throat.
Figure 5B:
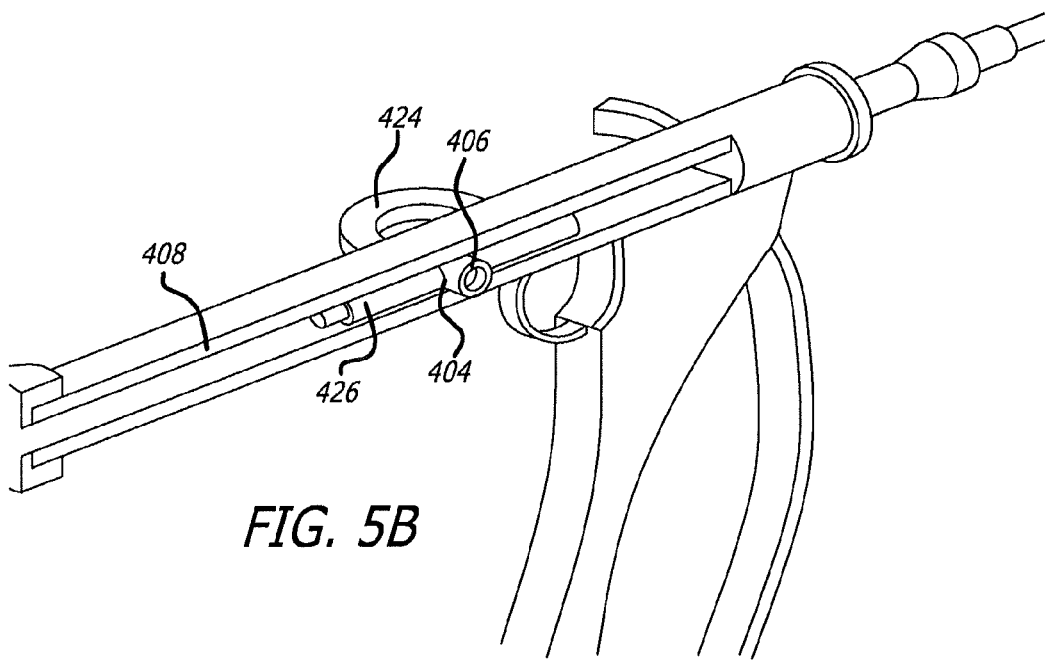
FIG. 5B is a cross-section view of the surgical hand tool shown in FIG. 5A.

Referring now to FIGS. 5A and 5B, one embodiment is shown of a surgical hand tool 400 incorporating a guide catheter and a balloon catheter. The surgical hand tool 400 includes a hollow proximal body 402 made of biocompatible materials including, but not limited to ABS, nylon, polyurethane, polyethylene, etc. Proximal body 402 encloses a balloon catheter 404 (see FIG. 5B). Balloon catheter 404 includes a balloon inflation port 406 to inflate a balloon on the balloon catheter. The balloon inflation port 406 emerges out of proximal body 402 through a longitudinal opening or slit 408 through proximal body such that balloon catheter 404 can slide along the axis of proximal body, as best shown in FIG. 5B. Balloon inflation port 406 is connected to a suitable inflating device via an inflation tubing to inflate the balloon of balloon catheter 404. In this embodiment, the balloon catheter 404 is introduced into a desired region of the anatomy over a guidewire 410. In the embodiment shown, the guidewire 410 is locked to the balloon catheter 404 with a wire lock 412, which is attached to the proximal end of the balloon catheter. The wire lock 412 can be rotated in one direction to lock the guidewire 410 onto the balloon catheter and rotated in the other direction to unlock the guidewire from the balloon catheter. In some embodiments, the proximal region of guidewire 410 may include a torquing device (not shown) to rotate, advance, retract, or torque the guidewire.

The distal region of proximal body 402 includes a suitable hub 413 that allows a guide catheter 414 to attach to proximal body 402. In an alternate embodiment, the guide catheter 414 is permanently attached to proximal body 202. In this embodiment, the guide catheter 414 includes an elongate tubular element 416 made of suitable biocompatible materials including, but not limited to PEEK, Pebax, Nylon, Polyimide, ABS, PVC, polyethylene, etc. The proximal region of the tubular element 416 may be covered by a hypotube 418 made of suitable biocompatible metals or polymers. The proximal end of tubular element 416 is attached to the hub 413. The hub 413 allows the reversible attachment of the guide catheter 414 to proximal body 402. In one embodiment, the hub 413 is a female Luer lock that attaches to a suitable hub on the proximal body 402. Thus, various guide catheters can be attached to the distal region of the proximal body 402 to provide access to various anatomical regions. The distal end of tubular element 416 may comprise an atraumatic tip 422. In certain embodiments, the distal end of tubular element 416 may comprise a curved, bent or angled region.

As shown in FIGS. 5A and 5B, the surgical hand tool 400 includes a slide or device advancing member 424 that is disposed partially within the proximal body 402. The slide 424 includes a generally cylindrical body 426 that holds the balloon catheter 404 at the inflation port 406 and is sized to prevent the slide from falling out of the proximal body 402. Moving the slide advances the balloon catheter 404 and guidewire 410 together when the guidewire is locked onto the balloon catheter. Any steering of the balloon catheter 404 and/or guidewire 410 is achieved by moving the surgical hand tool 400. There is a first grip 428 and a second grip 430 for users with different sized hands to reach and move the slide 424. A back cap 432 is disposed at the proximal end of the proximal body 402 to prevent the slide 424 from being removed from the proximal body. In the embodiment shown, a handle 434 attached to the proximal shaft 402 includes a finger guard 436 that allows the fingers of the user to be pressed forward if desired for extra control.

In an alternative embodiment to the one shown in FIGS. 5A and 5B, hollow proximal body 402 may be replaced my a rail body. The rail would provide a structure along which slide 424 could slide and catheter 404 and/or guidewire 410 could be advanced.

Another embodiment of a surgical hand tool 440 is shown in FIGS. 6A and 6B. The surgical hand tool 440 is similar to the surgical hand tool 400 shown in FIGS. 5A and 5B, however, surgical hand tool 440 is designed to allow the balloon catheter and guidewire to rotate using the slide. As shown in FIGS. 6A and 6B, the surgical hand tool 440 includes a hollow proximal body 442 made of biocompatible materials including, but not limited to ABS, nylon, polyurethane, polyethylene, etc. Proximal body 442 encloses a balloon catheter 444 (see FIG. 6B). Balloon catheter 444 includes a balloon inflation port 446 to inflate a balloon disposed on the balloon catheter. The balloon inflation port 446 emerges out of proximal body 442 through a slot or longitudinal opening 448 cut through the proximal body such that balloon catheter 444 can slide along the axis of proximal body, as best shown in FIG. 5B. Balloon inflation port 446 is connected to a suitable inflating device via an inflation tubing to inflate the balloon of balloon catheter 444. In this embodiment, the balloon catheter 404 is introduced into a desired region of the anatomy over a guidewire 450. In the embodiment shown, the guidewire 450 is locked to the balloon catheter 404 by a wire lock 452, which is attached to the proximal end of the balloon catheter. The wire lock 452 can be rotated in one direction to lock the guidewire 450 onto the balloon catheter and rotated in the other direction to unlock the guidewire from the balloon catheter. In some embodiments, the proximal region of guidewire 450 may include a torquing device (not shown) to rotate, advance, retract, or torque the guidewire.

The distal region of the proximal body 442 includes a suitable hub 453 that allows a guide catheter 454 to connect to the proximal body 442. In an alternate embodiment, the guide catheter 454 is permanently attached to the proximal body 442. In this embodiment, the guide catheter 454 includes an elongate tubular element 456 made of suitable biocompatible materials including, but not limited to PEEK, Pebax, Nylon, Polyimide, ABS, PVC, polyethylene, etc. The proximal region of the tubular element 456 may be covered by a hypotube 458 made of suitable biocompatible metals or polymers. The proximal end of tubular element 456 is attached to the hub 453. The hub 453 allows the reversible attachment of the guide catheter 454 to the proximal body 442. In one embodiment, the hub 453 is a female luer lock that attaches to a suitable hub on proximal body 442. Thus, various guide catheters can be attached to the distal region of proximal body 442 to provide access to various anatomical regions. The distal end of tubular element 456 may comprise an atraumatic tip 462. In certain embodiments, the distal end of tubular element 456 may comprise a curved, bent or angled region.

As shown in FIGS. 6A and 6B, the surgical hand tool 440 includes a slide or device advancement member 464 that moves within the proximal body 442. The slide 464 includes a generally cylindrical bottom portion 466 that holds the balloon catheter 444 at the inflation port 446 and is sized to prevent the slide from falling out of the proximal body 442. Moving the slide advances the balloon catheter 444 and guidewire 450 together when the guidewire is locked onto the balloon catheter. The size of the slot or longitudinal opening 448 in this embodiment allows the user to rotate, and hence steer, the balloon catheter and guidewire with the slide between about thirty to sixty degrees in both directions for a total rotational freedom of between about sixty and one-hundred and twenty degrees. However, the rotation of the slide can be from about zero degrees to about ninety degrees in both directions for a total freedom of rotation between about zero degrees and about one-hundred and eighty degrees. Steering may also be accomplished by moving the surgical had tool 440. In this embodiment, there are multiple grips 468 extending from the slide 464 on either or both sides for user's with different sized hands to reach and move the slide 424. A mount 469 of the slide 464 attaches the grips 468 together. In another embodiment, the grips 468 could be replaced with loops that extend over the proximal body 442. A back cap 472 is disposed at the proximal end of the proximal body 442 to prevent the slide 464 from being removed from the proximal body. In the embodiment shown, a handle 474 attached to the proximal shaft 442 includes a finger guard 476 that allows the fingers of the user to be pressed forward if desired for extra control.

In this embodiment shown in FIGS. 6A and 6B, the surgical hand tool also includes a mount bottom 478 attached towards the proximal end of the slide 464 to allow for the longest possible travel of the balloon catheter 444 along the proximal body 442. There is also a cut-out 480 on the proximal body 442 that allows the slide 464 to be rotate a few extra degrees to allow removal and replacement of the balloon catheter with another balloon catheter. When the slide 464 is rotated into the cut-out 480, the balloon catheter can be removed from the cylindrical bottom portion 466 of the slide. With the slide still in this position, another balloon catheter may be inserted into the cylindrical bottom portion 466 of the slide for use with the surgical hand tool.

Figure 7:
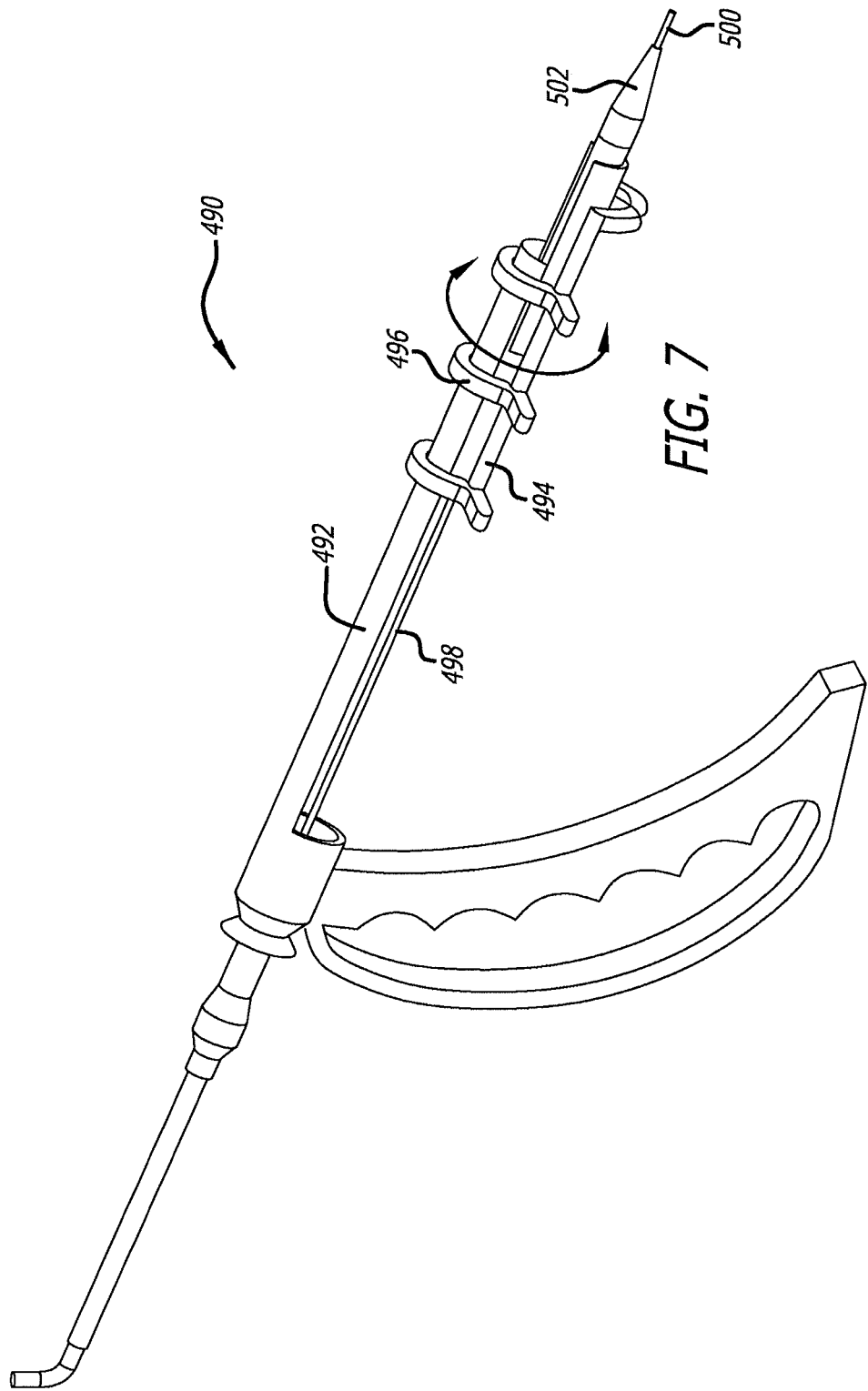
FIG. 7 is a perspective view of another embodiment of a surgical hand tool capable of rotating a catheter and a guidewire.

Another embodiment of a surgical hand tool 490 is shown in FIG. 7 and is similar to the embodiment shown in FIGS. 6A and 6B. In this embodiment, the proximal body is replaced with a rail 492 that allows greater rotation of a slide 494. The rotation of the slide 494 can range from about one-hundred and fifty degrees to about two-hundred and eighty degrees of total rotational freedom. The slide 494 includes overhead loops 496 that constrain the slide to the rail 494 and provide grips for the user to move the slide along the rail, which in turn moves a balloon catheter 498 and guidewire 500 locked by a wire lock 502.

Figure 8A:
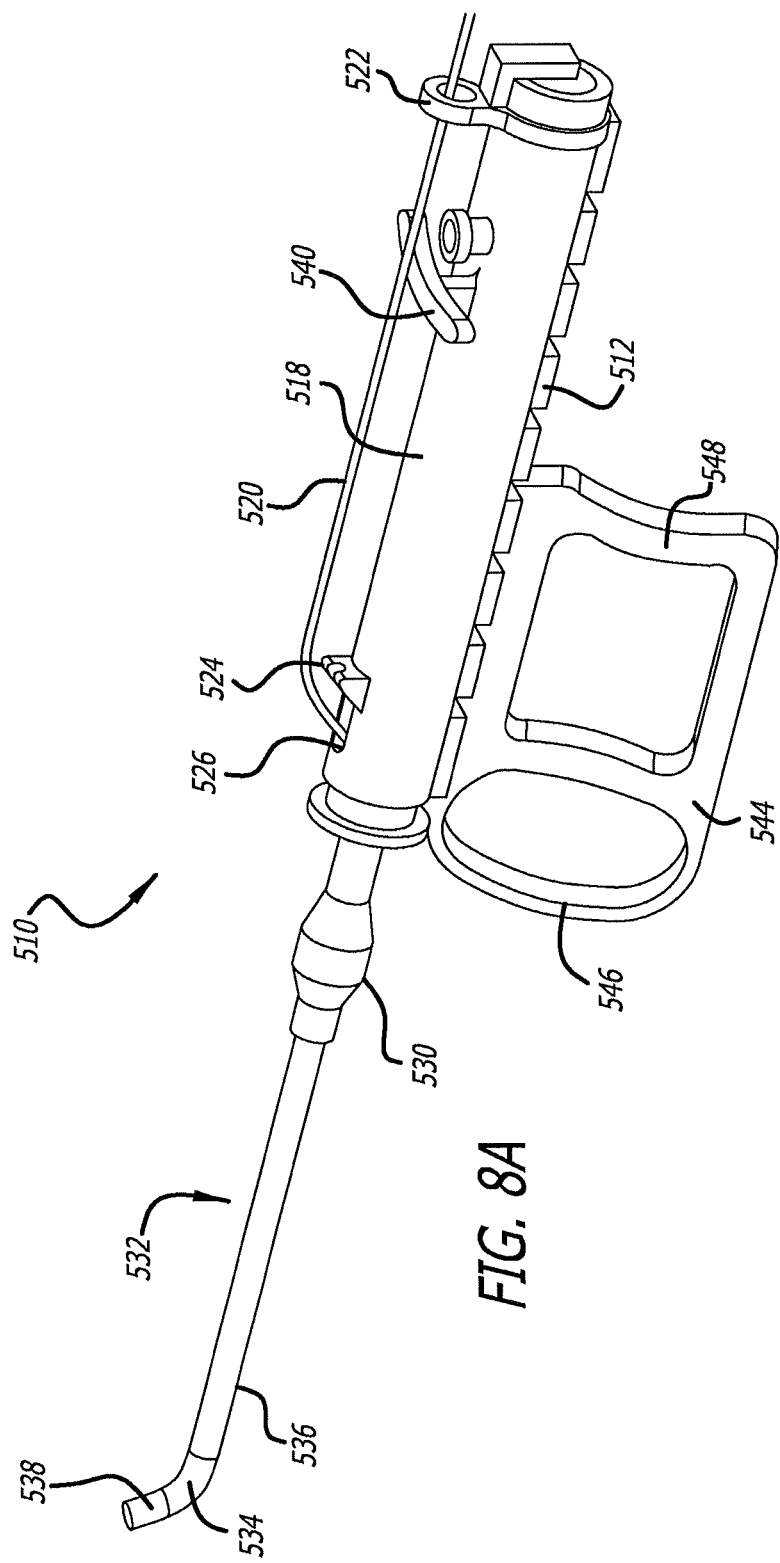
FIG. 8A is a perspective view of yet another embodiment of a surgical hand tool.

Yet another embodiment of a surgical hand tool 510 is shown in FIGS. 8A and 8B, which allows one handed control of the balloon sinuplasty device. The surgical hand tool 510 includes a hollow proximal body 512 made of biocompatible materials including, but not limited to ABS, nylon, polyurethane, polyethylene, etc. Proximal body 512 encloses a balloon catheter 514 (see FIG. 8B). Balloon catheter 514 includes a balloon inflation port 516 to inflate a balloon disposed on the balloon catheter. The balloon inflation port 516 emerges out of proximal body 512 through a longitudinal slit or opening 518 through the proximal body such that balloon catheter 404 can slide along the axis of the proximal body. Balloon inflation port 516 is connected to a suitable inflating device via an inflation tubing to inflate the balloon of balloon catheter 514. In this embodiment, the balloon catheter 514 is introduced into a desired region of the anatomy over a guidewire 520.

The guidewire 520 is fed through a proximal loop 522 attached to the proximal end of the proximal body 512, over a wire ramp 524, and into a wire slot 526 of the proximal body. The guidewire 520 is positioned above the proximal body 512 allowing a user to control the guidewire behind the guide catheter using a thumb and index finger. The proximal loop 522 prevents the guidewire from drifting to the left or right, and can be rotated around the proximal body 512. The wire ramp 524 keeps the position of the guidewire 520 and is used to hold the guidewire during balloon catheter advancement. Passing through the wire slot 526, the guidewire 520 enters the balloon catheter 514 through an opening 528 on the side of the balloon catheter. This type of catheter, such as a rapid exchange catheter, is known in the art.

The distal region of the proximal body 512 includes a suitable hub 530 that allows a guide catheter 532 to attach to the proximal body 512. In an alternate embodiment, the guide catheter 532 is permanently attached to the proximal body 512. In this embodiment, the guide catheter 532 includes an elongate tubular element 534 made of suitable biocompatible materials including, but not limited to PEEK, Pebax, Nylon, Polyimide, ABS, PVC, polyethylene, etc. The proximal region of the tubular element 534 may be covered by a hypotube 536 made of suitable biocompatible metals or polymers. The proximal end of tubular element 534 is attached to the hub 530. The hub 530 allows the reversible attachment of the guide catheter 532 to proximal body 512. In one embodiment, the hub 530 is a female Luer lock that attaches to a suitable hub on proximal body 512. Thus, various guide catheters can be attached to the distal region of proximal body 512 to provide access to various anatomical regions. The distal end of tubular element 534 may comprise an atraumatic tip 538. In certain embodiments, the distal end of tubular element 534 may comprise a curved, bent or angled region. It has also been contemplated that guide catheter 532 is frictionally fit into the hub 530 such that the guide catheter has the ability to rotate within the hub, but still have enough friction in the mechanism to allow it to stay in place once properly adjusted.

As shown in FIGS. 8A and 8B, the surgical hand tool 510 includes a balloon driver 540 that is disposed partially within the proximal body 512 and extends through the longitudinal slit or opening 518. The balloon driver 540 includes a balloon driver latch 542 (FIG. 8B) that holds the balloon catheter 514 at the inflation port 516. Moving the balloon driver 540 in the distal direction advances the balloon catheter 514 forward. When advancing the balloon catheter forward, the guidewire 520 can be held against the ramp 524. Any steering of the balloon catheter and/or guidewire is achieved by moving the surgical hand tool 510. In the embodiment shown, a handle 544 attached to the proximal shaft 512 includes a front portion 546 that is gripped preferably by the fourth and fifth fingers of the user for stabilization. When holding the device, the user's palm is preferably pressed against a back portion 548 of the handle for stabilization.

The surgical hand tool 510 shown in FIGS. 8A and 8B allows the user to hold the device in the palm of the hand, balance the device with preferably the fourth and fifth fingers, and advance the guidewire 520 with the index finger and thumb. In this manner, the surgical hand tool 510 is held in the same hand that is used to control the guidewire 520. Further, the user has direct access to the guidewire giving full tactile feel during advance and steering of the guidewire. Balloon catheter 514 advancement is then achieved by reaching back with the thumb and pushing the balloon driver 540 forward (distally). The guidewire can then be retracted using the index finger and thumb, and the balloon catheter 514 can be retracted by pulling the balloon driver 540 in the proximal direction.

Figure 9A:
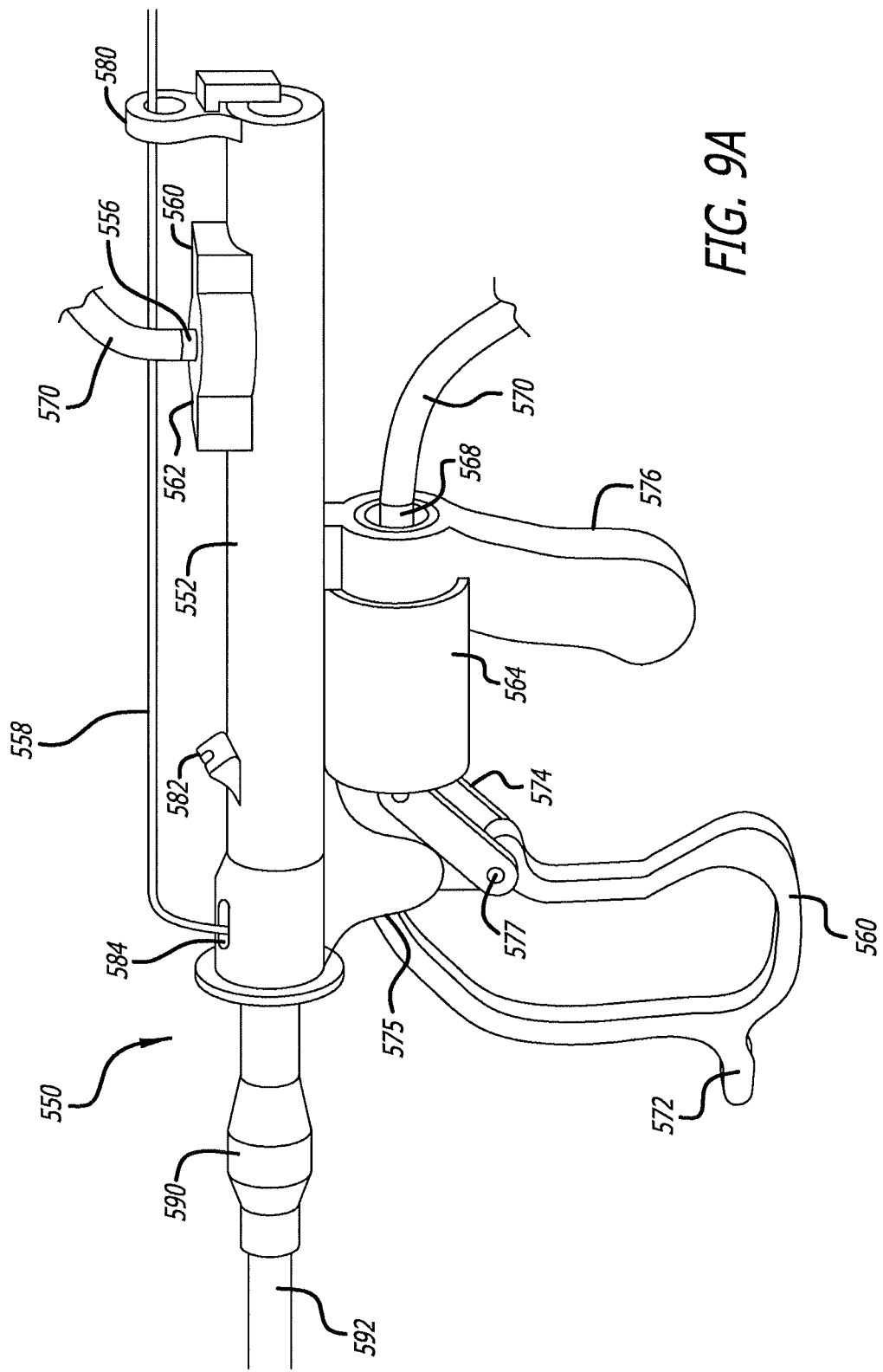
FIG. 9A is a perspective view of another embodiment of a surgical hand tool including a fluid reservoir.
Figure 9B:
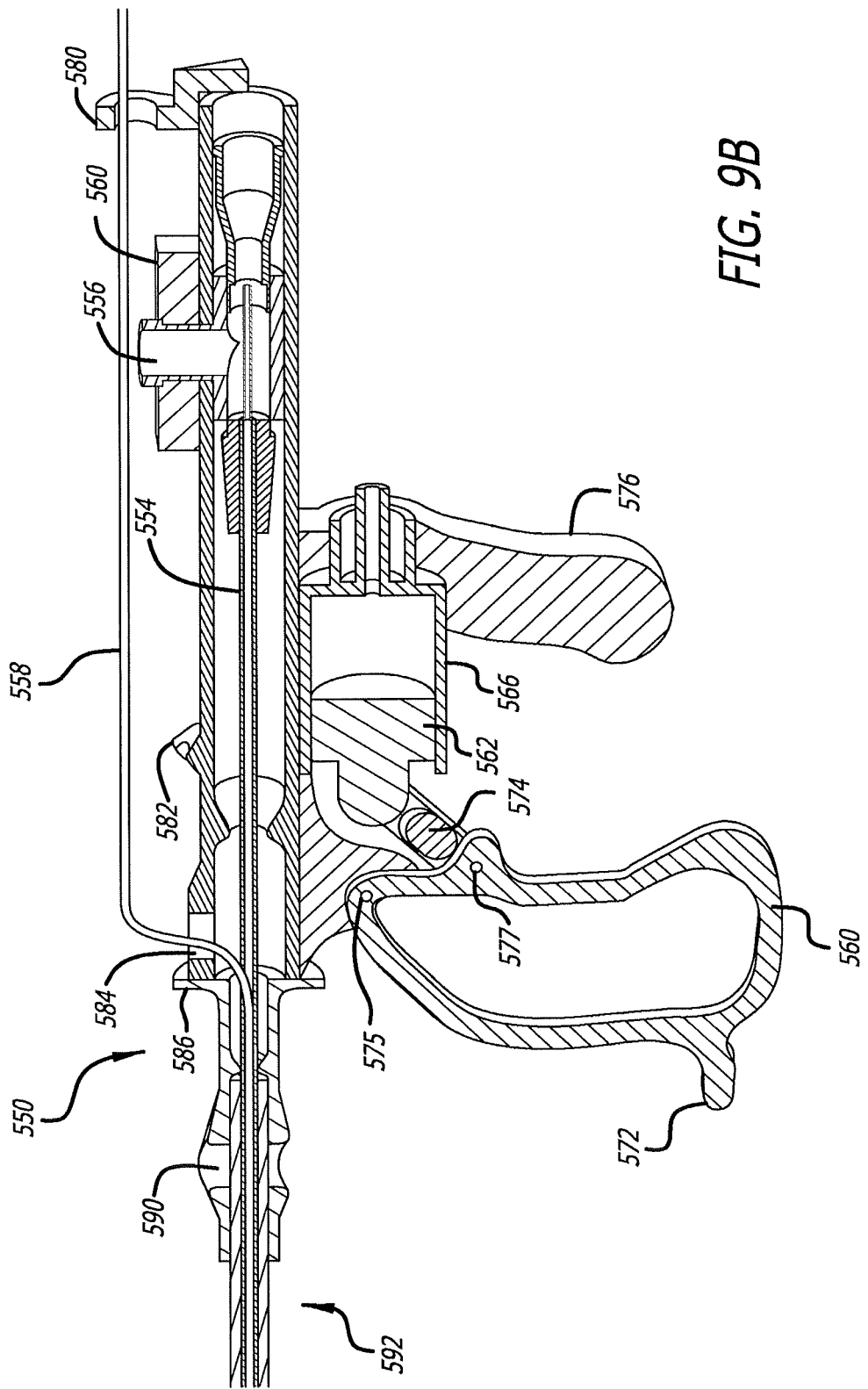
FIG. 9B is a cross-section view of the surgical hand tool shown in FIG. 9A.

Still further, another embodiment of a surgical hand tool 550 is shown in FIGS. 9A and 9B, which allows one handed control of the balloon sinuplasty device and fluid delivery to an inflation device. The surgical hand tool 550 includes a hollow proximal body 552 made of biocompatible materials including, but not limited to ABS, nylon, polyurethane, polyethylene, etc. Proximal body 552 encloses a balloon catheter 554 (see FIG. 9B). Balloon catheter 554 includes a balloon inflation port 556 to inflate a balloon disposed on the balloon catheter. The balloon inflation port 556 emerges out of proximal body 552 through a longitudinal slit or opening 558 in the proximal body such that balloon catheter 554 can slide along the axis of proximal body. The balloon inflation port 556 also extends through and is held by a balloon driver or device advancement member 560 that is used to move the balloon catheter in both the distal and proximal directions. A handle 562 of the balloon driver 560 can be turned to either side of the surgical hand tool 550 depending on the user's desire, and can be clamped in place when a fluid line is attached to the inflation port 556 of the balloon catheter 554. In this embodiment, the balloon catheter 554 is introduced into a desired region of the anatomy over a guidewire 558.

An inflation balloon (not shown) disposed on a distal region of the balloon catheter 554 can be used to dilate one or more regions of the anatomy. The balloon is inflated from an unexpanded configuration to an expanded configuration by an actuation handle or trigger 560 attached to the proximal body 552. The actuation handle 560 is connected to a plunger 562 that is further connected to a fluid barrel 564 including an inflation fluid reservoir 566. Fluid (water, saline, etc.) stored in the inflation fluid reservoir 566 can be used to inflate the balloon of the balloon catheter, to flush a vortex, or provide fluid wherever desired. During a procedure, a user inflates the balloon of the balloon catheter to a desired pressure using the inflating fluid stored in the inflation fluid reservoir 566. The pressure in the balloon can be measured with a pressure sensor or gauge (not shown) that is in fluid communication with the inflating fluid within the balloon. In one embodiment, the surgical hand tool 550 is designed to inflate the balloon of the balloon catheter to a fixed pressure. Alternatively, the tool may be designed to deliver a fixed volume of inflating fluid to inflate the balloon.

The fluid barrel 564 includes a barrel port 568 that provides a structure for attaching a fluid line 570 from the fluid barrel to the balloon catheter 554 and the inflating balloon. In other embodiments, the barrel port 568 may extend at an angle and from any location on the fluid barrel. The fluid line 570 extends from the barrel port 568 to the inflation port 556 of the balloon catheter in this embodiment.

The actuation handle 560 is designed to accommodate one to three fingers of the user depending on the user's comfort and hand size. In addition to actuating the fluid mechanism of this device, the actuation handle acts to stabilize the device during placement of the guidewire, deploying the balloon, vortex deployment, or deployment of other devices. As shown in FIGS. 9A and 9B, the handle includes an outer finger flange 572 to provide a structure to stabilize the device for users with larger hands. The outer finger flange can also allow a user to provide extra torque if needed or required for actuating the fluid mechanism. A rotating hinge 574 attached between the actuating handle 560 and the plunger 562 delivers the motion and applied force of the actuating handle to the plunger. In other embodiments, the rotating hinge can be curved to more easily reach into the fluid barrel 564 during actuation of the handle 560 and avoid constraints. It has also been contemplated that the pivot points on the hinge 574, actuating handle 560, and plunger 562 can be moved closer or farther apart depending on the distance traveled of the plunger versus rotation of the handle and applied torque is desired or required. The actuation handle pivot point 575 attaches the handle to the proximal body 552. To maximize the distance the plunger travels and the amount of torque applied with the handle, the handle pivot point is disposed level with the center of the connection between the rotating hinge 574 and the plunger 562.

In one embodiment, a spring (not shown) may be embedded in the proximal body 552 of the device to bias the actuation handle 560 back into an extended or open position away from the fluid barrel 564 after the handle has been squeezed to inflate the balloon of the balloon catheter. The spring may be a torsion spring disposed around the handle pivot point 575 or around a handle/hinge pivot 577. Alternatively, the spring may be a leaf spring disposed between two members or points of the device, such as points 575 and 577. Still in other embodiments, the spring may be a coiled spring (tension or compression).

As shown in FIGS. 9A and 9B, the surgical hand tool 550 also includes a back handle 576 that rests against a user's palm Unlike the handles of other embodiments, the back handle 576 is open at the bottom, which allows a user to more freely manipulate the device.

In the embodiment shown in FIGS. 9A and 9B, the guidewire 558 is fed through a proximal loop 580 attached to the proximal end of the proximal body 552, over a wire ramp 582, and into a wire slot 584 of the proximal body. The guidewire 558 is positioned above the proximal body 552 allowing a user to control the guidewire behind the guide catheter. The proximal loop 580 prevents the guidewire from drifting to the left or right, and can be rotated around the proximal body 552. The wire ramp 582 keeps the position of the guidewire 582 and is used to hold the guidewire during balloon catheter advancement. Passing through the wire slot 584, the guidewire 558 enters the balloon catheter 554 through an opening 586 on the side of the balloon catheter. This type of catheter, such as a rapid exchange catheter, is known to those skilled in the art.

The distal region of the proximal body 552 includes a suitable hub 590 that allows a guide catheter 592 to attach to the proximal body 552. In one embodiment, the guide catheter 592 is permanently attached to the proximal body 552. Similar to the embodiments described above, the guide catheter 592 includes an elongate tubular element made of suitable biocompatible materials including, but not limited to PEEK, Pebax, Nylon, Polyimide, ABS, PVC, polyethylene, etc. The proximal region of the tubular element may be covered by a hypotube made of suitable biocompatible metals or polymers. The proximal end of tubular element is attached to the hub 590. The hub 590 allows the reversible attachment of the guide catheter 592 to proximal body 552. In one embodiment, the hub 590 is a female luer lock that attaches to a suitable hub on proximal body 552. Thus, various guide catheters can be attached to the distal region of proximal body 552 to provide access to various anatomical regions. The distal end of tubular element may comprise an atraumatic tip. In certain embodiments, the distal end of tubular element may comprise a curved, bent or angled region. It has also been contemplated that guide catheter 592 is frictionally fit into the hub 590 such that the guide catheter has the ability to rotate within the hub, but still have enough friction in the mechanism to allow it to stay in place once properly adjusted.

The surgical hand tool 550 shown in FIGS. 9A and 9B allows the user to hold the device in the palm of the hand, balance the device with preferably the fourth and fifth fingers, and advance the guidewire 558 with the index finger and thumb. In this manner, the surgical hand tool 550 is held in the same hand that is used to control the guidewire 558. Further, the user has direct access to the guidewire giving full tactile feel during advance and steering. Balloon catheter 554 advancement is then achieved by reaching back with the thumb and pushing the balloon driver 560 toward the distal end of the proximal body 552. The guidewire 558 can then be retracted using the index finger and thumb, and the balloon catheter 554 can be retracted by pulling the balloon driver 560 in the proximal direction.

As shown in FIG. 9A, the fluid line 570 to the balloon inflation port 556 is a simple closed system. When the actuation handle 560 is squeezed or moved proximally, the plunger 562 forces fluid from the reservoir 566 through the fluid line and into the balloon catheter 554. Moving the actuation handle 560 in the distal direction creates a vacuum to deflate the balloon of the balloon catheter 544. Alternatively, in some embodiments a spring disposed in or on plunger 562 may act to deflate catheter 544.

In various embodiments, actuation handle 560 may have any suitable configuration and may be spaced at any distance from other components of hand tool 550, to provide a desired amount of leverage to plunger 562. In some embodiments, plunger 562 may be removable/interchangeable. For example, in one embodiment a first size of plunger 562 may be used to provide high pressure to inflate balloon catheter 544, and a second size of plunger 562 may be used to provide high flow to irrigation fluid to an irrigation catheter coupled with hand tool 550. In some embodiments, device 550 may include a pressure indicator to monitor pressure in plunger 562. Alternatively or additionally, plunger 562 may include a hard stop to prevent applying pressure beyond a certain point.

Figure 9C:
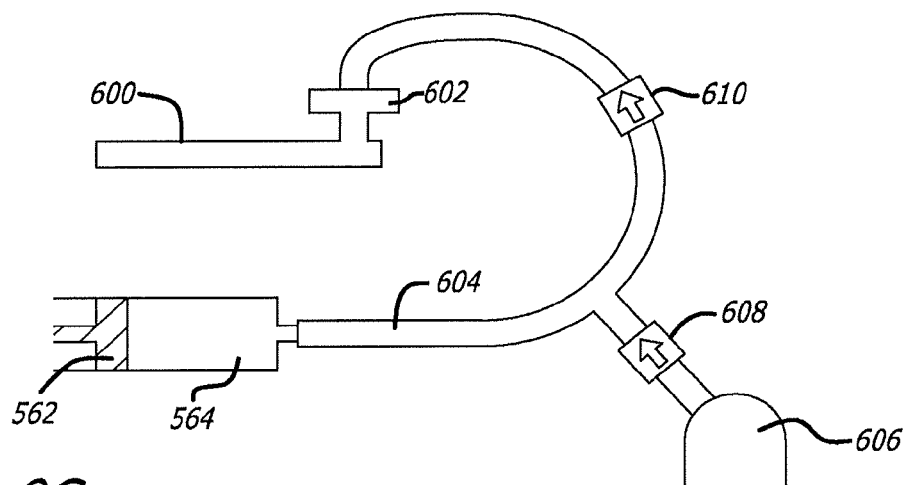
FIGS. 9C through 9E are schematic views of different embodiments of fluid delivery systems for the surgical hand tool shown in FIGS. 9A and 9B.

In another embodiment as shown in FIG. 9C, the fluid delivery system includes two valves. For ease of reference, the proximal body 552 of the device has been removed in FIG. 9C. In this embodiment, the balloon catheter has been replaced with an open ended device 600 (open at the distal end) including an inflation port 602. The device 600 can be used to create a vortex or delivery fluid to a specific region. A fluid line 604 is connected between the fluid barrel 564 and the inflation port 602 and is also in communication with a separate fluid bath 606. The fluid line includes a first valve 608 adjacent the fluid bath 606 and a second valve 610 adjacent to the device 600. In one embodiment, both the first and second valves are one-way valves. By forcing the plunger 562 proximally, by squeezing the handle, the fluid in the fluid barrel 564 is pushed through the fluid line 604 and through the second valve 610 and into the open ended device 600 (a vortex creating device or other fluid delivery device). The first one-way valve 608 prevents fluid from exiting out into the fluid bath 606. Moving the plunger 562 in the distal direction causes fluid to be drawn from the fluid bath 606 and through the first one-way valve 608. The second one-way valve 610 prevents air, fluid, etc., from being drawn into the fluid line from the device 600. In this system, the fluid barrel 564 can be filled from the fluid bath 606 and emptied through the device 600 "continuously" by moving the plunger back and forth (or proximally and distally).

Figure 9D:
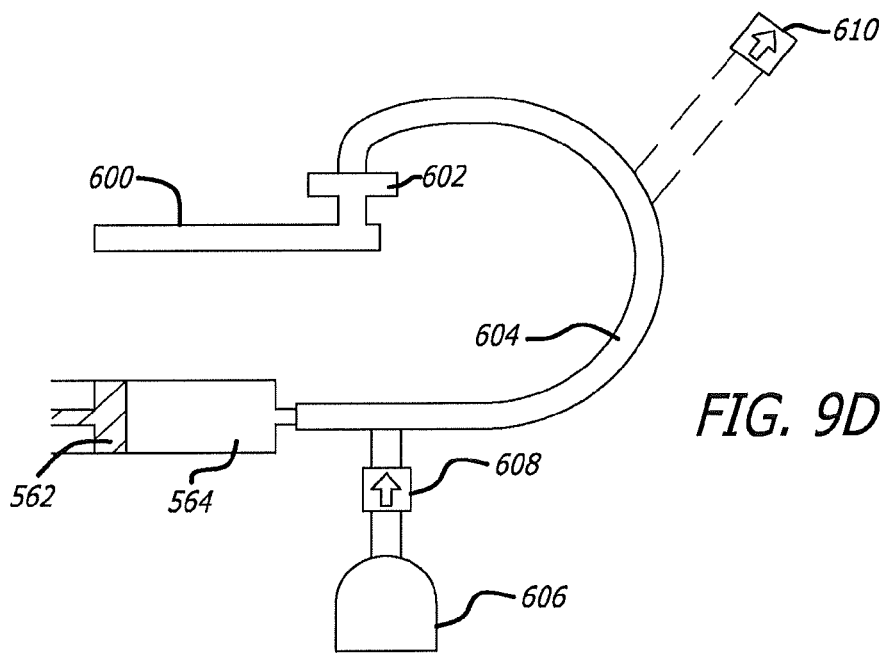

Another embodiment of a fluid delivery system is shown in FIG. 9D. In this embodiment, the fluid line 604 is unattached to the open ended device 600 and connected to the fluid barrel 562 and the separate fluid bath 606. Initially, the fluid line 604 is attached to the second one-way valve 610 and unattached to the device 600, and fluid is drawn from the fluid bath 606 by moving the plunger 562 in the distal direction. Air can be removed through the second one-way valve 610 by pushing the plunger 562 in the proximal direction. Once all of the air in the system is removed, the fluid line 604 can be detached from the second one-way valve 610 and attached to the device 600. Once attached to the device 600, the plunger 562 may be moved proximally to send fluid into and through the device. The second one-way valve 610 prevents the fluid from exiting into the fluid bath 606. It has also been contemplated that a T-valve can be used in place of the first one-way valve to remove the need to detach the fluid line from the device 600.

Figure 9E:
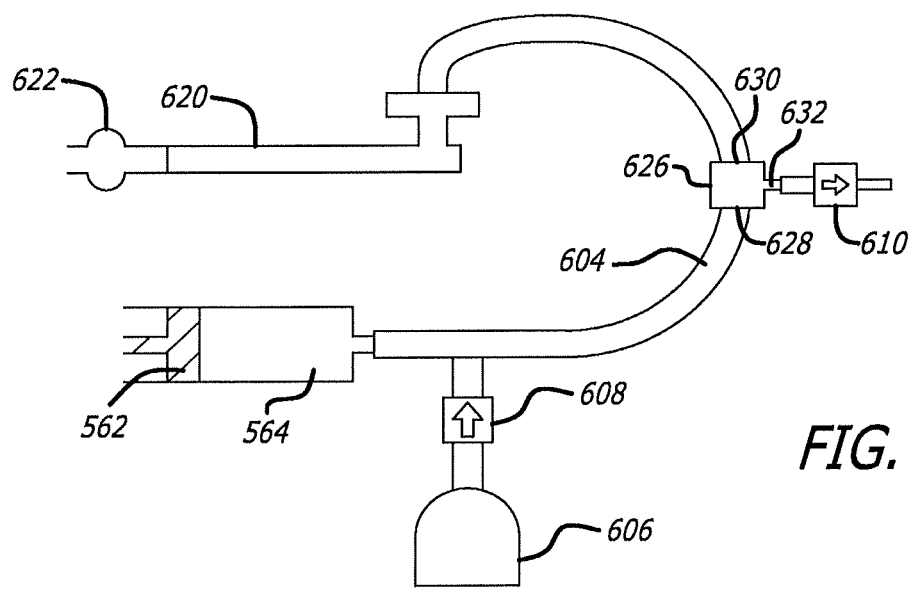

Yet another embodiment of a fluid delivery system is shown in FIG. 9E and is connected to a balloon catheter 620 including an inflatable balloon 622 and an inflation port 624. As shown in FIG. 9E, the fluid line 604 is connected to a T-valve 626 having a first 628, second 630 and third 632 valve. To fill the fluid barrel 564, the plunger 562 is moved distally to draw fluid from the fluid bath 606 into the fluid line 604 through the first one-way valve 608. To remove air in the fluid line 604, the first valve 628 is open, the second valve 630 is closed, and the third valve 632 of the T-valve 626 is open and leads to the second one-way valve 610, which acts as a vent. With this configuration, the plunger 562 is moved proximally to force air in the fluid line 604 out through the second one-way valve 610. Once the air in the system is removed, the balloon 622 can be inflated by first opening the second valve 630 and closing the third valve 632. The first valve 628 remains open. With this configuration, the plunger is moved proximally to force the fluid through the T-valve 626 and into the balloon catheter 620 to inflate the balloon 622. The system can be arranged in other configurations with other valves to fill the fluid barrel 654 with fluid and remove air from the system by moving the plunger 562 in a back and forth motion (proximally and distally).

Figure 10A:
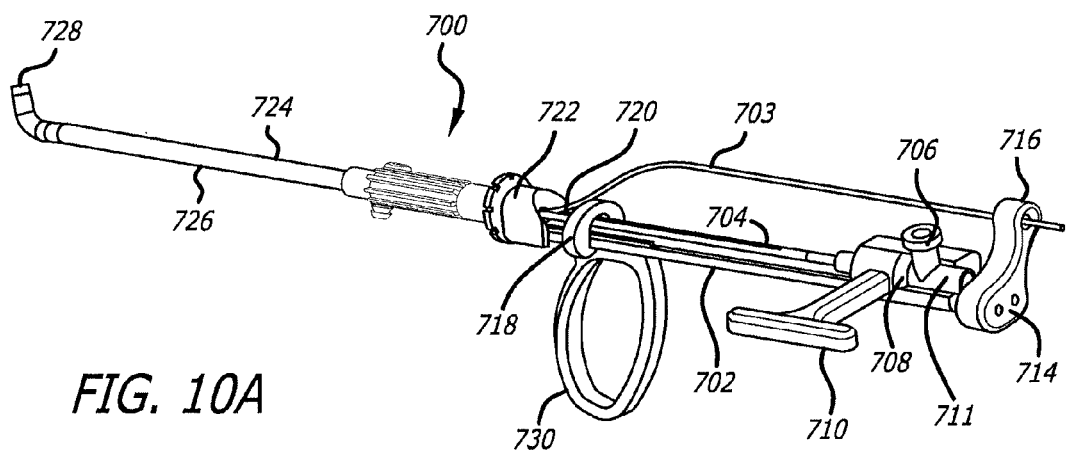
FIG. 10A is a perspective view of another embodiment of a surgical hand tool being supported by rails.
Figure 10B:
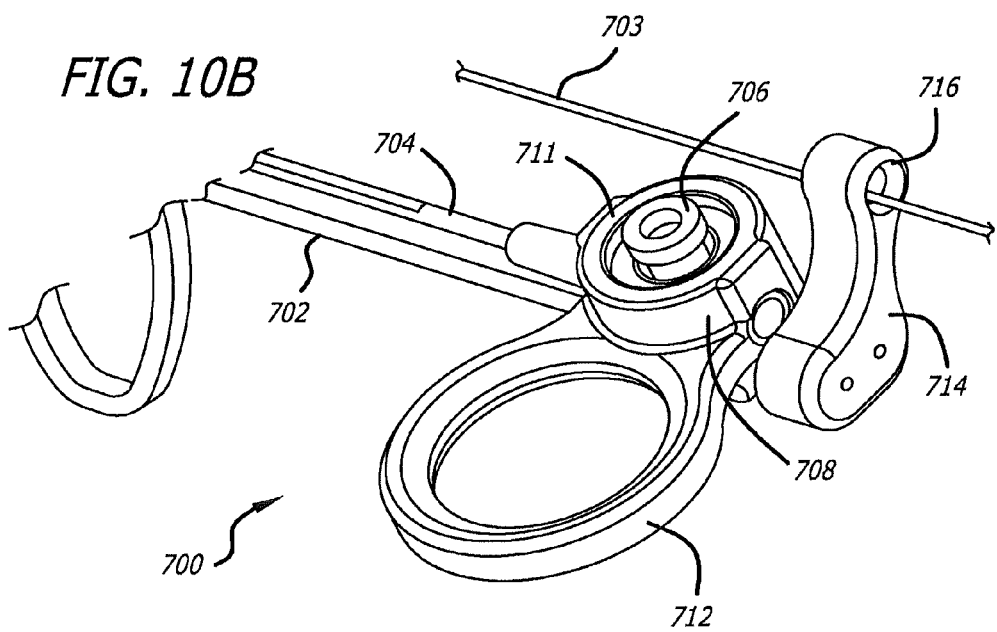
FIG. 10B is a perspective view of a proximal end of a surgical hand tool.

Referring now to FIGS. 10A-10E, alternative embodiments of a surgical hand tool 700 are shown, which allow one handed control of the balloon sinuplasty device. The surgical hand tool 700 includes first and second rails 702 that replace the proximal body of the surgical hand tools described above. These rails 702 may be made of biocompatible materials, including, but not limited to ABS, nylon, polyurethane, polyethylene, etc. Use of rails 702 at the proximal end of the hand tool 700 reduces the profile of the hand tool 700, giving more freedom for the user's index finger and thumb to advance a guidewire 703. A balloon catheter 704 is positioned parallel to the rails 702, and a balloon inflation port 706 of the balloon catheter 704 is secured by a balloon driver 708 of the surgical hand tool 700. Specifically, the balloon inflation port 706 is secured within a friction-fit slot 709 of the balloon driver 708, as shown in FIG. 10A. In another embodiment, the balloon inflation port 706 is secured within a latch 711 of the balloon driver 708, as shown in FIG. 10B. The balloon driver 708 rides along the rails 702 to advance or retract the balloon catheter 704, which provides relatively low friction. As shown in FIG. 10A, the balloon driver 708 includes a T-bar 710 that can be grasped by the user's index finger and thumb to advance or withdraw the balloon catheter. FIG. 10B shows another embodiment of the balloon driver 708 that includes a ring 712 for the user to grasp and advance or withdraw the balloon catheter 704. Balloon inflation port 706 is connected to a suitable inflating device (not shown) via an inflation tubing to inflate the balloon of balloon catheter 704. In this embodiment, the balloon catheter 704 is introduced into a desired region of the anatomy over the guidewire 703.

The surgical hand tool 700 also includes a wire retention member 714 having a loop 716 for retaining the guidewire 703. Also, proximal ends of the rails 702 are attached to the wire retention member 714 to prevent the rails 702 from moving or twisting. In use, the guidewire 703 is fed through the loop 716, over a wire ramp 718, and into the balloon catheter 704. The guidewire 703 is positioned above the rails 702 of the hand tool 700, allowing a user to control the guidewire 703 behind the guide catheter using a thumb and index finger. The loop 716 prevents the guidewire 703 from drifting to the left or right, and the wire ramp 718 keeps the position of the guidewire 703 and is used to hold the guidewire 703 during balloon catheter advancement. The guidewire 703 enters the balloon catheter 704 through an opening 720 on the side of the balloon catheter 704. This type of catheter, such as a rapid exchange catheter, is known in the art.

The distal ends of the rails 702 are connected to a suitable hub 722 that allows a guide catheter 724 to attach to the surgical hand tool 700. In this embodiment, the guide catheter 724 includes an elongate tubular element 726 made of suitable biocompatible materials including, but not limited to PEEK, Pebax, Nylon, Polyimide, ABS, PVC, polyethylene, etc. The proximal region of the tubular element 726 may be covered by a hypotube made of suitable biocompatible metals or polymers. The proximal end of tubular element 726 is attached to the hub 722. The hub 722 allows the reversible attachment of the guide catheter 724 to surgical hand tool 700. The distal end of tubular element 726 may include an atraumatic tip 728. In certain embodiments, the distal end of tubular element 726 may comprise a curved, bent or angled region.

As shown in FIG. 10A, a handle 730 may be attached to the rails 702 of the surgical hand tool 700. The handle 730 is gripped preferably by the fourth and fifth fingers of the user for stabilization. When holding the device, the user's palm is preferably pressed against a back portion of the handle 730 for stabilization. In one embodiment shown in FIG. 10C, a connecting member 732 is attached to the handle 730, and the connecting member 732 is malleable or includes a spring element. A palm brace 734 is attached to the other end of the connecting member and is used to brace the surgical hand tool 700 against the user's palm for support when advancing the guidewire 703 or the balloon catheter 704. The user can bend or move the connecting member 732 into any position or shape desired to accommodate orientation preferences. In this embodiment, holding the brace allows the user to lightly place one or two fingers in the handle 730 to hold the surgical hand tool 700. Also, the spring structure of the connecting member 732 helps absorb some of the shock and motion the surgical hand tool 700 will experience while wiring the sinus.

Figure 10C:
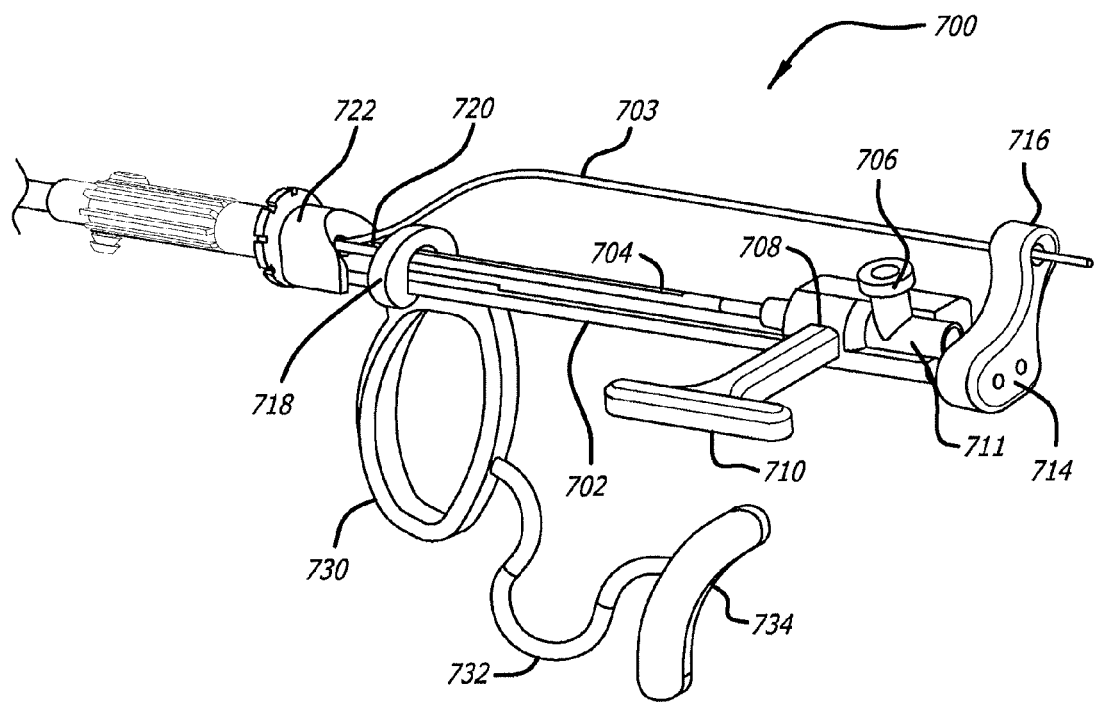
FIG. 10C is a perspective view of yet another embodiment of a surgical hand tool including a palm brace.

The surgical hand tool 700 shown in FIG. 10A or 10C allows the user to hold the device in the palm of the hand, balance the device with preferably the fourth and fifth fingers, and advance the guidewire 703 with the index finger and thumb. In this manner, the surgical hand tool 700 is held in the same hand that is used to control the guidewire 703. Further, the user has direct access to the guidewire 703, giving full tactile feel during advancing and steering of the guidewire. Balloon catheter 704 advancement is then achieved by reaching back with the thumb and pushing the balloon driver 708 forward (distally). The guidewire 703 can then be retracted using the index finger and thumb, and the balloon catheter 704 can be retracted by pulling the balloon driver 708 in the proximal direction.

Figure 10D:
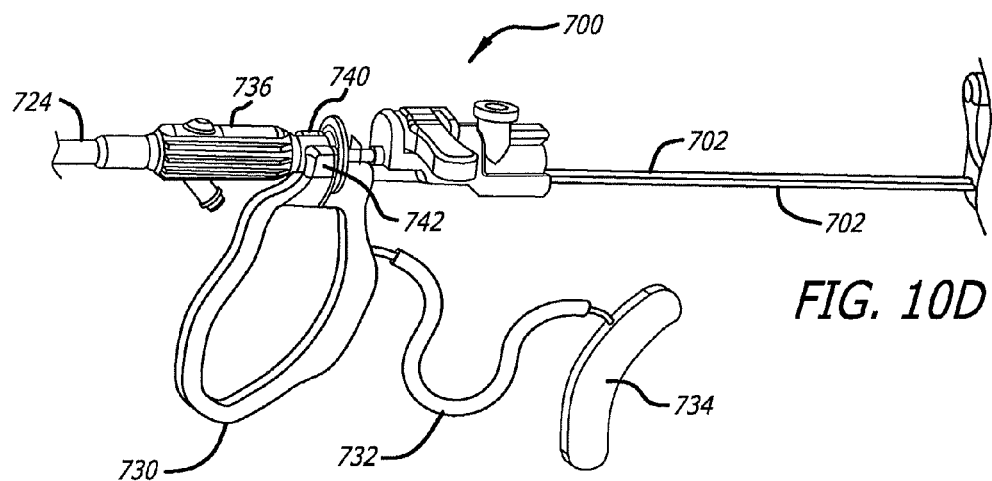
FIGS. 10D and 10E are perspective views of another embodiment of a surgical hand tool including a guide attachment.
Figure 10E:
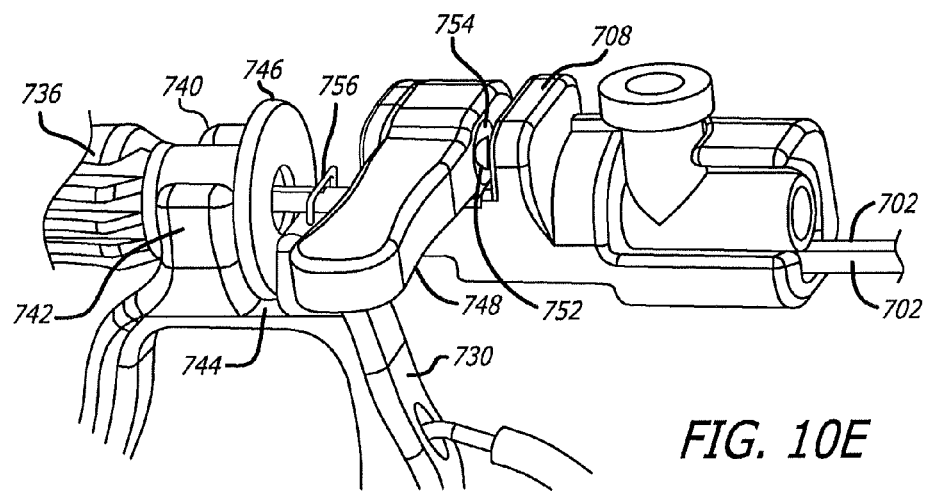

Another embodiment of the surgical hand tool 700 is shown in FIGS. 10D and 10E. In this embodiment, the guide catheter 724 is attached to a guide attachment 736 that is snap-fit into a guide snap 738 having a first flange 740 and a second flange 742. The flanges 740 and 742 are closer together in distance than the diameter of the guide attachment 736. The flanges 740 and 742 flex to let the guide attachment 736 enter into the guide snap 738 and then flex back to capture the guide attachment 736. Also, as best shown in FIG. 10E, a recess 744 is provided proximal to the flanges 740 and 742 to accept a proximal disc 746 of the guide attachment 736. This embodiment provides a more secure hold of the guide catheter 724.

As shown in FIG. 10E, the balloon driver 708 in this embodiment includes a moveable handle 748. The moveable handle 748 is attached to the balloon driver 708 by an axle 750, which allows the moveable handle 748 to swing from one side to another. A spring pin 752 located on the balloon driver 708 snaps into a hole 754 located on the moveable handle 748 when the moveable handle 748 is moved from one side to the other.

Also, as shown in both FIGS. 10D and 10E, the surgical hand tool 700 in this embodiment includes a wire ramp 756 that is formed wire or plastic attached to the handle 730. The first and second rails 702 of this embodiment are also moved closer together, and may even come into contact with one another. Having two rails 702 close together prevents rotation of the balloon driver 708 and reduces the profile of the surgical hand tool 700.

Figure 11:
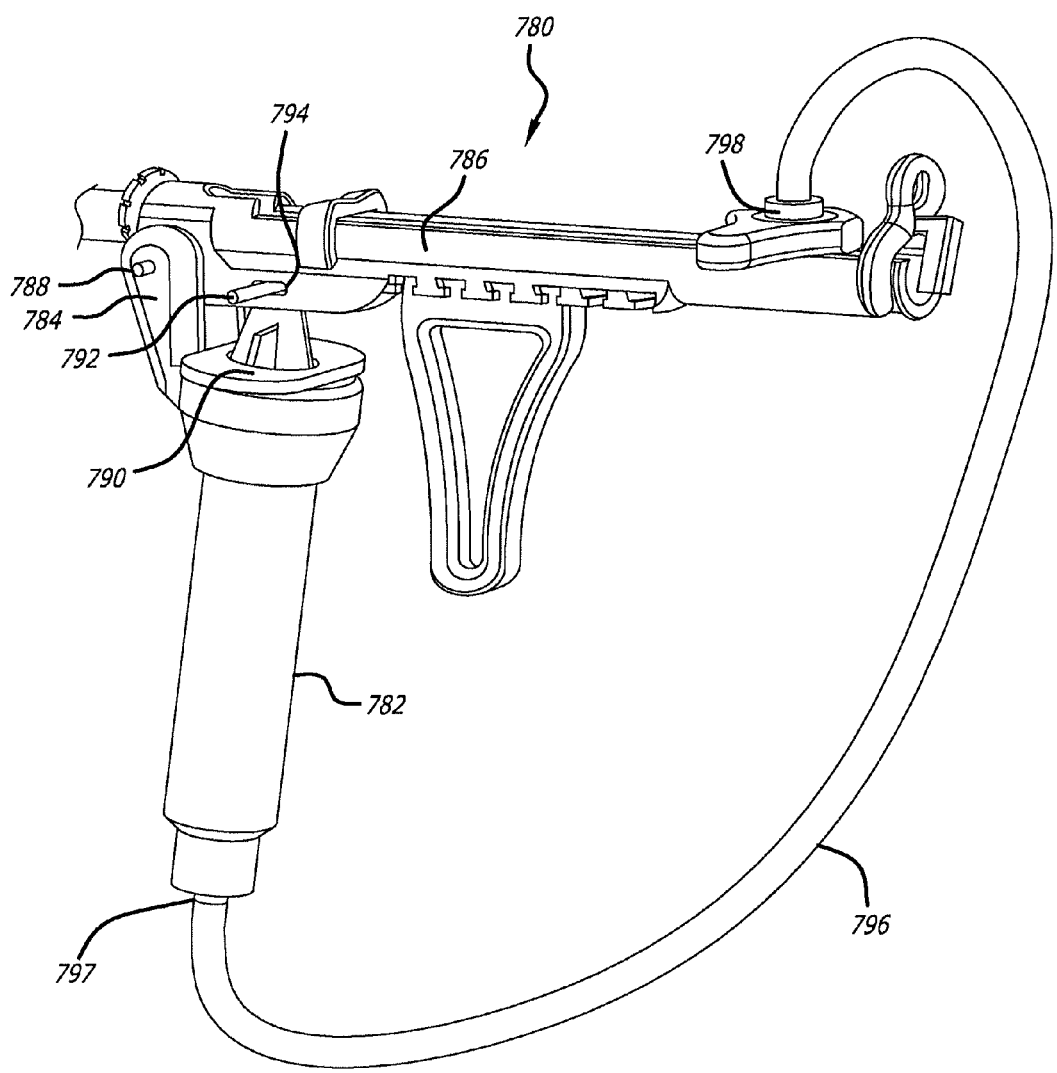
FIG. 11 is a perspective view of a surgical hand tool having a syringe mounted to a body of the surgical hand tool for fluid delivery.

Referring now to FIG. 11, another embodiment of a surgical hand tool 780 is shown that includes a front fluid delivery system for delivering fluid for inflating the balloon of a balloon catheter (not shown). In this embodiment, the surgical hand tool 780 includes a syringe barrel 782 connected to a mount 784 that is attached to a distal end of a proximal body 786 of the surgical hand tool 780 on an axle 788. As the mount 784 rotates about the axle 788, the syringe barrel 782 is driven up toward a plunger 790 attached to the proximal body 786 on axle 792. Along with allowing the plunger 790 to rotate about axle 792, the axle 792 also slides along slot 794 formed in the proximal body 786. When axle 792 slides distally, the axles 792 and 788 move closer together, and the mechanical advantage of plunger 790 and syringe barrel 782 system increases, but the "throw," which is the movement of the barrel 782 up along the plunger 790, decreases. In the reverse, when axle 792 slides proximally along the slot 794, the axles 792 and 788 move farther apart, and the mechanical advantage decreases while the throw increases. In operation, the user can rotate the syringe barrel 782 in a counter-clockwise direction to move the barrel 782 toward the plunger 790 and force fluid out of the barrel 782 and through an elongate tube 796 that is attached to an outlet 797 of the barrel 782. The elongate tube 796 is also attached to a balloon inflation port 798 of the balloon catheter at the other end. There is a spring (not shown) in the syringe barrel 782 below the plunger 790 that drives the system back to a start position when the syringe is released.

Figure 12A:
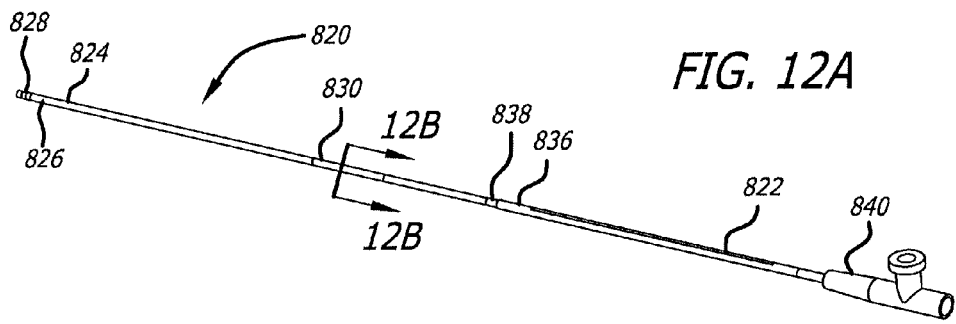
FIG. 12A is a perspective view of an irrigation catheter having a side cut-out.
Figure 12B:
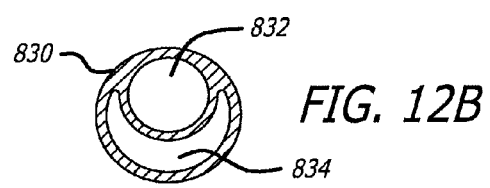
FIG. 12B is a cross-sectional view taken along line 12B-12B shown in FIG. 12A.

Referring now to FIGS. 12A and 12B, a side-loaded irrigation catheter 820 is shown for use with any of the surgical hand tools 400, 440, 490, 510, 550, 700 or 780 described above. The irrigation catheter 820 includes a side cut-out or window 822 for guidewire access. A distal section 824 of the irrigation catheter 820 may include a single lumen with side holes 826 at a distal end. There may also be a marker 828, such as a radiopaque marker or any other type of marker, disposed at the distal end of the distal section. The marker 828 informs the user of the location of the distal end of the irrigation catheter 820. The length of the distal section 824 can vary from about 1 to 4 inches.

Attached to a proximal end of the distal section 824 of the irrigation catheter 820 is a dual lumen extrusion 830. FIG. 12B shows a cross-section view of the dual lumen extrusion 830 that includes a first round lumen 832 for the guidewire and a second crescent lumen 834 for fluid or saline flow. At a transition between the dual lumen extrusion 830 and the distal section 824, the irrigation catheter 820 transitions from the dual lumen to the single lumen. Both lumens of the dual lumen extrusion 830 open into the single lumen of the distal section 824 to allow guidewire access and fluid flow to the distal end of the distal section. The dual lumen extrusion 830 extends to a proximal end of the irrigation catheter 820 and is at least partially covered by a supporting hypotube 836. Hypotube 836 may be similar to a hypotube on a balloon catheter to allow for smooth advancement through the surgical hand tools described above. As shown in FIG. 12A, the side cut-out 822 is through the wall of the supporting hypotube 836 and through the wall of the dual lumen extrusion 830 so that a guidewire can extend into the irrigation catheter 820 and the first round lumen 832. A marker band 838 may also be disposed on the supporting hypotube 836 such a distance from the distal end of the irrigation catheter to inform the user when the distal end is exiting the guide catheter. At a proximal end of the supporting hypotube 836 is a hub 840 for connecting a syringe to the irrigation catheter 820 to flush fluid through the catheter. In this embodiment, only one port is needed and can be in any orientation.

In another embodiment of the irrigation catheter 820, a flap or valve (not shown) may be disposed inside the single lumen of the distal section 824 to prevent fluid from flowing back proximally into the first round lumen 832 of the dual lumen extrusion 830.

Figure 13:
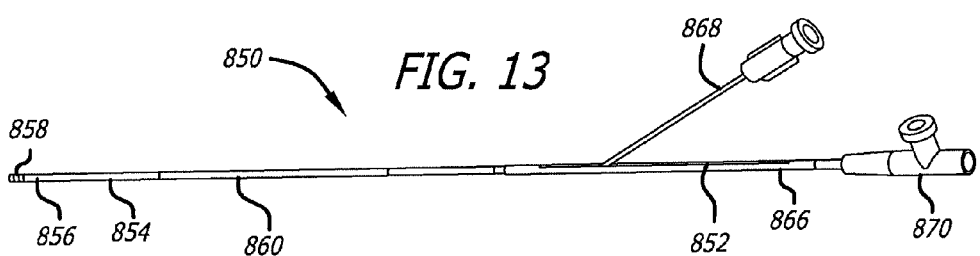
FIG. 13 is a side view of an irrigation catheter having a side cut-out and a single lumen.

Referring now to FIG. 13, a side-loaded irrigation catheter 850 is shown for use with any of the surgical hand tools 400, 440, 490, 510, 550, 700 or 780 described above. In one embodiment, the irrigation catheter 850 includes one lumen for greater fluid flow. A side cut-out, window or open channel 852 is provided on the irrigation catheter. A distal section 854 of the irrigation catheter 850 may include a single lumen with side holes 856 at a distal end. Any number of side holes can be provided at the distal end. There may also be a marker 858, such as a radiopaque marker or any other type of marker, disposed at the distal end of the distal section. The length of the distal section 854 can vary from about 1 to 4 inches.

Attached to a proximal end of the distal section 854 of the irrigation catheter 850 is a single lumen extrusion 860. The single lumen extrusion 860 extends to a proximal end of the irrigation catheter 850 and is at least partially covered by a supporting hypotube 866. Hypotube 866 may be similar to a hypotube on a balloon catheter to allow for smooth advancement through the surgical hand tools described above. As shown in FIG. 13, the side cut-out 852 is through the wall of the supporting hypotube 866 and through the wall of the single lumen extrusion 860 so that a guidewire can extend into the irrigation catheter 850. An irrigation syringe 868 can also extend into the irrigation catheter 850 through the cut-out 852 to flush fluid through the catheter. A marker band may also be disposed on the supporting hypotube 866 such a distance from the distal end of the irrigation catheter to inform the user when the distal end is exiting the guide catheter. At a proximal end of the supporting hypotube 866 is a hub 870 for connecting a syringe to the irrigation catheter 820 to flush fluid through the catheter. In this embodiment, only one port is needed and can be in any orientation. In another embodiment, the elongate tube of the distal section 854 may extend to the proximal end of the irrigation catheter without the having a single lumen extrusion or a supporting hypotube. In this embodiment, the cut-out 852 would extend through the elongate tube near its proximal end.

Figure 14A:
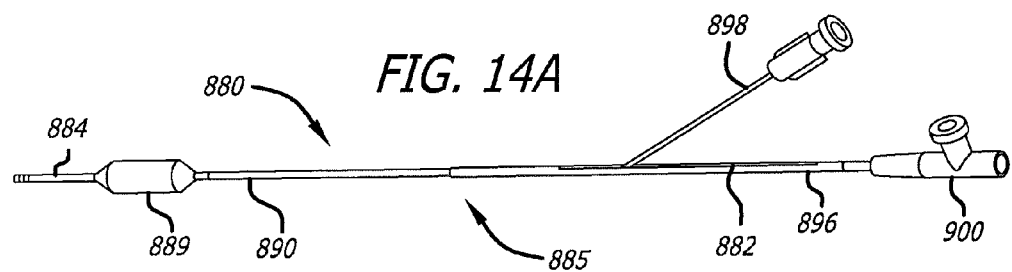
FIGS. 14A and 14B are side views of a balloon irrigation catheter having a side cut-out.
Figure 14B:
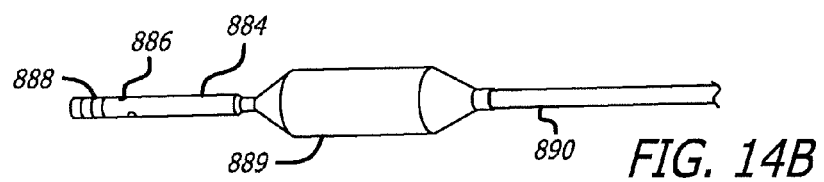

The distal section of the irrigation catheter can be disposed on the distal end of a balloon catheter instead of being a separate device as shown in FIGS. 12A and 13. A balloon catheter with an irrigation distal end 880 is shown in FIGS. 14A and 14B, and allows a physician to flush the sinus after dilation without having to remove the balloon catheter. The balloon irrigation catheter 880 is for use with any of the surgical hand tools 400, 440, 490, 510, 550, 700 or 780 described above. A side cut-out, window or open channel 882 is provided on the balloon irrigation catheter 880. A distal irrigation section 884 may be attached to the distal end of a balloon catheter 885 and includes a single lumen with side holes 886 as best shown in FIG. 14B. Any number of side holes can be provided on the distal irrigation section 884. There may also be a marker 888, such as a radiopaque marker or any other type of marker, disposed at the distal end of the distal irrigation section. The length of the distal irrigation section 884 can vary from about 1 to 4 inches.

Attached to a proximal end of the distal irrigation section 884 is the balloon catheter 885, which includes an inflation member 889. The balloon catheter 885 includes a dual lumen tubing 890 having a cross-section similar to that shown in FIG. 12B, with a first round lumen and a second crescent lumen. In this embodiment, the first round lumen can accommodate the guidewire and/or syringe to flush fluid into the target area. The second crescent lumen can be the inflation lumen for inflating the inflation member or balloon 889. The dual lumen tubing 890 extends to a proximal end of the balloon irrigation catheter 880 and may even include a supporting hypotube 896 at least partially covering the dual lumen tubing 890. Hypotube 896 allows for smooth advancement through the surgical hand tools described above. The side cut-out 882 is through the wall of the supporting hypotube 896 and through the wall of the dual lumen tubing 890 so that a guidewire can extend into the balloon irrigation catheter 880. An irrigation syringe 898 can also extend into the irrigation catheter 850 through the cut-out 852 to flush fluid through the catheter. The irrigation syringe 898 may include a bent steel hypotube or flexible polymer extrusion. An outer diameter of the irrigation syringe should be small enough to fit within the side cut-out 882 of the balloon irrigation catheter 880. Also, the irrigation syringe 898 includes a blunt distal tip (not shown) that is dull to avoid cutting or scratching the inner lumen of the balloon irrigation catheter 880.

A marker band may also be disposed on the supporting hypotube 896 such a distance from the distal end of the balloon irrigation catheter 880 to inform the user when the distal end is exiting the guide catheter. Also, a second marker band may be disposed such a distance from the distal end of the balloon irrigation catheter to indicate when the inflation member 889 has exited the guide catheter. At a proximal end of the supporting hypotube 896 is a hub 900 for connecting a syringe to the balloon irrigation catheter 880 to flush fluid through the catheter.

In operation, a user may insert the balloon irrigation catheter 880 along a guidewire into a sinus. The inflation member 889 of the balloon irrigation catheter can be inflated once it is in the proper position to dilate the sinus. After dilation, the guidewire can be removed from the balloon irrigation catheter, and the irrigation syringe 898 can be inserted into the side cut-out 882. The irrigation syringe 898 is slid distally in the balloon irrigation catheter 880 so that its end is within the closed section of the lumen within the catheter 880. Once properly inserted into the balloon irrigation catheter 880, fluid, such as saline, can be injected through the balloon irrigation catheter using the irrigation syringe 898 so that fluid will exit the side holes 886 of the distal irrigation section 884.

Figure 15A:
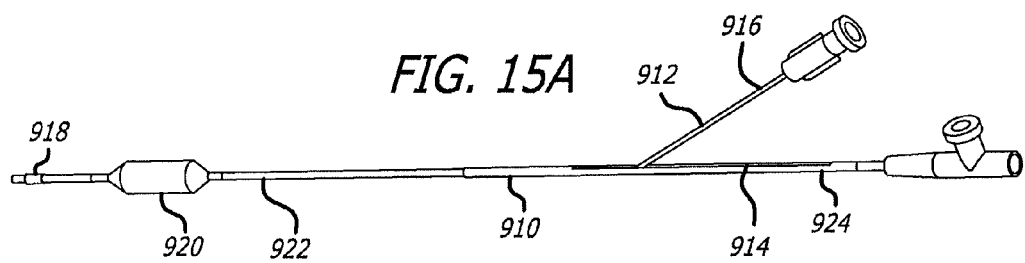
FIG. 15A is a side view an irrigation syringe inserted through a side window of a balloon catheter.
Figure 15B:
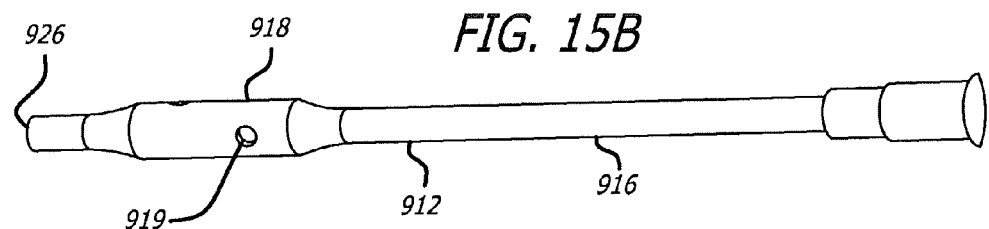
FIG. 15B is a side view of a distal end the irrigation syringe shown in FIG. 15A.

In yet another embodiment, an irrigation catheter can be sized such that it fits through the side cut-out of a balloon catheter and into the wire lumen of the balloon catheter. FIGS. 15A and 15B depict a balloon catheter 910 and an irrigation syringe 912 that is used to flush the sinus after dilation. A side cut-out, window or open channel 914 is disposed on the balloon catheter 910 and provides an opening for inserting the irrigation syringe 912. The irrigation syringe includes a bent steel hypotube or flexible polymer extrusion 916 with a porous balloon 918 mounted at the distal end of the hypotube 916. When fluid is injected into the irrigation syringe 912, porous balloon 918 expands to open pores 919 and then fluid flows out of the pores. Once the pressure from the fluid is removed, the porous balloon 918 collapses so that the irrigation syringe 912 can be removed from the balloon catheter 910.

As shown in FIG. 15A, the balloon catheter 910 includes an inflation member 920. The balloon catheter 910 also includes a dual lumen tubing 922 having a cross-section similar to that shown in FIG. 12B, with a first round lumen and a second crescent lumen. In this embodiment, the first round lumen can accommodate the guidewire and/or irrigation syringe 912 to flush fluid into the sinus. The second crescent lumen can be the inflation lumen for inflating the inflation member or balloon 920. The dual lumen tubing 922 extends to a proximal end of the balloon catheter 910 and may even include a supporting hypotube 924 at least partially covering the dual lumen tubing 922. Hypotube 924 allows for smooth advancement through the surgical hand tools described above. The side cut-out 914 is through the wall of the supporting hypotube 924 and through the wall of the dual lumen tubing 922 so that the guidewire and/or irrigation syringe 912 can extend into the balloon catheter 910. An outer diameter of the irrigation syringe 912 should be small enough to fit within the side cut-out 914 of the balloon catheter 910. Also, the irrigation syringe 912 includes a blunt distal tip 926 that is dull to avoid cutting or scratching the inner lumen of the balloon irrigation catheter 910.

The surgical hand tools 400, 440, 490, 510, 550, 700 or 780 described above can each be used in a similar manner for dilating an anatomical region. In use, the surgical hand tool is introduced into a head of a patient, typically through a nostril but in alternative embodiments through another opening such as a canine fossa puncture. In one embodiment, an endoscope may be first inserted through a nostril of a patient, followed by insertion of a guide catheter. In other embodiments, the endoscope and guide catheter can be inserted together. The endoscope and guide catheter are positioned such that the distal tip of guide catheter is located near an anatomical region to be accessed and the endoscope can view the targeted anatomical region. Thereafter, the guidewire is introduced through the guide catheter such that the distal tip of the guidewire is located at or near the targeted anatomical region. During this step, the guidewire may be navigated through the anatomy using the torquing device of the guidewire. In one embodiment, the guidewire is positioned across a paranasal sinus ostium to be dilated. Thereafter, the balloon catheter is advanced over the guidewire into the anatomy by pushing the slide or balloon catheter driver in the distal direction. Once the balloon of the balloon catheter is correctly positioned, the balloon catheter is used to perform a diagnostic or therapeutic procedure. In one embodiment, the balloon catheter is used to dilate an opening leading to a paranasal sinus such as a paranasal sinus ostium. Once the procedure is complete, the endoscope and surgical hand tool 400, 440, 490, 510, 550, 700 or 780 are removed from the targeted anatomical region and the patient.

Figure 16:
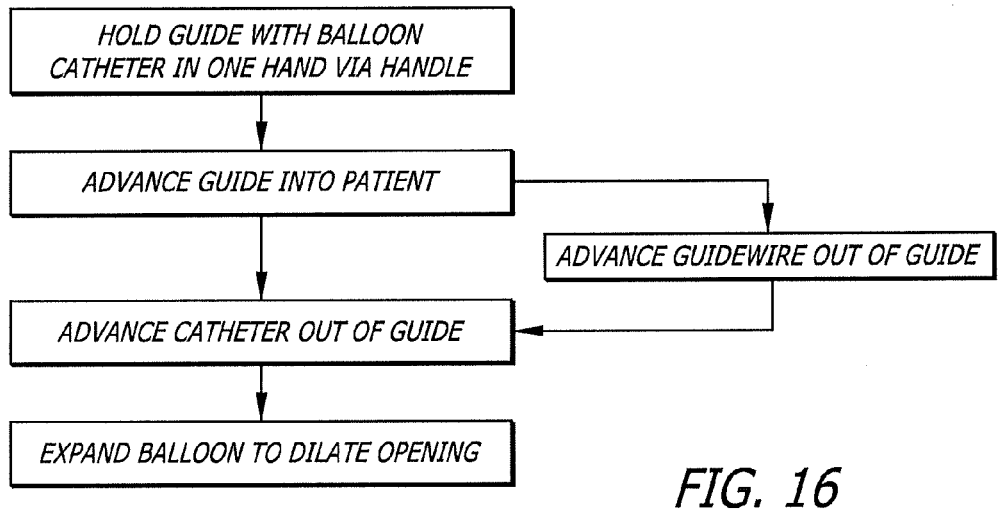
FIG. 16 is a flow diagram of a method for treating sinus disorders including holding a guide catheter and balloon catheter in one hand.

FIG. 16 illustrates one embodiment of a method for using a hand tool 400, 440, 490, 510, 550, 700 or 780 such as those described above. As a first step, a guide with a balloon catheter disposed in its lumen is held with one hand via a handle. The guide, with the balloon catheter inside it, is then advanced into a human or animal subject. This advancement may be into a nostril or through some other access pathway, such as through a canine fossa puncture into a maxillary sinus. In some embodiments, the method may include forming a manmade opening into a paransal sinus, such as a canine fossue puncture, before the advancing step. In various embodiments, the guide/catheter combination may be advanced before, during or after an endoscope is advanced into the subject through the same or a different access route.

When the guide is positioned at a desired location in the subject, such as with its distal end near a paranasal sinus ostium, in some embodiments the balloon catheter may be advanced out of the guide to position a balloon of the catheter in the sinus opening. Some embodiments may optionally include an additional step of advancing a guidewire out of the guide and then advancing the balloon catheter out of the guide over the guidewire. Once the balloon of the balloon catheter is in a desired location relative to the opening of the paransal sinus ostium, the balloon may then be expanded to dilate the opening. The guide and balloon catheter may then be removed from the subject.

A number of different variations may be made to the above-described method in various embodiments. For example, as described further above, in some embodiments an endoscope may also be attached to the handle such that the guide, balloon catheter and endoscope may be advanced into the subject at the same time. In some embodiments, alternatively, just the guide is coupled with the handle, the balloon catheter is preloaded in the guide and handle, and the guidewire is preloaded in the balloon catheter. In some embodiments a lighted guidewire may be used, in which case the guidewire may be illuminated during any suitable portion of the procedure. Some embodiments of the method may also include an irrigation procedure, in which an irrigation catheter is advanced into a paranasal sinus and used to flush mucus and/or other material out of the sinus. Thus, as has been described in greater detail above, in various alternative embodiments the method of the present invention may include a number of different steps and variations.

In all of the embodiments above, the guidewire used can be any conventional guidewire. It has also been contemplated that an illuminating guidewire device can also be used, such as the device disclosed in U.S. patent application Ser. No. 11/522,497, now U.S. Pat. No. 7,559,925, issued on Jul. 14, 2009, which is herein incorporated by reference. The illuminating guidewire device is connected to a light source and includes an illuminating portion at a distal end that illuminates. Illumination of the illuminating guidewire device can be used to visually confirm the positioning of a distal end portion of an illuminating device placed within a patient. In use, a distal end portion of an illuminating device is inserted internally into a patient, and emits light from the distal end portion of the illuminating device. Then, the physician can observe transillumination resulting from the light emitted from the distal end portion of the illuminating device that occurs on an external surface of the patient, which correlates the location of the observed transillumination on the external surface of the patient with an internal location of the patient that underlies the location of observed transillumination. This confirms positioning of the distal end portion of the illuminating device.

Any of the sinuplasty devices and systems 200, 250, 300, 370, 400, 440, 490, 510, 550, 700, 780, 820, 850, 880, 910 and 912 can be packaged or kilted ready for use. In this embodiment, the device or system would be placed in a single package for a physician to open immediately before the procedure or surgery. In certain embodiments, different types of kits can be packed with various instruments, for example, straight and/or curved guide catheters. In this way, kits can be prepared for specific procedures, such as for use in the maxillary sinus or use in the frontal sinus. Various kits may be provided, such as but not limited to "complete" and "partial" kits. In one embodiment, for example, a complete kit may include a guide catheter, an illuminating guidewire, a balloon catheter, and an integrated inflation device. Optionally, an irrigation catheter, extra or different guidewire, extra or different balloon catheters and/or the like may be included. A partial kit, in one embodiment, may include balloon catheter integrated with a handle and inflation device. A guide catheter, illuminating guidewire, irrigation catheter and/or the like may be provided as separate packets or the like. Of course, any combination of the various devices and elements described in this application may be kilted together in various alternative embodiments. In some embodiments, a kit may also include an endoscope, such as a swing prism endoscope. Such swing prism endoscopes are described in greater detail in U.S. Patent Application No. 61/084,949, entitled Swing Prism Endoscope, and filed Jul. 30, 2008, now expired, the full disclosure of which is hereby incorporated by reference.

The device may also be packaged with the various devices of the system integrated together and ready for use once the device or system is removed from the package. For example, the balloon catheter can be positioned within the guide catheter. Also, the inflation device may already be attached to the balloon catheter in the package in certain embodiments, unless it eases fluid preparation to have the inflation device unattached. The suction lumen can also be attached to the guide catheter, and the fluid lumen can be attached to the endoscope, in embodiments that include the endoscope packaged together with the device or system. Further the guide catheters can be connected to the proximal body of the devices 200, 250, 400, 440, 490, 510, 550, 700 and 780. For the balloon sinuplasty and endoscope integration systems 300 and 370, the endoscope can be pre-attached to the guide catheter. In other embodiments, though, the endoscope may not be packaged with the device or the integrated system. This would allow the physician to choose a preferred endoscope for use during the procedure or surgery.

Packaging the devices and systems for immediate use saves the physician time in preparation and setup of the devices and systems 200, 250, 300, 370, 400, 440, 490, 510, 550, 700, 780, 820, 850, 880, 910 and 912. The devices and systems can be sterilized before packaging and will not need to be flushed in preparation for surgery. The physician should only have to plug in fluid lumens and attach a light cable to the endoscope before use of the kitted systems. For the packages including the surgical hand tools 200, 250, 400, 440, 490, 510 550, 700 or 780, the physician may also have to choose and prepare an endoscope for the procedure if one is not provided in the kit. Also, in certain embodiments, a guidewire can be included with the kit, and even positioned within the balloon catheter and guide catheter of the device of systems. However, in other embodiments, the guidewire is not included in the packaged kit, and the physician may choose a preferred guidewire to perform the procedure.

The rigid or flexible endoscopes disclosed herein may have a range of view ranging from 0 degrees to 145 degrees. The embodiments of endoscopes comprising a curved, bent or angled region may be manufactured by curving or bending the optical fibers before fusing the optical fibers. The optical fibers may be fused for example by heating them to a temperature ranging from 500 to 700 degrees Celsius or by using suitable epoxy adhesives to attach the optical fibers to each other. The endoscopes may be made using reduced cladding thickness optical fibers to allow curved, bent or angled regions with a large angle or curvature but a small radius of curvature. The endoscopes may also be made using glass/glass/polymer (GGP) multimode fiber such as the ones made by 3M to allow curved, bent or angled regions with a large angle or curvature but a small radius of curvature. For example, in embodiments of endoscopes that have a bent, curved or angled region enclosing an angle of 90 degrees or more, the radius of curvature of the bent, curved or angled region may preferably be less than or equal to 1.5 cm. Such endoscopes comprising curved, bent or angled regions with a large angle or curvature but a small radius of curvature are especially useful to enable a user to access the maxillary sinuses.

The embodiments herein have been described primarily in conjunction with minimally invasive procedures, but they can also be used advantageously with existing open surgery or laparoscopic surgery techniques. For example, the methods and devices disclosed herein may be combined with one or more techniques of Functional Endoscopic Sinus Surgery (FESS). In FESS, a surgeon may remove diseased or hypertrophic tissue or bone and may enlarge the ostia of paranasal sinuses to restore normal drainage of the sinuses. It is typically performed with the patient under general anesthesia using endoscopic visualization.

Although FESS continues to be the gold standard therapy for severe sinuses, it has several shortfalls such as post-operative pain and bleeding associated with the procedure, failure to relieve symptoms in a significant subset of patients, risk of orbital, intracranial and sinonasal injuries, etc. Replacing one or more steps of FESS may reduce the shortfalls associated with the traditional FESS. The following are some examples of procedures involving a combination of FESS and the procedures disclosed in this patent application and the patent applications incorporated herein by reference.

1. In one combination procedure, a maxillary sinus is treated by balloon dilation with or without total or partial removal of the uncinate. Total or partial removal of the uncinate may make it easier or faster for some physicians to visualize and access the maxillary sinus.

2. In another combination procedure, a maxillary sinus is treated by balloon dilation in conjunction with removal of a nasal turbinate. During this combination procedure, a part or the entire nasal turbinate e.g. the middle turbinate may be removed. Removing a part or the entire middle turbinate provides additional working space in the region medial to the uncinate for instruments. This may potentially make the combination procedure easier or faster.

3. In another combination procedure, a sphenoid sinus ostium is treated by balloon dilation in conjunction with ethmoidectomy. The step of ethmoidectomy may enable a physician to introduce a guide catheter through the middle meatus to the sphenoid sinus ostium. This may potentially enable easy access to the sphenoid sinus ostium.

4. In another combination procedure, a frontal sinus is treated by balloon dilation in conjunction with middle turbinate resection and/or ethmoidectomy. This combination procedure may make easier for a physician to find, visualize or access the frontal sinus once anatomical structures like Ethmoid bulla, turbinate, etc. are removed or reduced.

5. In another type of combination procedures, multiple sinuses are treated by balloon dilation with no or minimal tissue or bone removal. This is then followed by standard techniques to treat sinus disease. Examples of such combination procedures include:

5A. Frontal, maxillary, or sphenoid sinuses are treated by balloon dilation. Also, ethmoidectomy is performed while preserving the uncinate. The presence of the uncinate may preserve the natural function of the uncinate. This in turn may lead to lower incidence of complications like infection, etc. in the sinuses.

5B. Any paranasal sinus may be treated by balloon dilation combined with a second procedure including, but not limited to ethmoidectomy, septoplasty, reduction of a turbinate (e.g. inferior turbinate, middle turbinate, etc.), etc.

6. Any of the procedures disclosed herein may be performed in conjunction with irrigation and suction of one or more paranasal sinuses with a flexible catheter or rigid instrument. A flexible catheter is particularly useful to reach regions that are difficult to access by rigid instruments. Such regions may be located in lateral aspects of the frontal sinuses, the inferior or medial aspects of the maxillary sinuses, etc.

7. Any of the procedures disclosed herein may further include removal of one or more polyps. Polyp removal by standard techniques such as using shavers can be combined with balloon dilation of various paranasal sinus ostia. Once one or more polyps are removed, one or more ostia of paranasal sinuses may be dilated by balloon dilation.

8. In another type of combination procedures, balloon dilation of one or more paranasal sinus ostia may be performed to revise a previously performed surgery or in conjunction with standard endoscopic sinus surgery techniques. Examples of such procedures include:

8A. Treating scar formation over frontal recess: In this combination procedure, an attempt is made to access frontal recess with a guidewire. A balloon catheter is then passed over the guidewire. If the guidewire is unable to access the frontal sinus ostia because of scarring or because the frontal sinus ostia are too small, a surgical instrument e.g. curette or seeker may be used to open or puncture scar tissue or adhesions or the frontal sinus ostia. Such scar tissue or adhesions may be caused for example due to infection, prior surgery, etc. Thereafter, the frontal sinus ostia may be dilated by balloon dilation.

8B. Combination procedures similar to the abovementioned combination procedure may be performed to treat scarring near sphenoid sinuses and maxillary sinuses.

9. In another type of combination procedures, one or more paranasal sinuses e.g. a maxillary sinus may be accessed by an artificially created opening leading to the sinuses. Thereafter, a diagnostic or therapeutic procedure disclosed herein or in the patent documents incorporated herein by reference may be performed. The artificially created opening may be used to endoscopically visualize the placement of devices such as balloon catheters, guidewires, or other devices through a natural ostium of the paranasal sinus. The artificially created opening may also be used to introduce one or more diagnostic, therapeutic or access devices. The artificially created opening may be used to introduce liquids including, but not limited to solutions of antibiotics, solutions of anti-inflammatory agents, etc. The artificially created opening may be made by using suitable devices including, but not limited to drilling devices, chopping devices, puncturing devices, etc.

Some specific examples of hybrid procedures of the present invention are shown in the flow diagrams of FIGS. 17-20.

Figure 17:
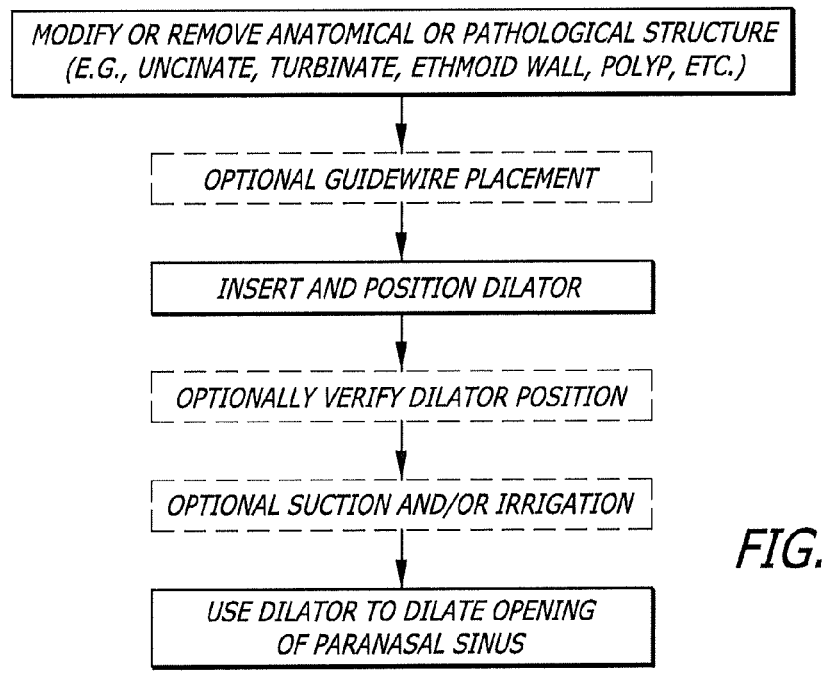
FIG. 17 is a flow diagram of a method useable for treating sinus disorders by removal or modification of an anatomical or pathological structure in combination with dilation of an opening of a paranasal sinus.

FIG. 17 shows steps in a method wherein an anatomical or pathological structure, such as the uncinate process, a turbinate, the wall of an ethmoid air cell, a polyp, etc. is removed or substantially modified and a dilator (e.g., the balloon of a balloon catheter) is positioned within an opening of a paranasal sinus and used to dilate that opening. Removal or modification of the anatomical or pathological structure may provide clearer access to and/or visibility of certain anatomical structures during the procedure or during post-operative examinations and follow-up.

Figure 18:
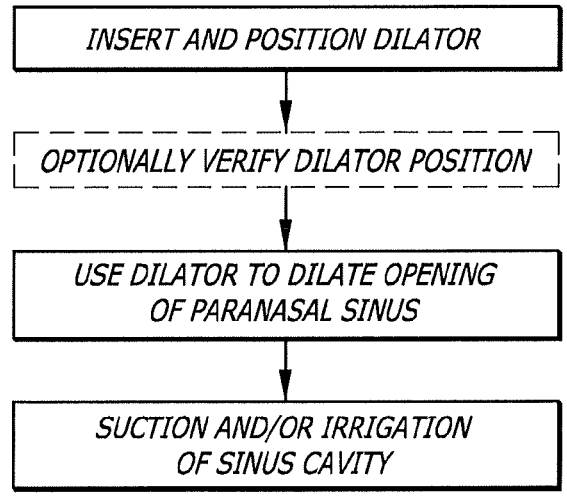
FIG. 18 is a flow diagram of a method useable for treating sinus disorders by dilation of an opening of a paranasal sinus in combination with suction and/or irrigation of a sinus cavity.

FIG. 18 shows steps in a method where a dilator such as the balloon of a balloon catheter is positioned in the opening of a paransal sinus and used to dilate that opening and, either before or after such dilation, the cavity of the paranasal sinus is suctioned or irrigated. In cases where a balloon catheter or other dilator device having a through lumen is used to accomplish the dilation step, the irrigation and/or suction step may be carried out by passing fluid or negative pressure through the through lumen of the dilation catheter. Or, a guidewire may be advanced into or near the sinus cavity during the dilation step and, thereafter, a suction and/or irrigation device may be advanced over such guidewire and used to carry out the suction and/or irrigation step.

Figure 19:
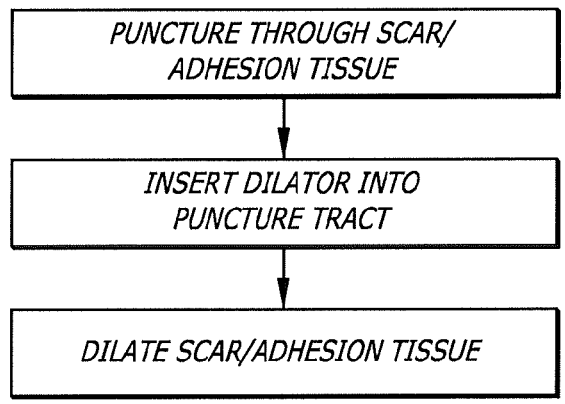
FIG. 19 is a flow diagram of a method useable for treating conditions where unwanted scar or adhesion tissue has formed by forming a puncture tract in the scar or adhesion tissue, inserting a dilator into the puncture tract and dilating the puncture tract.

FIG. 19 shows steps in a method where scar or adhesion tissue has formed in a location that obstructs a lumen, orifice, or passageway (e.g., scar tissue obstruction the opening of a paranasal sinus) and a puncture tract is initially formed in the scar or adhesion tissue. This may be accomplished by pushing a needle, seeker, probe, guidewire or other penetrator through the tissue. Thereafter, a dilator (e.g., a balloon catheter) is advanced into the puncture tract and is used to dilate the puncture tract, thereby relieving the obstruction caused by the aberrant scar or adhesion tissue.

Figure 20:
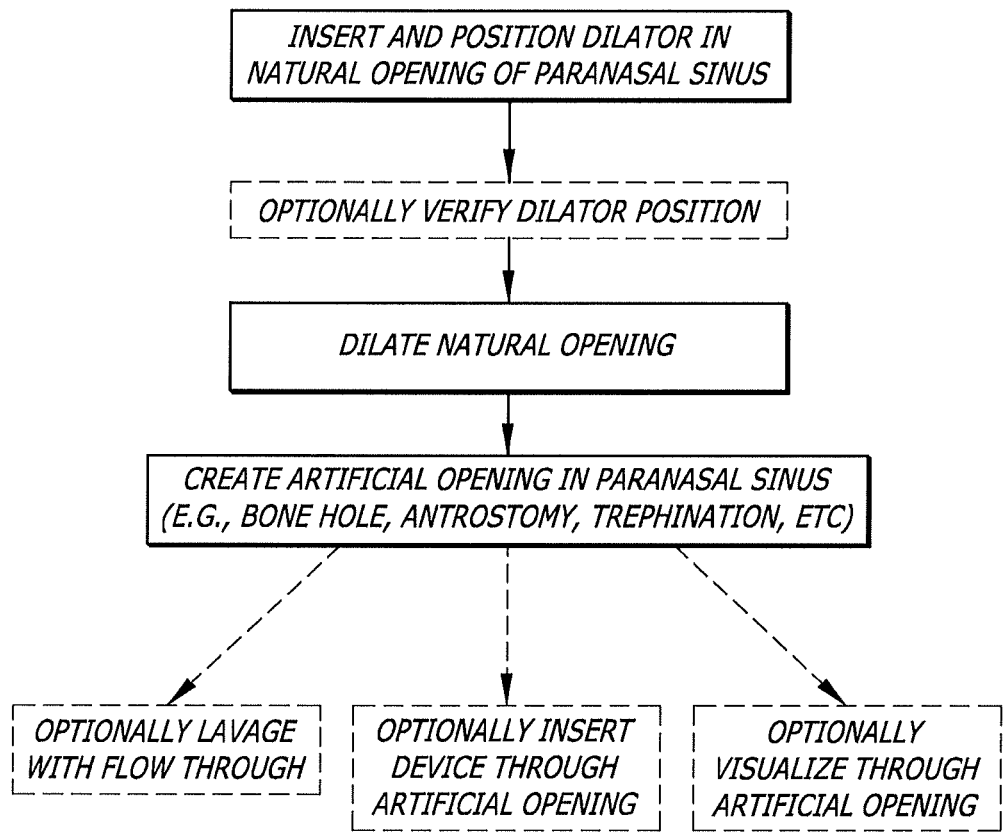
FIG. 20 a flow diagram of a method useable for treating sinus disorders by dilation of a natural opening of a paranasal sinus in combination with the creation of a new opening in the paranasal sinus.

FIG. 20 shows steps in a method wherein a dilator (e.g., the balloon of a balloon catheter) is placed in a pre-existing opening of a paranasal sinus, such as the natural ostium of the sinus (or a previously surgically altered ostium) and is used to dilate that opening. Also, a separate opening is created in that paranasal sinus, either from the nasal cavity or through the exterior of the face (e.g., a bore hole, antrostomy or trephination). This may provide improved ventilation and/or drainage of the sinus cavity. Optionally, the two openings may then be used to perform other procedures. For example, "flow through" irrigation may be carried out by passing irrigation solution through one of the openings and out of the other. Or, a device may be inserted through one of the openings, leaving the other opening unobstructed. Or, the physician may visualize (e.g., through an endoscope) through the newly created opening while treated the pre-existing opening or performing other diagnosis or treatment of the sinus cavity.

The devices and methods of the present invention relate to the accessing and dilation or modification of sinus ostia or other passageways within the ear nose and throat. These devices and methods may be used alone or may be used in conjunction with other surgical or non-surgical treatments, including but not limited to the delivery or implantation of devices and drugs or other substances as described in co-pending U.S. patent application Ser. No. 10/912,578 entitled Implantable Devices and Methods for Delivering Drugs and Other Substances to Treat Sinusitis and Other Disorders filed on Aug. 4, 2004, now U.S. Pat. No. 7,361,168, issued on Apr. 22, 2008, the entire disclosure of which is expressly incorporated herein by reference.

The invention has been described with reference to certain examples or embodiments, but various additions, deletions, alterations and modifications may be made to these examples and embodiments without departing from the intended spirit and scope of the invention. For example, any element or attribute of one embodiment or example may be incorporated into or used with another embodiment or example, unless to do so would render the embodiment or example unsuitable for its intended use. All reasonable additions, deletions, modifications and alterations are to be considered equivalents of the described examples and embodiments and are to be included within the scope of the following claims.

What is claimed:

1. A device for dilating an ostium of a paranasal sinus of a human or animal subject, the device comprising:
   (a) a handle comprising a proximal end and a distal portion;
   (b) an elongate guide shaft extending distally from the handle, wherein the elongate guide shaft defines a guide shaft lumen, said elongate shaft comprising a proximal portion and a distal end, wherein the distal end comprises a preformed fixed bend;
   (c) a guidewire slidably positioned within the guide shaft lumen;
   (d) a dilator configured to transition between a non-expanded configuration and an expanded configuration, wherein the dilator is configured to fit in an ostium of a paranasal sinus in the non-expanded configuration, wherein the dilator is longitudinally slidable relative to the elongate guide shaft and relative to the guidewire; and
   (e) a first slide member coupled with the dilator, wherein the first slide member is located between the proximal end and the distal portion of the handle, wherein the first slide member is slidable relative to the handle, wherein the first slide member is operable to slide the dilator longitudinally relative to the elongate guide shaft past the preformed fixed bend to a position that is distal of a tip of the elongate guide shaft without dilating the dilator, wherein the preformed fixed bend is configured to not change shape as the dilator moves past the preformed fixed bend.

2. The device of claim 1, wherein the dilator is slidably positioned within the guide shaft lumen.

3. The device of claim 1, further comprising a second slide member coupled with the guidewire, wherein the second slide member is slidable relative to the handle, wherein the second slide member is operable to slide the guidewire longitudinally relative to the elongate guide shaft.

4. The device of claim 3, wherein the second slide member is further operable to rotate the guidewire relative to the elongate guide shaft.

5. The device of claim 1, wherein the elongate guide shaft defines a longitudinal opening extending from the guide shaft lumen to an outer surface of the elongate guide shaft.

6. The device of claim 5, wherein the elongate guide shaft further includes a distal end and a proximal end, wherein at least one end of the longitudinal opening terminates at a longitudinal position located between the distal end and the proximal end of the elongate guide shaft.

7. The device of claim 5, wherein the first slide member is coupled with the dilator through the longitudinal opening.

8. The device of claim 1, wherein the handle defines a longitudinal opening.

9. The device of claim 8, wherein the first slide member is coupled with the dilator through the longitudinal opening.

10. The device of claim 1, further comprising a piercing member coupled with a distal end of the elongate guide shaft, wherein the piercing member is configured to pierce a hole into a paranasal sinus, wherein the distal end of the elongate guide shaft is configured to fit through a hole formed by the piercing member.

11. The device of claim 1, further comprising a fluid reservoir in fluid communication with the dilator.

12. The device of claim 11, further comprising an actuator coupled with the fluid reservoir, wherein the actuator is operable to drive fluid from the fluid reservoir to the dilator to thereby inflate the dilator into the expanded configuration.

13. The device of claim 1, wherein the bend comprises a curve.

14. The device of claim 1, wherein the bend comprises an oblique angle.

15. The device of claim 1, wherein the elongate guide shaft has a distal end, wherein the first slide member is operable to position a distal portion of the dilator distal to the distal end of the elongate guide shaft.

16. A device for dilating an ostium of a paranasal sinus of a human or animal subject, the device comprising:
    (a) a handle comprising a proximal end, wherein the handle defines a laterally presented slot located distal relative to the proximal end;
    (b) an elongate guide shaft extending distally from the handle, wherein the elongate guide shaft defines a guide shaft lumen, wherein the elongate guide shaft comprises a distal end wherein the distal end comprises a fixed bend;
    (c) a guidewire slidably positioned within the guide shaft lumen;
    (d) a dilation device comprising a dilator shaft, a dilator, and a sliding member, wherein the sliding member is configured to slide relative to the handle, wherein the sliding member is disposed within the laterally presented slot defined by the handle, wherein the dilator is configured to transition between a non-expanded configuration and an expanded configuration, wherein the dilator is configured to fit in an ostium of a paranasal sinus in the non-expanded configuration, wherein the dilator is longitudinally slidable past the fixed bend and out of a distal end of the elongate guide shaft, wherein the fixed bend is configured to not change shape as the dilator moves past the fixed bend, wherein the dilatation device is slidable relative to the guidewire; and
    (e) a hub positioned between the elongate guide shaft and the handle.

17. The device claim 16, further comprising a slide member slidably disposed relative to the handle, wherein the slide member is coupled with the dilator, wherein the slide member is operable to slide the dilator relative to the elongate guide shaft.

18. A device for dilating an ostium of a paranasal sinus of a human or animal subject, the device comprising:
    (a) a handle comprising a proximal end and a distal end, wherein the handle defines a channel between the proximal end and the distal end;
    (b) an elongate guide shaft extending distally from the handle, wherein the elongate guide shaft defines a guide shaft lumen, wherein the elongate guide shaft has a distal end with a preformed fixed bend;
    (c) a guidewire slidably positioned within the guide shaft lumen;
    (d) a dilator configured to transition between a non-expanded configuration and an expanded configuration, wherein the dilator is configured to fit in an ostium of a paranasal sinus in the non-expanded configuration, wherein the dilator is longitudinally slidable relative to the elongate guide shaft and relative to the guidewire;
    (e) an inflation port, wherein the inflation port is in fluid communication with the dilator; and
    (f) a slide member comprising a portion which extends laterally from the channel at a location in-between the proximal end and the distal end of the handle, wherein the slide member is mechanically coupled to the dilator such that the dilator is configured to slide longitudinally relative to the elongate guide shaft in response to longitudinal advancement of the slide member.

\* \* \* \* \*